(12) United States Patent
Lowman et al.

(10) Patent No.: US 11,008,609 B2
(45) Date of Patent: May 18, 2021

(54) COMPOSITIONS AND METHODS FOR IMMUNE REPERTOIRE SEQUENCING

(71) Applicant: Life Technologies Corporation, Carlsbad, CA (US)

(72) Inventors: Geoffrey Lowman, Carlsbad, CA (US); Timothy Looney, Redwood City, CA (US); Lifeng Lin, Daly City, CA (US); Elizabeth Linch, Menifee, CA (US); Lauren Miller, San Diego, CA (US)

(73) Assignee: Life Technologies Corporation, Carlsbad, CA (US)

( * ) Notice: Subject to any disclaimer, the term of this patent is extended or adjusted under 35 U.S.C. 154(b) by 207 days.

(21) Appl. No.: 16/120,045

(22) Filed: Aug. 31, 2018

(65) Prior Publication Data

US 2019/0085374 A1 Mar. 21, 2019

Related U.S. Application Data

(60) Provisional application No. 62/553,688, filed on Sep. 1, 2017, provisional application No. 62/586,129, filed on Nov. 14, 2017.

(51) Int. Cl.
| | |
|---|---|
| *C40B 50/06* | (2006.01) |
| *C12Q 1/686* | (2018.01) |
| *C12Q 1/6806* | (2018.01) |
| *C12Q 1/6869* | (2018.01) |
| *C40B 50/00* | (2006.01) |

(52) U.S. Cl.
CPC ........... *C12Q 1/686* (2013.01); *C12Q 1/6806* (2013.01); *C12Q 1/6869* (2013.01); *C40B 50/00* (2013.01); *C40B 50/06* (2013.01); *C12Q 2600/16* (2013.01)

(58) Field of Classification Search
None
See application file for complete search history.

(56) References Cited

U.S. PATENT DOCUMENTS

| | | |
|---|---|---|
| 7,785,783 B2 | 8/2010 | Morley et al. |
| 8,236,503 B2 | 8/2012 | Faham et al. |
| | (Continued) | |

FOREIGN PATENT DOCUMENTS

| | | |
|---|---|---|
| WO | WO-2010053587 A2 | 5/2010 |
| WO | WO-2011139371 A1 | 11/2011 |
| | (Continued) | |

OTHER PUBLICATIONS

Arden., "Human T-cell receptor variable gene segment families", Immunogenetics, 1995, 42(6), pp. 455-500.
(Continued)

*Primary Examiner* — Christian C Boesen

(57) ABSTRACT

The present disclosure provides methods, compositions, kits, and systems useful in the determination and evaluation of the immune repertoire using genomic DNA from a biological sample. In one aspect, target-specific primer panels provide for the effective amplification of sequences of T cell receptor and/or B cell receptor chains with improved sequencing accuracy and resolution over the repertoire. Nucleic acid sequences of variable regions associated with the immune cell receptor are determined to effectively portray clonal diversity of a biological sample and/or differences associated with the immune cell repertoire of a biological sample.

15 Claims, 2 Drawing Sheets

Specification includes a Sequence Listing.

(56) References Cited

U.S. PATENT DOCUMENTS

| | | | |
|---|---|---|---|
| 8,883,418 | B2 | 11/2014 | Pasqual et al. |
| 9,068,224 | B2 | 6/2015 | Fire et al. |
| 9,234,240 | B2 | 1/2016 | Quake et al. |
| 9,957,558 | B2 | 5/2018 | Leamon et al. |
| 2013/0059738 | A1 | 3/2013 | Leamon et al. |
| 2016/0002731 | A1* | 1/2016 | Robins .................. C12Q 1/6851 506/2 |
| 2018/0208984 | A1 | 7/2018 | Looney et al. |

FOREIGN PATENT DOCUMENTS

| | | |
|---|---|---|
| WO | WO-2011139372 A1 | 11/2011 |
| WO | WO-2012027503 A2 | 3/2012 |
| WO | WO-2013155119 A1 | 10/2013 |
| WO | WO-2013158936 A1 | 10/2013 |
| WO | WO-2013188471 A2 | 12/2013 |
| WO | WO-2014055561 A1 | 4/2014 |
| WO | WO-2014130685 A1 | 8/2014 |
| WO | WO-2014145992 A1 | 9/2014 |
| WO | WO-2015058159 A1 | 4/2015 |
| WO | WO-2015134787 A2 | 9/2015 |
| WO | WO-2016197131 A1 | 12/2016 |
| WO | WO-2017210469 A2 | 12/2017 |
| WO | WO-2018136562 A2 | 7/2018 |

OTHER PUBLICATIONS

Arstila et al., "A direct estimate of the human alphabeta T cell receptor diversity", Science, Oct. 29, 1999, 286(5441), pp. 958-961.

Bolotin et al., "Next generation sequencing for TCR repertoire profiling: platform-specific features and correction algorithms", Eur J Immunol., Nov. 2012, 42(11), pp. 3073-3083.

Brochet et al., "IMGT/V-QUEST: the highly customized and integrated system for IG and TR standardized V-J and V-D-J sequence analysis", Nucleic Acids Res., Jul. 1, 2008, 36:W503-508.

Calis et al., "Characterizing immune repertoires by high throughput sequencing: strategies and applications", Trends Immunol., Dec. 2014, 35(12), pp. 581-590.

Carlson et al., "Using synthetic templates to design an unbiased multiplex PCR assay", Nature Communications, 2013, 4(2680), pp. 1-9.

Chothia et al., "Canonical structures for the hypervariable regions of immunoglobulins", J. Mol. Biol., Aug. 20, 1987, 196(4), pp. 901-917.

Davis et al., "T-cell antigen receptor genes and T-cell recognition", Nature, 1998, vol. 334, pp. 395-402.

Hou X., et al., "Analysis of the Repertoire Features of TCR Beta Chain CDR3 in Human by High-Throughput Sequencing," Cellular Physiology and Biochemistry, vol. 39, No. 2, Jul. 29, 2016 (Jul. 29, 2016), pp. 651-667, XP055528308, CH, ISSN: 1015-8987, DOI: 10.1159/000445656.

International Search Report and Written Opinion for Application No. PCT/US2018/049259, dated Dec. 7, 2018, 15 pages.

Layton et al., "Estimating T-cell repertoire diversity: limitations of classical estimators and a new approach", (2015) Philosophical Transactions B, 370:20140291, pp. 1-11.

Liu et al., "Systematic Comparative Evaluation of Methods for Investigating the TCRβ Repertoire", PLOS ONE, Mar. 28, 2016, pp. 1-18.

Mackelprang, et al., "Sequence diversity, natural selection and linkage disequilibrium in the human T cell receptor alpha/delta locus", Hum Genet., Apr. 2006, 119(3), pp. 255-266.

Robins H.S., et al., "Comprehensive assessment of T-cell receptor β-chain diversity in αβ T cells", Blood, vol. 114, No. 19, Nov. 5, 2009 (Nov. 5, 2009), pp. 4099-4107.

Rosati E., et al., "Overview of Methodologies for T-Cell Receptor Repertoire Analysis," BMC Biotechnology, vol. 17, No. 1, Jul. 10, 2017 (Jul. 10, 2017), pp. 1-16, XP055518303, DOI: 10.1186/s12896-017-0379-9.

Rowen et al., "The complete 685-kilobase DNA sequence of the human beta T cell receptor locus", Science, Jun. 21, 1996, 272(5269), pp. 1755-1762.

Sandberg, et al., "Human T-cell lines with well-defined T-cell receptor gene rearrangements as controls for the BIOMED-2 multiplex polymerase chain reaction tubes", Leukemia, Feb. 2007, 21(2), pp. 230-237.

Van Dongen et al., "Design and standardization of PCR primers and protocols for detection of clonal immunoglobulin and T-cell receptor gene recombinations in suspect lymphoproliferations: Report of the BIOMED-2 Concerted Action BMH4-CT98-3936," Leukemia, Dec. 2003, 17(12):2257-317.

* cited by examiner

SEQUENCE LISTING

<160> NUMBER OF SEQ ID NOS: 505

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaaatacctg gtcacacaga cggga                                          25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aagataccgg gttacccagt ttgga                                          25

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
actcaaactc caagacatct gatcaaaacg                                     30

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agaatcccag acacaagatc acaaa                                          25

```
<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agagtccaag acacaagatc acaga                                           25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtccccaag acatctgatc agaga                                           25

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atcaatggcc agcgaccctg g                                               21

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccaaagtccc acacacctga tcaaa                                           25

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cccagacacc aaaatacctg g                                               21

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctcaacatcc gagtagggtt atctgta                                         27

<210> SEQ ID NO 11
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcagtcccc aaagtacctg t                                              21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctggaatcac ccagagccc                                                 19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctggagtctc ccacaaccc                                                 19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctggagtctc ccagaaccc                                                 19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctggagtctc ccaggaccc                                                 19

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctggagtcac tcaaactcca agatatct                                       28

<210> SEQ ID NO 17
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaaagccagt gaccctgagt tg                                               22

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cccagagctc gagatatcta gtcaa                                            25

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaaagccaag cagggatatc tgtc                                             24

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaaatacctg gtcacacaga tggga                                            25

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaaattccac gtcctgaaga cagg                                             24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aaaattccag gtcctgaaga cagg                                             24

<210> SEQ ID NO 23
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 23
aaaattccac atcctgaaga caggac                                          26

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aaagcacctg atcacagcaa ctg                                             23

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aacatccgag cagggttatc tgta                                            24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aacatccgag ctgggttatc tgta                                            24

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aacccaagat acctcatcac agtgac                                          26

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aagacacaga atcattggga cagg                                            24

<210> SEQ ID NO 29
<211> LENGTH: 24
<212> TYPE: DNA
<213> ORGANISM: Artificial Sequence
```

<220> FEATURE:
<223> OTHER INFORMATION: Description of Artificial Sequence: Synthetic primer

<400> SEQUENCE: 29
aagcatgagg tgacagaaat ggga                                    24

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
aaggcacaag gtgacagaga tg                                      22

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
aatacctggt cacacagatg ggaa                                    24

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
aattctcaag acacagaatc attgggaca                               29

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
acaaagtccc acacacctga tcaaa                                   25

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
acacaaggtc accaacatgg g                                       21

<210> SEQ ID NO 35
<211> LENGTH: 21
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 35
acaccaagac acctggtcat g                                           21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
accaacatct cagatcctgg ca                                          22

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
accagacccc aagataccit gttata                                      26

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
accccaagga ataggatcac aaaga                                       25

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acccccagta acaaggtcac a                                           21

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acctagactt ctggtcaaag caagtg                                      26

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 41
acctagattt ctggtcaaag caaatga                                         27

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
actccaggat atttggtcaa aggaaaagga a                                    31

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agacaccaaa acacctggtc atg                                             23

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agactattca tcaatggcca gcga                                            24

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agagcccaag atacaagatc acaga                                           25

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agccacagcg taatagagaa ggg                                             23

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aggacatttg gtcaaaggaa aaggac        26

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agtccccaag acatctgatc aaaga        25

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agtccctgag acacaaggta gca        23

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agtctcccag atataagatt atagagaaaa ggc        33

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
agtctcccag gtacaaagtc aca        23

<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
agtggttcag tctcccagat ataagattat ag        32

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 53
agtaacaagg tcacagagaa ggga                                              24

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
caaaattccg ggtcctgaag aca                                               23

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
caagacacct ggtcaggagg ag                                                22

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cagactccaa aacatcttgt cagagg                                            26

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cagccatcag gtcacacaga tg                                                22

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccaaggtaca aagtcgcaaa gagg                                              24

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
```
cccaaaattc cgcatcctga agata                                       25

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cccagtcccc cagatataag attaca                                      26

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccctaggtac aaagtcgcaa agaga                                       25

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgccatgagg tgacagagat gg                                          22

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cggcacgagg tgacagagat g                                           21

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gtcacccagg cacaaagtga ca                                          22

<210> SEQ ID NO 65
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
caagatatct gatcaaaacg agaggacag                                29

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccaagatatc tgatcaaaac gagaggac                                 28

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ctccaagata tctgatcaaa acgagagg                                 28

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gagaggacag caagtgacac tg                                       22

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gagtcactca aactccaaga tatctgatca                               30

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gctggagtca ctcaaactcc aag                                      23

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggagtcactc aaactccaag atatctgat                                29

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ggctggagtc actcaaactc c                                            21

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
catggtcatc cagaacccaa gatac                                        25

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ccatggtcat ccagaaccca ag                                           22

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gatgccatgg tcatccagaa cc                                           22

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggaaagccag tgaccctgag                                              20

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ggttacccag tttggaaagc ca                                           22

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gtttggaaag ccagtgaccc t                                        21

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gttacccagt tggaaagcc agt                                       23

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tgccatggtc atccagaacc                                          20

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ttacccagtt tggaaagcca gtg                                      23

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tttggaaagc cagtgaccct g                                        21

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
agagctcgag atatctagtc aaaaggac                                 28

```
<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
agctcgagat atctagtcaa aaggacg                                        27

<210> SEQ ID NO 85
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cgagatatct agtcaaaagg acggga                                         26

<210> SEQ ID NO 86
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gaaagtaacc cagagctcga gatatctag                                      29

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gatgtgaaag taacccagag ctcg                                           24

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gtaacccaga gctcgagata tctagtc                                        27

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gtgaaagtaa cccagagctc gag                                            23

<210> SEQ ID NO 90
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 90
aaaauacctg gucacacaga cggga                                          25

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 91
aagataccgg gutacccagt tugga                                          25

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 92
actcaaacuc caagacatct gaucaaaacg                                     30

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 93
agaaucccag acacaagatc acaaa                                          25

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 94
agaguccaag acacaagatc acaga                                          25
```

```
<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 95
agtccccaag acauctgauc agaga                                           25

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 96
atcaauggcc agcgacccug g                                               21

<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 97
ccaaaguccc acacacctga ucaaa                                           25

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 98
cccagacacc aaaauaccug g                                               21

<210> SEQ ID NO 99
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 99
ctcaacatcc gaguagggtt atctgua                                         27

<210> SEQ ID NO 100
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 100
ctcagucccc aaagtaccug t                                           21

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 101
cuggaaucac ccagagccc                                              19

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 102
cuggagtcuc ccacaaccc                                              19

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 103
cuggagtcuc ccagaaccc                                              19

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 104
cuggagtcuc ccaggaccc                                              19

<210> SEQ ID NO 105
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 105
ctggagtcac ucaaactcca agatauct                                           28

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 106
gaaagccagu gaccctgagt ug                                                 22

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 107
cccagagcuc gagatatcta gucaa                                              25

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 108
aaaagccaag cagggauatc tguc                                               24

<210> SEQ ID NO 109
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 109
aaaatacctg gucacacaga uggga                                              25

<210> SEQ ID NO 110
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 110
aaaatuccac gtccugaaga cagg                                            24

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 111
aaaatuccag gtccugaaga cagg                                            24

<210> SEQ ID NO 112
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 112
aaaautccac atccugaaga caggac                                          26

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 113
aaagcacctg aucacagcaa cug                                             23

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 114
aacatccgag cagggutatc tgua                                            24

<210> SEQ ID NO 115
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 115
aacatccgag cugggttatc tgua                                           24

<210> SEQ ID NO 116
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 116
aacccaagau acctcatcac agugac                                         26

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 117
aagacacaga aucatuggga cagg                                           24

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 118
aagcatgagg ugacagaaau ggga                                           24

<210> SEQ ID NO 119
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 119
aaggcacaag gugacagaga ug                                             22

<210> SEQ ID NO 120
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 120
aatacctggu cacacagaug ggaa                                           24

<210> SEQ ID NO 121
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 121
aattcucaag acacagaatc atugggaca                                      29

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 122 acaaguccc acacacctga ucaaa                                           25

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 123
acacaagguc accaacaugg g                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 124
acaccaagac accuggtcau g                                              21

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer
<220> FEATURE:
<223> OTHER INFORMATION: Description of Combined DNA/RNA Molecule:
      Synthetic primer

<400> SEQUENCE: 125
accaacatcu cagatccugg ca                                              22

<210> SEQ ID NO 126
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 126
accagacccc aagauacctt gttaua                                          26

<210> SEQ ID NO 127
<211> LENGTH: 25
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 127 acccccaagga auaggaucac aaaga                                          25

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 128
acccccagua acaaggucac a                                               21

<210> SEQ ID NO 129
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 129
acctagactt cuggtcaaag caagug                                          26

<210> SEQ ID NO 130
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

```
<400> SEQUENCE: 130
acctagattt cuggtcaaag caaauga                                         27

<210> SEQ ID NO 131
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 131
acuccaggat atttggucaa aggaaaagga a                                    31

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 132
agacaccaaa acaccuggtc aug                                             23

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 133
agacuattca tcaauggcca gcga                                            24

<210> SEQ ID NO 134
<211> LENGTH: 25
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 134
agagcccaag auacaagauc acaga                                           25

<210> SEQ ID NO 135
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 135
agccacagcg uaauagagaa ggg                                             23
```

```
<210> SEQ ID NO 136
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 136
aggacauttg gucaaaggaa aaggac                                          26

<210> SEQ ID NO 137
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 137
agtccccaag acauctgauc aaaga                                           25

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 138
agtcccugag acacaaggua gca                                             23

<210> SEQ ID NO 139
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 139
agtctcccag auataagatt auagagaaaa ggc                                  33

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 140
agtctcccag guacaaaguc aca                                             23
```

<210> SEQ ID NO 141
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 141
agtggttcag tcucccagat ataagattau ag                                32

<210> SEQ ID NO 142
<211> LENGTH: 24
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 142
aguaacaagg ucacagagaa ggga                                         24

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 143
caaaatuccg ggtccugaag aca                                          23

<210> SEQ ID NO 144
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 144
caagacaccu ggucaggagg ag                                           22

<210> SEQ ID NO 145
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 145
cagacuccaa aacatcttgu cagagg                                       26

<210> SEQ ID NO 146
<211> LENGTH: 22
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 146
cagccatcag gucacacaga ug                                          22

<210> SEQ ID NO 147
<211> LENGTH: 24
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 147
ccaagguaca aagucgcaaa gagg                                        24

<210> SEQ ID NO 148
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 148
cccaaaattc cgcauccuga agaua                                       25

<210> SEQ ID NO 149
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 149 cccaguccc cagatataag atuaca                                       26

<210> SEQ ID NO 150
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 150
cccuaggtac aaagucgcaa agaga                                       25

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer
<220> FEATURE:
<223> OTHER INFORMATION: Description of Combined DNA/RNA Molecule:
      Synthetic primer

<400> SEQUENCE: 151
cgccatgagg ugacagagau gg                                              22

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 152
cggcacgagg ugacagagau g                                               21

<210> SEQ ID NO 153
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 153
gucacccagg cacaaaguga ca                                              22

<210> SEQ ID NO 154
<211> LENGTH: 25
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 154
agaguccaag acacaagauc acaga                                           25

<210> SEQ ID NO 155
<211> LENGTH: 25
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 155
agaaucccag acacaagauc acaaa                                           25

<210> SEQ ID NO 156
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 156
cuccaagata tctgaucaaa acgagagg                                        28

<210> SEQ ID NO 157

```
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 157
gagaggacag caagugacac ug                                            22

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 158
gagtcactca aacuccaaga tatctgauca                                    30

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 159
gctggaguca ctcaaacucc aag                                           23

<210> SEQ ID NO 160
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 160
ggagtcactc aaacuccaag atatcugat                                     29

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 161
ggctggaguc actcaaacuc c                                             21

<210> SEQ ID NO 162
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 162
catggtcauc cagaacccaa gauac                                        25

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 163
ccauggtcau ccagaaccca ag                                           22

<210> SEQ ID NO 164
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 164
gatgccaugg tcauccagaa cc                                           22

<210> SEQ ID NO 165
<211> LENGTH: 20
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 165
ggaaagccag ugacccugag                                              20

<210> SEQ ID NO 166
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 166
ggutacccag ttuggaaagc ca                                           22

<210> SEQ ID NO 167
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 167
gttuggaaag ccagugaccc t                                              21

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 168
gutacccagt tuggaaagcc agt                                            23

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 169
tgccauggtc auccagaacc                                                20

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 170
ttacccagtt uggaaagcca gug                                            23

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 171
tttggaaagc cagugacccu g                                              21

<210> SEQ ID NO 172
<211> LENGTH: 28
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 172
agagcucgag atatctaguc aaaaggac                                       28

<210> SEQ ID NO 173
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 173
agctcgagau atctagucaa aaggacg                                        27

<210> SEQ ID NO 174
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 174
cgagauatct agucaaaagg acggga                                         26

<210> SEQ ID NO 175
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 175
gaaagtaacc cagagcucga gatatcuag                                      29

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 176
gatgtgaaag uaacccagag cucg                                           24

<210> SEQ ID NO 177
<211> LENGTH: 27
<212> TYPE: DNA
```

<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 177
gtaacccaga gcucgagata tctaguc                                          27

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 178
gtgaaaguaa cccagagcuc gag                                              23

<210> SEQ ID NO 179
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 179
caagauatct gaucaaaacg agaggacag                                        29

<210> SEQ ID NO 180
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 180
ccaagauatc tgaucaaaac gagaggac                                         28

<210> SEQ ID NO 181
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181 aattggt                                                                 7

<210> SEQ ID NO 182
<211> LENGTH: 7
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 182 aaatggt                                                                    7

<210> SEQ ID NO 183
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
aaaatttggt                                                                10

<210> SEQ ID NO 184
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
aaaattttta tccccccccg gg                                                  22

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
aatcttcaca tcaattccct ggag                                                24

<210> SEQ ID NO 186
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
acatccgctc accaggc                                                        17

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
acctacacac cctgcagc                                                       18

<210> SEQ ID NO 188
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 188
aggctggagt cagctgc                                                   17

<210> SEQ ID NO 189
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
aggtgcagcc tgcagaa                                                   17

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
atgaatgtga gcaccttgga g                                              21

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
atgaatgtga gtgccttgga g                                              21

<210> SEQ ID NO 192
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
caagctggag tcagctgc                                                  18

<210> SEQ ID NO 193
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
catgagctcc ttggagctg                                                 19

<210> SEQ ID NO 194
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
cattctgagt tctaagaagc tcctc                                        25

<210> SEQ ID NO 195
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
cctgaccctg aagtctgct                                               19

<210> SEQ ID NO 196
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
cctgagctct ctggagctg                                               19

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
ctagacatcc gctcaccagg c                                            21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
ctcaagatcc agcctgcaaa g                                            21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
ctcaagatcc agcctgcaga g                                            21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 200
ctcacgttgg cgtctgctgt a                                              21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
ctcactctgg agtcagctac c                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
ctcactctgg agtccgctac c                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ctcactctgg agtctgctgc c                                              21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
ctcactgtga catcggccca a                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
ctgaagatcc agccctcaga a                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
```
ctgaagatcc agcctgcaga g       21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
ctgaagatcc ggtccacaaa g       21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ctgaatgtga acgccttgtt g       21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
ctgaatgtga acgccttgga g       21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
ctgacagtga ccagtgccca t       21

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
ctgacagtga cctgtgccca t       21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
ctgaccctga agtctgccag c                                    21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
ctgactgtga gcaacatgag c                                    21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
ctgaggatcc agcaggtagt g                                    21

<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
ctgaggatcc agcccatgga a                                    21

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
ctgaggatcc agccctcaga a                                    21

<210> SEQ ID NO 217
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
ctggcaatcc tgtcctcaga a                                    21

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
ctggcaatcc tgtcctcgga a                                    21

```
<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
ctgtccctag agtctgccat c                                          21

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
ctcaagatcc agccagcaga g                                          21

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
ctgaagatcc atcccgcaga g                                          21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
ctgaagatcc agcgcacaca g                                          21

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
ctgaagatcc agcgcacaga g                                          21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
ctgaagttcc agcgcacaca g                                          21
```

-continued

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
ctgacgattc agcgcacaga g                                              21

<210> SEQ ID NO 226
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
ctgacgatcc agcgcaca                                                  18

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
ctgactgtga gcaacaggag a                                              21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
ctgattctgg agtccgccag c                                              21

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
gccttgagat ccaggctacg                                                20

<210> SEQ ID NO 230
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
ggctggagtt ggctgct                                                   17

```
<210> SEQ ID NO 231
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
ggttggagtc ggctgct                                                   17

<210> SEQ ID NO 232
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
tcacctacac gccctgc                                                   17

<210> SEQ ID NO 233
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
tcaggctgct gtcggct                                                   17

<210> SEQ ID NO 234
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
tcaggctgga gtcggct                                                   17

<210> SEQ ID NO 235
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tcaggctggt gtcggct                                                   17

<210> SEQ ID NO 236
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
tcatcctgag ttctaagaag ctcc                                           24

<210> SEQ ID NO 237
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tcctgagttc taagaagctc ctc                                              23

<210> SEQ ID NO 238
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
tctcaagatc caacctgcaa ag                                               22

<210> SEQ ID NO 239
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
tgaccctgga gtctgcc                                                     17

<210> SEQ ID NO 240
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
tgatcctgga gtcgccc                                                     17

<210> SEQ ID NO 241
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
tgtggtcgca ctgcagc                                                     17

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
ttggagatcc agtccacgga g                                                21

<210> SEQ ID NO 243
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
ttggagatcc agcgcacaga g                                              21

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
catgagctcc ttggagctgg                                                20

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
aacatgagct ccttggagct g                                              21

<210> SEQ ID NO 246
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
gaacatgagc tccttggagc tg                                             22

<210> SEQ ID NO 247
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
tgaactgaac atgagctcct tgg                                            23

<210> SEQ ID NO 248
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
ctgaactgaa catgagctcc ttgg                                           24

<210> SEQ ID NO 249
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 249
aatcttcaca ucaattcccu ggag                                          24

<210> SEQ ID NO 250
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 250
acauccgcuc accaggc                                                  17

<210> SEQ ID NO 251
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 251
accuacacac ccugcagc                                                 18

<210> SEQ ID NO 252
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 252
aggcuggagt cagcugc                                                  17

<210> SEQ ID NO 253
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 253
aggugcagcc ugcagaa                                                  17

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
```

```
<400> SEQUENCE: 254
atgaatguga gcacctugga g                                              21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 255
atgaatguga gtgcctugga g                                              21

<210> SEQ ID NO 256
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 256
caagcuggag tcagcugc                                                  18

<210> SEQ ID NO 257
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 257
catgagcucc ttggagcug                                                 19

<210> SEQ ID NO 258
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
       Synthetic primer

<400> SEQUENCE: 258
cattctgagt tcuaagaagc tccuc                                          25

<210> SEQ ID NO 259
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
```

-continued

<400> SEQUENCE: 259
cctgacccug aagtcugct                                                    19

<210> SEQ ID NO 260
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 260
cctgagcuct ctggagcug                                                    19

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 261
ctagacaucc gcucaccagg c                                                 21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 262
ctcaagaucc agccugcaaa g                                                 21

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 263
ctcaagaucc agccugcaga g                                                 21

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:

Synthetic primer

<400> SEQUENCE: 264
ctcacgtugg cgtctgctgu a                                        21

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 265
ctcactcugg agtcagcuac c                                        21

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 266
ctcactcugg agtccgcuac c                                        21

<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 267
ctcactcugg agtctgcugc c                                        21

<210> SEQ ID NO 268
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 268
ctcacugtga caucggccca a                                        21

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:

```
<223> OTHER INFORMATION: Description of Combined DNA/RNA Molecule:
      Synthetic primer

<400> SEQUENCE: 269
ctgaagaucc agcccucaga a                                              21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 270
ctgaagaucc agccugcaga g                                              21

<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 271
ctgaagaucc gguccacaaa g                                              21

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 272
ctgaatguga acgccttgtu g                                              21

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 273
ctgaatguga acgcctugga g                                              21

<210> SEQ ID NO 274
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<223> OTHER INFORMATION: Description of Combined DNA/RNA Molecule:
      Synthetic primer

<400> SEQUENCE: 274
ctgacaguga ccagugccca t                                              21

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 275
ctgacaguga cctgugccca t                                              21

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 276
ctgacccuga agtcugccag c                                              21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 277
ctgactguga gcaacaugag c                                              21

<210> SEQ ID NO 278
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 278
ctgaggaucc agcaggtagu g                                              21

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued

```
      primer
<220> FEATURE:
<223> OTHER INFORMATION: Description of Combined DNA/RNA Molecule:
      Synthetic primer

<400> SEQUENCE: 279
ctgaggaucc agcccaugga a                                              21

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 280
ctgaggaucc agcccucaga a                                              21

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 281
ctggcaaucc tgtccucaga a                                              21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 282
ctggcaaucc tgtccucgga a                                              21

<210> SEQ ID NO 283
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 283
ctgtcccuag agtctgccau c                                              21

<210> SEQ ID NO 284
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      primer

<400> SEQUENCE: 284
cucaagaucc agccagcaga g                                           21

<210> SEQ ID NO 285
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 285
cugaagatcc aucccgcaga g                                           21

<210> SEQ ID NO 286
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 286
cugaagaucc agcgcacaca g                                           21

<210> SEQ ID NO 287
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 287
cugaagaucc agcgcacaga g                                           21

<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 288
cugaagtucc agcgcacaca g                                           21

<210> SEQ ID NO 289
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 289
``` cugacgauc agcgcacaga g                                              21

<210> SEQ ID NO 290
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 290
cugacgaucc agcgcaca                                                 18

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 291
cugactguga gcaacaggag a                                             21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 292
cugattctgg aguccgccag c                                             21

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 293
gccttgagau ccaggcuacg                                               20

<210> SEQ ID NO 294
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 294
ggctggagut ggcugct                                                  17

```
<210> SEQ ID NO 295
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 295
ggttggaguc ggcugct                                                  17

<210> SEQ ID NO 296
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 296
tcaccuacac gcccugc                                                  17

<210> SEQ ID NO 297
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 297
tcaggcugct gucggct                                                  17

<210> SEQ ID NO 298
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 298
tcaggcugga gucggct                                                  17

<210> SEQ ID NO 299
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 299
tcaggcuggt gucggct                                                  17
```

<210> SEQ ID NO 300
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 300
tcatcctgag utctaagaag cucc                                           24

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 301
tcctgagttc uaagaagctc cuc                                            23

<210> SEQ ID NO 302
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 302
tctcaagauc caaccugcaa ag                                             22

<210> SEQ ID NO 303
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 303
tgacccugga gtcugcc                                                   17

<210> SEQ ID NO 304
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 304
tgatccugga gucgccc                                                  17

<210> SEQ ID NO 305
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 305
tgtggucgca cugcagc                                                  17

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 306
ttggagaucc aguccacgga g                                             21

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 307
tuggagaucc agcgcacaga g                                             21

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 308
catgagcucc ttggagcugg                                               20

<210> SEQ ID NO 309
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 309
aacatgagcu ccttggagcu g                                          21

<210> SEQ ID NO 310
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 310
gaacatgagc uccttggagc ug                                         22

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 311
tgaactgaac augagctcct ugg                                        23

<210> SEQ ID NO 312
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 312
ctgaactgaa caugagctcc tugg                                       24

<210> SEQ ID NO 313
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
aaccaggagt cctccgc                                               17

<210> SEQ ID NO 314
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
acggtcagcc tagagcctt                                             19

<210> SEQ ID NO 315

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
agtctggtgc cttgtccaa                                                    19

<210> SEQ ID NO 316
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
cacggtcagc ctgctgc                                                      17

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
cccatcacca aaatgctggg                                                   20

<210> SEQ ID NO 318
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
cctgggccaa aatactgcg                                                    19

<210> SEQ ID NO 319
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
cggcccgaag tactgct                                                      17

<210> SEQ ID NO 320
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
cggcgccgaa gtactga                                                      17

<210> SEQ ID NO 321
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
ctggcccgaa gaactgc                                                    17

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
gagccaactt ccctctccaa                                                 20

<210> SEQ ID NO 323
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
gcctggtccc attcccaaa                                                  19

<210> SEQ ID NO 324
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
gctgggttcc actgccaaa                                                  19

<210> SEQ ID NO 325
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
tcccgttccc aaagtggag                                                  19

<210> SEQ ID NO 326
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
tgaccgtgag cctggtg                                                    17

<210> SEQ ID NO 327
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 327
tggcccgaag tactggg                                                    17

<210> SEQ ID NO 328
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
ttaacctggt ccccgaacc                                                  19

<210> SEQ ID NO 329
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
gaccgtgagc ctggtgc                                                    17

<210> SEQ ID NO 330
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
caggagccgc gtgcctg                                                    17

<210> SEQ ID NO 331
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
agcactgtca gccgggt                                                    17

<210> SEQ ID NO 332
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
ccagcacggt cagcctg                                                    17

<210> SEQ ID NO 333
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 333
ctagcacggt gagccgt                                                    17

<210> SEQ ID NO 334
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
agcactgaga gccgggtc                                                   18

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
cagtacggtc agcctagagc                                                 20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
ccagaaccag gagtcctccg                                                 20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
ctgtcacagt gagcctggtc                                                 20

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
ccaagacaga gagctgggtt c                                               21

<210> SEQ ID NO 339
<211> LENGTH: 22
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 339
ctacaactgt gagtctggtg cc                                              22

<210> SEQ ID NO 340
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
ctaggatgga gagtcgagtc cc                                              22

<210> SEQ ID NO 341
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
ctacaacggt taacctggtc cc                                              22

<210> SEQ ID NO 342
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
ctacaacagt gagccaactt ccc                                             23

<210> SEQ ID NO 343
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
gtgaccgtga gcctggt                                                    17

<210> SEQ ID NO 344
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
tgtgaccgtg agcctgg                                                    17

<210> SEQ ID NO 345
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 345
gtgaccgtga gcctggtg                                                 18

<210> SEQ ID NO 346
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
tgtgaccgtg agcctggt                                                 18

<210> SEQ ID NO 347
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
ctgtgaccgt gagcctgg                                                 18

<210> SEQ ID NO 348
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
caggagtcct ccgccca                                                  17

<210> SEQ ID NO 349
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
accaggagtc ctccgcc                                                  17

<210> SEQ ID NO 350
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
actgagagcc gggtccc                                                  17

<210> SEQ ID NO 351
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
cactgagagc cgggtcc                                                  17

<210> SEQ ID NO 352
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
gcactgagag ccgggtc                                                  17

<210> SEQ ID NO 353
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
gcacggtcag cctgctg                                                  17

<210> SEQ ID NO 354
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
cagcacggtc agcctgc                                                  17

<210> SEQ ID NO 355
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
tagcacggtg agccgtg                                                  17

<210> SEQ ID NO 356
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
ccaggagccg cgtgcctg                                                 18

<210> SEQ ID NO 357
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 357
aaccaggagt cctccgcc                                                      18

<210> SEQ ID NO 358
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
gaaccaggag tcctccgc                                                      18

<210> SEQ ID NO 359
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
tagcacggtg agccgtgt                                                      18

<210> SEQ ID NO 360
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
accaggagcc gcgtgcctg                                                     19

<210> SEQ ID NO 361
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
aacggttaac ctggtcccc                                                     19

<210> SEQ ID NO 362
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
agaaccagga gtcctccgc                                                     19

<210> SEQ ID NO 363
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 363
```
cagaaccagg agtcctccg                                                19

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
tacggtcagc ctagagcctt                                               20

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
gtacggtcag cctagagcct                                               20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
ggatggagag tcgagtccca                                               20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
caacggttaa cctggtcccc                                               20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
agtacggtca gcctagagcc                                               20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
aggatggaga gtcgagtccc                                               20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
acaacggtta acctggtccc                                               20

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
tgtcacagtg agcctggtcc                                               20

<210> SEQ ID NO 372
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
caactgtgag tctggtgcct t                                             21

<210> SEQ ID NO 373
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
gtacggtcag cctagagcct t                                             21

<210> SEQ ID NO 374
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
ggatggagag tcgagtccca t                                             21

<210> SEQ ID NO 375
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
acaactgtga gtctggtgcc t                                             21

<210> SEQ ID NO 376
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
agtacggtca gcctagagcc t                                          21

<210> SEQ ID NO 377
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
aggatggaga gtcgagtccc a                                          21

<210> SEQ ID NO 378
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
tacaactgtg agtctggtgc c                                          21

<210> SEQ ID NO 379
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
caagacagag agctgggttc c                                          21

<210> SEQ ID NO 380
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
taggatggag agtcgagtcc c                                          21

<210> SEQ ID NO 381
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
tacaacggtt aacctggtcc c                                          21

<210> SEQ ID NO 382
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 382
acaactgtga gtctggtgcc tt                                            22

<210> SEQ ID NO 383
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 383
aagacagaga gctgggttcc ac                                            22

<210> SEQ ID NO 384
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 384
aggatggaga gtcgagtccc at                                            22

<210> SEQ ID NO 385
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 385
acaacagtga gccaacttcc ct                                            22

<210> SEQ ID NO 386
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 386
tacaactgtg agtctggtgc ct                                            22

<210> SEQ ID NO 387
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 387
caagacagag agctgggttc ca                                            22

```
<210> SEQ ID NO 388
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
taggatggag agtcgagtcc ca                                              22

<210> SEQ ID NO 389
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
tacaacggtt aacctggtcc cc                                              22

<210> SEQ ID NO 390
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 390
tacaactgtg agtctggtgc ctt                                             23

<210> SEQ ID NO 391
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
taggatggag agtcgagtcc cat                                             23

<210> SEQ ID NO 392
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
tacaacagtg agccaacttc cct                                             23

<210> SEQ ID NO 393
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
ctacaactgt gagtctggtg cct                                             23

<210> SEQ ID NO 394
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
ctaggatgga gagtcgagtc cca                                          23

<210> SEQ ID NO 395
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
ctacaactgt gagtctggtg cctt                                         24

<210> SEQ ID NO 396
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
ctaggatgga gagtcgagtc ccat                                         24

<210> SEQ ID NO 397
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
ctacaacagt gagccaactt ccct                                         24

<210> SEQ ID NO 398
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 398
aaccaggagu ccuccgc                                                 17

<210> SEQ ID NO 399
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 399
acggtcagcc uagagccut                                               19
```

<210> SEQ ID NO 400
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 400
agtctggugc cttguccaa                                                 19

<210> SEQ ID NO 401
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 401
cacggucagc ctgcugc                                                   17

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 402
cccaucacca aaatgcuggg                                                20

<210> SEQ ID NO 403
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 403
ccugggccaa aatacugcg                                                 19

<210> SEQ ID NO 404
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 404
cggcccgaag uacugct                                                   17

```
<210> SEQ ID NO 405
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 405
cggcgccgaa guacuga                                                        17

<210> SEQ ID NO 406
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 406
cuggcccgaa gaacugc                                                        17

<210> SEQ ID NO 407
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 407
gagccaacut ccctcuccaa                                                     20

<210> SEQ ID NO 408
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 408
gcctgguccc atucccaaa                                                      19

<210> SEQ ID NO 409
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 409
gctgggutcc acugccaaa                                                      19

<210> SEQ ID NO 410
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 410
tcccgtuccc aaaguggag                                                19

<210> SEQ ID NO 411
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 411
tgaccgugag cctggug                                                  17

<210> SEQ ID NO 412
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 412
tggcccgaag uacuggg                                                  17

<210> SEQ ID NO 413
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 413
tuaacctggu ccccgaacc                                                19

<210> SEQ ID NO 414
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 414
gaccgugagc ctggugc                                                  17

<210> SEQ ID NO 415
<211> LENGTH: 17
```

-continued

```
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 415
caggagccgc gugccug                                                17

<210> SEQ ID NO 416
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 416
agcacuguca gccgggt                                                17

<210> SEQ ID NO 417
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 417
ccagcacggu cagccug                                                17

<210> SEQ ID NO 418
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 418
cuagcacggu gagccgt                                                17

<210> SEQ ID NO 419
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 419
agcacugaga gccggguc                                               18

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
```

```
<400> SEQUENCE: 420
cagtacgguc agccuagagc                                                  20

<210> SEQ ID NO 421
<211> LENGTH: 20
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 421
ccagaaccag gaguccuccg                                                  20

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 422
ctgtcacagu gagcctgguc                                                  20

<210> SEQ ID NO 423
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 423
ccaagacaga gagcugggtu c                                                21

<210> SEQ ID NO 424
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 424
ctacaactgu gagtctggug cc                                               22

<210> SEQ ID NO 425
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 425
```

```
ctaggaugga gagtcgaguc cc                                        22

<210> SEQ ID NO 426
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 426
ctacaacggu uaacctgguc cc                                        22

<210> SEQ ID NO 427
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 427
ctacaacagu gagccaactu ccc                                       23

<210> SEQ ID NO 428
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 428
gtgaccguga gccuggt                                              17

<210> SEQ ID NO 429
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 429
tgtgaccgug agccugg                                              17

<210> SEQ ID NO 430
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
```

```
<400> SEQUENCE: 430
gtgaccguga gcctggug                                                 18

<210> SEQ ID NO 431
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 431
tgtgaccgug agccuggt                                                 18

<210> SEQ ID NO 432
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 432
ctgtgaccgu gagccugg                                                 18

<210> SEQ ID NO 433
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 433
caggaguccu ccgccca                                                  17

<210> SEQ ID NO 434
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 434
accaggaguc cuccgcc                                                  17

<210> SEQ ID NO 435
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 435
acugagagcc gggucccc                                                 17

<210> SEQ ID NO 436
<211> LENGTH: 17
<212> TYPE: RNA
```

```
<213> ORGANISM: Artificial Sequence
<220> FEATURE:
<223> OTHER INFORMATION: Description of Artificial Sequence: Synthetic
      primer

<400> SEQUENCE: 436
cacugagagc cgggucc                                                    17

<210> SEQ ID NO 437
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 437
gcacugagag ccggguc                                                    17

<210> SEQ ID NO 438
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 438
gcacggucag cctgcug                                                    17

<210> SEQ ID NO 439
<211> LENGTH: 17
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 439
cagcacgguc agccugc                                                    17

<210> SEQ ID NO 440
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 440
tagcacggug agccgug                                                    17

<210> SEQ ID NO 441
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 441
ccaggagccg cgugccug                                                   18
```

<210> SEQ ID NO 442
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 442
aaccaggagu ccuccgcc                                                   18

<210> SEQ ID NO 443
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 443
gaaccaggag uccuccgc                                                   18

<210> SEQ ID NO 444
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 444
tagcacggug agccgugt                                                   18

<210> SEQ ID NO 445
<211> LENGTH: 19
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 445
accaggagcc gcgugccug                                                  19

<210> SEQ ID NO 446
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 446
aacggtuaac ctgguccccc                                                 19

<210> SEQ ID NO 447
<211> LENGTH: 19
<212> TYPE: RNA
<213> ORGANISM: Artificial Sequence
<220> FEATURE:
<223> OTHER INFORMATION: Description of Artificial Sequence: Synthetic primer

<400> SEQUENCE: 447
agaaccagga guccuccgc                                                        19

<210> SEQ ID NO 448
<211> LENGTH: 19
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 448
cagaaccagg aguccuccg                                                        19

<210> SEQ ID NO 449
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 449
tacggtcagc cuagagccut                                                       20

<210> SEQ ID NO 450
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 450
gtacggucag ccuagagcct                                                       20

<210> SEQ ID NO 451
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 451
ggatggagag ucgaguccca                                                       20

<210> SEQ ID NO 452
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

```
<400> SEQUENCE: 452
caacggtuaa cctgguccccc                                              20

<210> SEQ ID NO 453
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 453
agtacgguca gccuagagcc                                               20

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 454
aggatggaga gucgaguccc                                               20

<210> SEQ ID NO 455
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 455
acaacgguta acctgguccc                                               20

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 456
tgtcacagug agcctgguccc                                              20

<210> SEQ ID NO 457
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
```

<400> SEQUENCE: 457
caactgtgag uctggtgccu t                                              21

<210> SEQ ID NO 458
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 458
gtacggucag cctagagccu t                                              21

<210> SEQ ID NO 459
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 459
ggatggagag ucgaguccca t                                              21

<210> SEQ ID NO 460
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 460
acaactguga gtctggugcc t                                              21

<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 461
agtacgguca gccuagagcc t                                              21

<210> SEQ ID NO 462
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:

Synthetic primer

<400> SEQUENCE: 462
aggatggaga gucgagucccc a                                               21

<210> SEQ ID NO 463
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 463
tacaactgug agtctggugc c                                                21

<210> SEQ ID NO 464
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 464
caagacagag agcugggtuc c                                                21

<210> SEQ ID NO 465
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 465
taggauggag agtcgagucc c                                                21

<210> SEQ ID NO 466
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 466
tacaacggut aacctggucc c                                                21

<210> SEQ ID NO 467
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:

```
<223> OTHER INFORMATION: Description of Combined DNA/RNA Molecule:
      Synthetic primer

<400> SEQUENCE: 467
acaactgtga guctggtgcc ut                                              22

<210> SEQ ID NO 468
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 468
aagacagaga gcugggtucc ac                                              22

<210> SEQ ID NO 469
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 469
aggatggaga gucgaguccc at                                              22

<210> SEQ ID NO 470
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 470
acaacaguga gccaactucc ct                                              22

<210> SEQ ID NO 471
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 471
tacaactgug agtctggugc ct                                              22

<210> SEQ ID NO 472
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<220> FEATURE:
<223> OTHER INFORMATION: Description of Combined DNA/RNA Molecule:
   Synthetic primer

<400> SEQUENCE: 472
caagacagag agcugggtuc ca                                              22

<210> SEQ ID NO 473
<211> LENGTH: 22
<212> TYPE: DNA
<213> ORGANISM: Artificial Sequence
<220> FEATURE:
<223> OTHER INFORMATION: Description of Artificial Sequence: Synthetic
   primer
<220> FEATURE:
<223> OTHER INFORMATION: Description of Combined DNA/RNA Molecule:
   Synthetic primer

<400> SEQUENCE: 473
taggauggag agtcgagucc ca                                              22

<210> SEQ ID NO 474
<211> LENGTH: 22
<212> TYPE: DNA
<213> ORGANISM: Artificial Sequence
<220> FEATURE:
<223> OTHER INFORMATION: Description of Artificial Sequence: Synthetic
   primer
<220> FEATURE:
<223> OTHER INFORMATION: Description of Combined DNA/RNA Molecule:
   Synthetic primer

<400> SEQUENCE: 474
tacaacggut aacctggucc cc                                              22

<210> SEQ ID NO 475
<211> LENGTH: 23
<212> TYPE: DNA
<213> ORGANISM: Artificial Sequence
<220> FEATURE:
<223> OTHER INFORMATION: Description of Artificial Sequence: Synthetic
   primer
<220> FEATURE:
<223> OTHER INFORMATION: Description of Combined DNA/RNA Molecule:
   Synthetic primer

<400> SEQUENCE: 475
tacaactgtg aguctggtgc cut                                             23

<210> SEQ ID NO 476
<211> LENGTH: 23
<212> TYPE: DNA
<213> ORGANISM: Artificial Sequence
<220> FEATURE:
<223> OTHER INFORMATION: Description of Artificial Sequence: Synthetic
   primer
<220> FEATURE:
<223> OTHER INFORMATION: Description of Combined DNA/RNA Molecule:
   Synthetic primer

<400> SEQUENCE: 476
taggauggag agtcgagucc cat                                             23

<210> SEQ ID NO 477
<211> LENGTH: 23
<212> TYPE: DNA
<213> ORGANISM: Artificial Sequence
<220> FEATURE:
<223> OTHER INFORMATION: Description of Artificial Sequence: Synthetic

```
      primer
<220> FEATURE:
<223> OTHER INFORMATION: Description of Combined DNA/RNA Molecule:
      Synthetic primer

<400> SEQUENCE: 477
tacaacagug agccaactuc cct                                          23

<210> SEQ ID NO 478
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 478
ctacaactgu gagtctggug cct                                          23

<210> SEQ ID NO 479
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 479
ctaggaugga gagtcgaguc cca                                          23

<210> SEQ ID NO 480
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 480
ctacaactgt gaguctggtg ccut                                         24

<210> SEQ ID NO 481
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 481
ctaggaugga gagtcgaguc ccat                                         24

<210> SEQ ID NO 482
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 482
ctacaacagu gagccaactu ccct                                          24

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 483
aactatgttt tggtatcgtc a                                             21

<210> SEQ ID NO 484
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 484
cacgatgttc tggtaccgtc agca                                          24

<210> SEQ ID NO 485
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 485
cagtgtgtcc tggtaccaac ag                                            22

<210> SEQ ID NO 486
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 486 aacccttat tggtaccgac a                                              21

<210> SEQ ID NO 487
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 487 atccctttt tggtaccaac ag                                             22

<210> SEQ ID NO 488
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 488
aaccctttat tggtatcaac ag                                              22

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 489
cgctatgtat tggtacaagc a                                               21

<210> SEQ ID NO 490
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 490
ctcccgtttt ctggtacaga cagac                                           25

<210> SEQ ID NO 491
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 491
cgctatgtat tggtataaac ag                                              22

<210> SEQ ID NO 492
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 492
ttatgtttac tggtatcgta agaagc                                          26

<210> SEQ ID NO 493
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 493
caaaatgtac tggtatcaac aa                                              22

<210> SEQ ID NO 494
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 494
atacatgtac tggtatcgac aagac                                           25

<210> SEQ ID NO 495
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 495
ggccatgtac tggtatagac aag                                             23

<210> SEQ ID NO 496
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 496
gtatatgtcc tggtatcgac aaga                                            24

<210> SEQ ID NO 497
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 497
taacctttat tggtatcgac gtgt                                            24

<210> SEQ ID NO 498
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 498
ggccatgtac tggtaccgac a                                               21

<210> SEQ ID NO 499
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 499
tcatgtttac tggtatcggc ag                                              22

<210> SEQ ID NO 500
<211> LENGTH: 27
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 500
ttatgtttat tggtatcaac agaatca                                            27

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 501
caacctatac tggtaccgac a                                                  21

<210> SEQ ID NO 502
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 502
taccctttac tggtaccggc ag                                                 22

<210> SEQ ID NO 503
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 503
atacttctat tggtacagac aaatct                                             26

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 504
cacggtctac tggtaccagc a                                                  21

<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 505
cgtcatgtac tggtaccagc a                                                  21
```

COMPOSITIONS AND METHODS FOR IMMUNE REPERTOIRE SEQUENCING

CROSS-REFERENCE TO RELATED APPLICATIONS

This application claims priority to and the benefit of U.S. Provisional Application No. 62/586,129 filed Nov. 14, 2017 and U.S. Provisional Application No. 62/553,688 filed Sep. 1, 2017. The entire contents of each of the aforementioned applications are incorporated herein by reference.

SEQUENCE LISTING

The instant application contains a Sequence Listing which has been submitted electronically in ASCII format and is hereby incorporated by reference in its entirety. Said ASCII copy, created on Nov. 12, 2018, is named LT01286_SL.txt and is 131,447 bytes in size.

BACKGROUND

Adaptive immune response comprises selective response of B and T cells recognizing antigens. The immunoglobulin genes encoding antibody (Ab, in B cell) and T-cell receptor (TCR, in T cell) antigen receptors comprise complex loci wherein extensive diversity of receptors is produced as a result of recombination of the respective variable (V), diversity (D), and joining (J) gene segments, as well as subsequent somatic hypermutation events during early lymphoid differentiation. The recombination process occurs separately for both subunit chains of each receptor and subsequent heterodimeric pairing creates still greater combinatorial diversity. Calculations of the potential combinatorial and junctional possibilities that contribute to the human immune receptor repertoire have estimated that the number of possibilities greatly exceeds the total number of peripheral B or T cells in an individual. See, for example, Davis et al. (1988) Nature 334:395-402; Arstila et al. (1999) Science 286:958-961; van Dongen et al., In: Leukemia, Henderson et al. (eds) Philadelphia: WB Saunders Co., 2002, pp 85-129.

Extensive efforts have been made over years to improve analysis of the immune repertoire at high resolution. Means for specific detection and monitoring of expanded clones of lymphocytes would provide significant opportunities for characterization and analysis of normal and pathogenic immune reactions and responses. Despite efforts, effective high-resolution analysis has provided challenges. Low throughput techniques such as Sanger sequencing may provide resolution, but are limited to provide an efficient means to broadly capture the entire immune repertoire. Recent advances in next generation sequencing (NGS) have provided access to capturing the repertoire, however, due to the nature of the numerous related sequences and introduction of sequence errors as a result of the technology, efficient and effective reflection of the true repertoire has proven difficult. Thus, new methods for effective profiling of vast repertoires of immune cell receptors are increasingly sought to better understand immune cell response, enhance diagnostic capabilities, and devise new therapeutics. Accordingly, there remains a need for improved sequencing methodologies and workflows capable of resolving complex populations of highly variable immune cell receptor sequences.

SUMMARY OF THE INVENTION

In one aspect of the invention, methods are provided for single stream determining of immune repertoire activity in a biological sample. Such methods comprise performing multiplex amplification of a plurality of target immune receptor genomic DNA sequences having rearranged V(D)J genes from a biological sample containing target immune cell receptor genomic DNA. In some embodiments, amplification comprises contacting at least a portion of the genomic DNA sample comprising multiple target sequences of interest using at least one set of primers comprising i) and ii), wherein i) comprises a plurality of V gene target-specific primers directed to a majority of different V genes of at least one immune receptor coding sequence and ii) comprises a plurality of J gene primers directed to a majority of different J genes of the respective target immune receptor coding sequence. Each set of primers i) and ii) is directed to the same target immune receptor coding sequence wherein each target immune receptor is selected from a T cell receptor or an antibody receptor sequence, and performing amplification using each one or more sets results in amplicon sequences representing the entire repertoire sequences of the respective immune receptor(s) in the sample of interest. In certain embodiments, methods comprise amplification of genomic DNA comprising rearranged V(D)J gene nucleic acid sequences of an immune receptor repertoire in a sample, the amplification comprising performing a multiplex amplification reaction in the presence of a polymerase under amplification conditions to produce a plurality of amplified target sequences comprising one or more immune receptors of interest having a rearranged variable, diversity, and joining (VDJ) gene segments or one or more immune receptors of interest having a rearranged variable and joining (VJ) gene segments.

In some embodiments, the method for amplification of rearranged genomic DNA sequences of an immune receptor repertoire in a sample comprises performing a single multiplex amplification reaction to amplify target immune receptor DNA template molecules having rearranged VDJ or VJ gene segments using at least one set of:
i) (a) a plurality of V gene primers directed to a majority of different V genes of at least one immune receptor coding sequence comprising at least a portion of framework region 3 (FR3) within the V gene,
   (b) a plurality of V gene primers directed to a majority of different V genes of at least one immune receptor coding sequence comprising at least a portion of framework region 2 (FR2) within the V gene, or
   (c) a plurality of V gene primers directed to a majority of different V genes of at least one immune receptor coding sequence comprising at least a portion of framework region 1 (FR1) within the V gene; and
ii) a plurality of J gene primers directed to at least a portion of a majority of different J genes of the at least one immune receptor coding sequence,
wherein each set of i) and ii) primers is directed to coding sequences of the same target immune receptor gene selected from a T cell receptor gene or an antibody receptor gene and wherein performing the amplification using the at least one set of i) and ii) primers results in amplicon molecules representing the target immune receptor repertoire in the sample; thereby generating immune receptor amplicon molecules comprising the target immune receptor repertoire.

In certain embodiments at least a portion of the third framework region (FR3) of the V gene to at least a portion of the joining (J) gene of the immune receptor sequence is encompassed within amplified target immune receptor sequences. In certain embodiments at least a portion of the second framework region (FR2) of the V gene to at least a portion of the joining (J) gene of the immune receptor sequence is encompassed within amplified target immune receptor sequences. In certain embodiments at least a portion of the first framework region (FR1) of the V gene to at least a portion of the joining (J) gene of the immune receptor sequence is encompassed within amplified target immune receptor sequences.

Provided methods further comprise preparing an immune receptor repertoire library using the amplified target immune receptor sequences through introducing adapter sequences to the termini of the amplified target sequences. In some embodiments, the adapter-modified immune receptor repertoire library is clonally amplified.

Provided methods further comprise detecting rearranged genomic DNA sequences of the immune repertoire of each of the target immune receptors in the sample, wherein a change in the repertoire sequence profile and/or diversity as compared with a second sample or a control sample determines a change in immune repertoire in the sample. In certain embodiments sequencing of the immune receptor amplicon molecules is carried out using next generation sequence analysis to determine sequence of the immune receptor amplicons. In particular embodiments determining the sequence of the immune receptor amplicon molecules includes obtaining initial sequence reads, inferring the J gene sequence, aligning and identifying productive reads, identifying and correcting V gene errors to generate rescued productive reads, and determining the sequences of the resulting total productive reads and the unproductive reads, thereby providing sequence of the immune repertoire in the sample. Provided methods described herein utilize compositions of the invention provided herein.

In other aspects of the invention, particular analysis methodology for error correction is provided in order to generate comprehensive, effective sequence information from methods provided herein.

In still other aspects of the invention compositions are provided for a single stream determination of an immune repertoire in a sample. In some embodiments the provided composition comprises at least one set of primers i) and ii), wherein i) consists of a plurality of variable (V) gene primers directed to a majority of different V genes of an immune receptor coding sequence; and ii) consists of a plurality of joining (J) gene primers directed to a majority of different J genes of the respective target immune receptor coding sequence. In some embodiments the V gene primers recognize at least a portion of framework region 3 (FR3) within the V gene. In some embodiments the V gene primers recognize at least a portion of framework region 2 (FR2) within the V gene. In some embodiments the V gene primers recognize at least a portion of framework region 1 (FR1) within the V gene. Each set of i) and ii) primers are directed to the same target immune receptor sequence selected from the group consisting of a T cell receptor and an antibody receptor, and configured such that resulting amplicons generated using such compositions represent the repertoire of sequences of the respective receptor in a sample. In particular embodiments, provided compositions include a plurality of primer pair reagents selected from Table 3 and Table 5. In other particular embodiments, provided compositions include a plurality of primer pair reagents selected from Table 4 and Table 5. In other particular embodiments, provided compositions include a plurality of primer pair reagents selected from Table 2 and Table 5. In some embodiments a multiplex assay comprising compositions of the invention is provided. In some embodiments a test kit comprising compositions of the invention is provided.

In some embodiments, the composition for multiplex amplification of an immune repertoire in a sample comprises: genomic DNA from a biological sample, a DNA polymerase, dNTPs, and at least one set of:
  i) (a) a plurality of V gene primers directed to a majority of different V genes of at least one immune receptor coding sequence comprising at least a portion of framework region 3 (FR3) within the V gene;
  (b) a plurality of V gene primers directed to a majority of different V genes of at least one immune receptor coding sequence comprising at least a portion of framework region 2 (FR2) within the V gene, or
  (c) a plurality of V gene primers directed to a majority of different V genes of at least one immune receptor coding sequence comprising at least a portion of framework region 1 (FR1) within the V gene; and
  ii) a plurality of J gene primers directed to at least a portion of a majority of different J genes of the at least one immune receptor coding sequence;
wherein each set of i) and ii) primers is directed to coding sequences of the same target immune receptor gene selected from a T cell receptor or an antibody receptor; and wherein each set of i) and ii) primers directed to the same target immune receptor is configured to amplify the target immune receptor repertoire.

DESCRIPTION OF THE INVENTION

Figure 1:
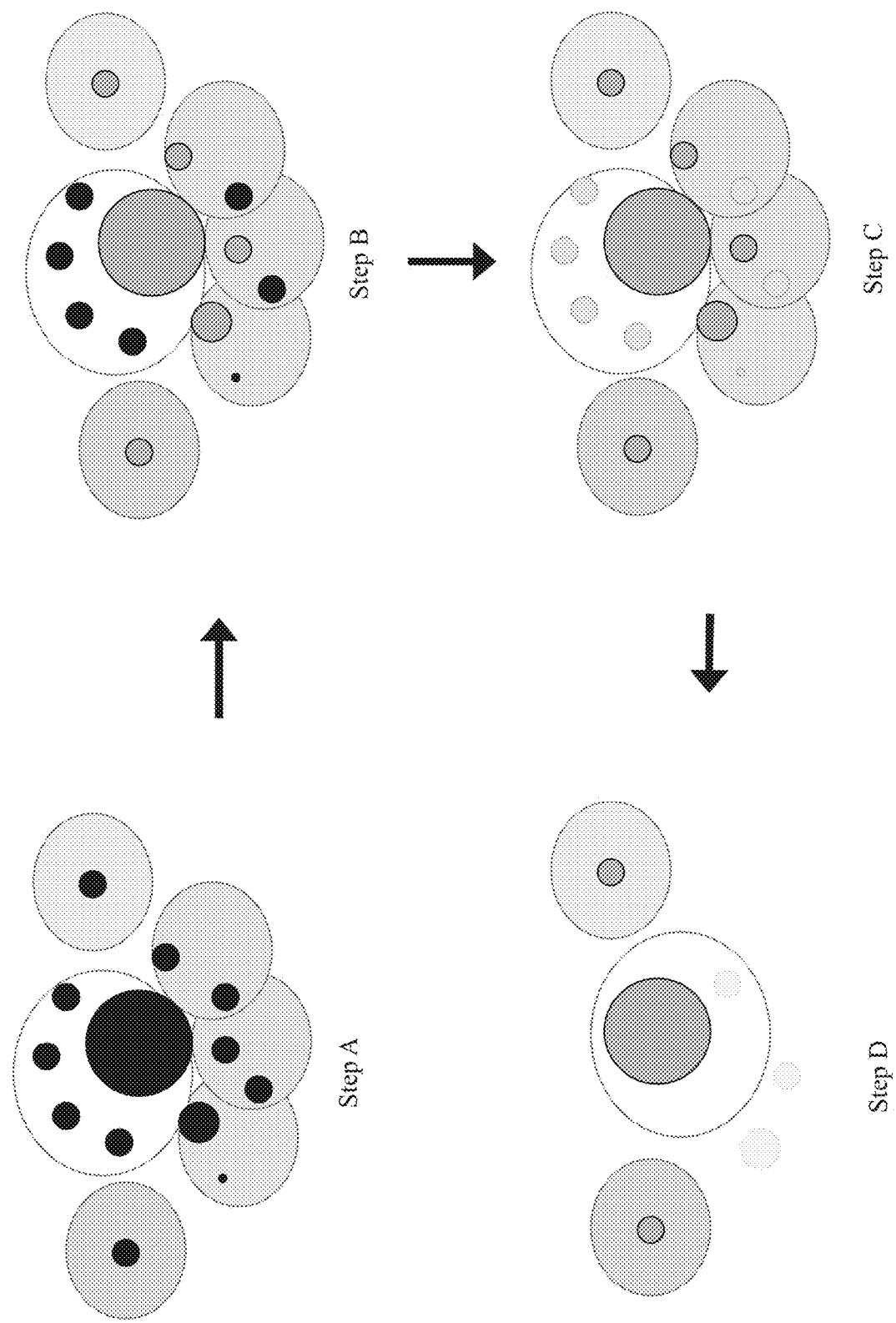
FIG. 1 is a diagram of an exemplary workflow for removal of PCR or sequencing-derived errors using stepwise clustering of similar CDR3 nucleotides sequences with steps: (A) very fast heuristic clustering into groups based on similarity (cd-hit-est); (B) cluster representative chosen as most common sequence, randomly picked for ties; (C) merge reads into representatives; (D) compare representatives and if within allotted hamming distance, merge clusters.

We have developed a multiplex next generation sequencing workflow for effective detection and analysis of the immune repertoire in a sample. Provided methods, compositions, systems, and kits are for use in high accuracy amplification and sequencing of genomic DNA (gDNA) having rearranged immune cell receptor gene sequences (e.g., T cell receptor (TCR), B cell receptor (antibody or BCR) targets) in monitoring and resolving complex immune cell repertoire(s) in a subject. The target immune cell receptor genes have undergone rearrangement (or recombination) of the VDJ or VJ gene segments, the gene segments depending on the particular receptor gene (e.g., TCR beta or TCR alpha). In certain embodiments, the present disclosure provides methods, compositions, and systems that use nucleic acid amplification, such as polymerase chain reaction (PCR), to enrich rearranged target immune cell receptor gene sequences from gDNA for subsequent sequencing. In certain embodiments, the present disclosure also provides methods and systems for effective identification and removal of amplification or sequencing-derived error(s) from V gene sequences to improve read assignment accuracy and lower the false positive rate. In particular, provided methods described herein may improve accuracy and performance in sequencing applications with nucleotide sequences associated with genomic recombination and high variability. In some embodiments, methods, compositions, systems, and kits provided herein are for use in amplification and sequencing of the complementarily determining regions (CDRs) of rearranged immune cell receptor gDNA in a sample. Thus, provided herein are multiplex immune cell receptor gene-directed compositions for multiplex library preparation from rearranged immune cell receptor gDNA, used in conjunction with next generation sequencing technologies and workflow solutions (e.g., manual or automated), for effective detection and characterization of the immune repertoire in a sample.

In some embodiments, methods and compositions are provided for amplifying the rearranged variable regions of immune cell receptor gDNA, e.g., rearranged TCR and BCR gene DNA. Multiplex amplification is used to enrich for a portion of rearranged TCR or BCR gDNA which includes at least a portion of the variable region of the receptor. In some embodiments, the amplified gDNA includes one or more complementarity determining regions CDR1, CDR2, and/or CDR3 for the target receptor. In some embodiments, the amplified gDNA includes one or more complementarily determining regions CDR1, CDR2, and/or CDR3 for TCR beta. In some embodiments, the amplified gDNA includes primarily CDR3 for the target receptor, e.g., CDR3 for TCR beta.

The complementarity determining regions of a TCR or BCR results from genomic DNA undergoing recombination of the V(D)J gene segments as well as addition and/or deletion of nucleotides at the gene segment junctions. Recombination of the V(D)J gene segments and subsequent hypermutation events leads to extensive diversity of the expressed immune cell receptors. With the stochastic nature of V(D)J recombination, rearrangement of the T or B cell receptor genomic DNA can fail to produce a functional receptor, instead producing what is termed an "unproductive" rearrangement. Typically, unproductive rearrangements have out-of-frame V and J coding segments, and lead to the presence of premature stop codons and synthesis of irrelevant peptides. TCR and BCR sequences can also appear as unproductive rearrangements from errors introduced during amplification reactions or during sequencing processes. For example, an insertion or deletion (indel) error during a target amplification or sequencing reaction can cause a frameshift in the reading frame of the resulting coding sequence. Such a change may result in a target sequence read of a productive rearrangement being interpreted as an unproductive rearrangement and discarded from the group of identified clonotypes. Accordingly, in some embodiments, the provided methods and systems include processes for identification and/or removing PCR or sequencing-derived error from the determined immune receptor sequence.

As used herein, "immune cell receptor" and "immune receptor" are used interchangeably.

As used herein, the terms "complementarity determining region" and "CDR" refer to regions of a T cell receptor or an antibody where the molecule complements an antigen's conformation, thereby determining the molecule's specificity and contact with a specific antigen. In the variable regions of T cell receptors and antibodies, the CDRs are interspersed with regions that are more conserved, termed framework regions (FR). Each variable region of a T cell receptor and an antibody contains 3 CDRs, designated CDR1, CDR2 and CDR3, and also contains 4 framework sub-regions, designated FR1, FR2, FR3 and FR4.

As used herein, the term "framework" or "framework region" or "FR" refers to the residues of the variable region other than the CDR residues as defined herein. There are four separate framework sub-regions that make up the framework: FR1, FR2, FR3, and FR4.

The particular designation in the art for the exact location of the CDRs and FRs within the receptor molecule (TCR or immunoglobulin) varies depending on what definition is employed. Unless specifically stated otherwise, the IMGT designations are used herein in describing the CDR and FR regions (see Brochet et al. (2008) Nucleic Acids Res. 36:W503-508, herein specifically incorporated by reference). As one example of CDR/FR amino acid designations, the residues that make up the FRs and CDRs of T cell receptor beta have been characterized by IMGT as follows: residues 1-26 (FR1), 27-38 (CDR1), 39-55 (FR2), 56-65 (CDR2), 66-104 (FR3), 105-117 (CDR3), and 118-128 (FR4).

Other well-known standard designations for describing the regions include those found in Kabat et al., (1991) Sequences of Proteins of Immunological Interest, 5th Ed. Public Health Service, National Institutes of Health, Bethesda, Md., and in Chothia and Lesk (1987) J. Mol. Biol. 196:901-917; herein specifically incorporated by reference. As one example of CDR designations, the residues that make up the six immunoglobulin CDRs have been characterized by Kabat as follows: residues 24-34 (CDRL1), 50-56 (CDRL2) and 89-97 (CDRL3) in the light chain variable region and 31-35 (CDRH1), 50-65 (CDRH2) and 95-102 (CDRH3) in the heavy chain variable region; and by Chothia as follows: residues 26-32 (CDRL1), 50-52 (CDRL2) and 91-96 (CDRL3) in the light chain variable region and 26-32 (CDRH1), 53-55 (CDRH2) and 96-101 (CDRH3) in the heavy chain variable region.

The term "T cell receptor" or "T cell antigen receptor" or "TCR," as used herein, refers to the antigen/MHC binding heterodimeric protein product of a vertebrate, e.g., mammalian, TCR gene complex, including the human TCR alpha, beta, gamma and delta chains. For example, the complete sequence of the human TCR beta locus has been sequenced, see, for example, Rowen et al. (1996) Science 272:1755-1762; the human TCR alpha locus has been sequenced and resequenced, see, for example, Mackelprang et al. (2006) Hum Genet. 119:255-266; and see, for example, Arden (1995) Immunogenetics 42:455-500 for a general analysis of the T-cell receptor variable gene segment families; each of which is herein specifically incorporated by reference for the sequence information provided and referenced in the publication.

The term "antibody" or immunoglobulin" or "B cell receptor" or "BCR," as used herein, is intended to refer to immunoglobulin molecules comprised of four polypeptide chains, two heavy (H) chains and two light (L) chains (lambda or kappa) inter-connected by disulfide bonds. An antibody has a known specific antigen with which it binds. Each heavy chain of an antibody is comprised of a heavy chain variable region (abbreviated herein as HCVR, HV or VH) and a heavy chain constant region. The heavy chain constant region is comprised of three domains, CHL CH2 and CH3. Each light chain is comprised of a light chain variable region (abbreviated herein as LCVR or VL or KV or LV to designate kappa or lambda light chains) and a light chain constant region. The light chain constant region is comprised of one domain, CL.

As noted, the diversity of the TCR and BCR chain CDRs is created by recombination of germline variable (V), diversity (D), and joining (J) gene segments, as well as by independent addition and deletion of nucleotides at each of the gene segment junctions during the process of TCR and BCR gene rearrangement. In the rearranged DNA encoding a TCR beta receptor and a TCR delta receptor, for example, CDR1 and CDR2 are found in the V gene segment and CDR3 includes some of the V gene segment, and the D and J gene segments. In the rearranged DNA encoding a TCR alpha receptor and a TCR gamma receptor, CDR1 and CDR2 are found in the V gene segment and CDR3 includes some of the V gene segment and the J gene segment. In the rearranged DNA encoding a BCR heavy chain, CDR1 and CDR2 are found in the V gene segment and CDR3 includes some of the V gene segment and the D and J gene segments. In the rearranged DNA encoding a BCR light chain, CDR1 and CDR2 are found in the V gene segment and CDR3 includes some of the V gene segment and the J gene segment.

In some embodiments, a multiplex amplification reaction is used to amplify TCR or BCR genomic DNA having undergone V(D)J rearrangement. In some embodiments, a multiplex amplification reaction is used to amplify nucleic acid molecule(s) comprising at least a portion of a TCR or BCR CDR from gDNA derived from a biological sample. In some embodiments, a multiplex amplification reaction is used to amplify nucleic acid molecule(s) comprising at least two CDRs of a TCR or BCR from gDNA derived from a biological sample. In some embodiments, a multiplex amplification reaction is used to amplify nucleic acid molecules comprising at least three CDRs of a TCR or BCR from gDNA derived from a biological sample. In some embodiments, the resulting amplicons are used to determine the nucleotide sequences of the rearranged TCR or BCR CDRs in the sample. In some embodiments, determining the nucleotide sequences of such amplicons comprising at least CDR3 is used to identify and characterize novel TCR or BCR alleles. In some embodiments, determining the nucleotide sequences of such amplicons comprising at least 3 CDRs is used to identify and characterize novel TCR or BCR alleles.

In the multiplex amplification reactions, each primer set used target a same TCR or BCR region however the different primers in the set permit targeting the gene's different V(D)J gene rearrangements. For example, the primer set for amplification of rearranged TCR beta gDNA are all designed to target the same region(s) from the TCR beta gene but the individual primers in the set lead to amplification of the various rearranged TCR beta VDJ gene combinations. In some embodiments, at least one primer set includes a variety of primers directed to at least a portion of J gene segments of an immune receptor gene and the other primer set includes a variety of primers directed to at least a portion of V gene segments of the same gene.

In some embodiments, multiplex amplification reactions are performed with primer sets designed to generate amplicons which include CDR1, CDR2, and/or CDR3 regions of the rearranged target immune receptor gDNA. In some embodiments, multiplex amplification reactions are performed using (i) one set of primers in which each primer is directed to at least a portion of the framework region FR3 of a V gene and (ii) one set of primers in which each primer is directed to at least a portion of the J gene of the target immune receptor. In other embodiments, multiplex amplification reactions are performed using (i) one set of primers in which each primer is directed to at least a portion of the framework region FR1 of a V gene and (ii) one set of primers in which each primer is directed to at least a portion of the J gene of the target immune receptor. In other embodiments, multiplex amplification reactions are performed using (i) one set of primers in which each primer is directed to at least a portion of the framework region FR2 of a V gene and (ii) one set of primers in which each primer is directed to at least a portion of the J gene of the target immune receptor.

In some embodiments, a multiplex amplification reaction is used to amplify rearranged TCR genomic DNA, including rearranged TCR beta, TCR alpha, TCR gamma, and TCR delta genomic DNA. In some embodiments, at least a portion of a TCR CDR, for example CDR3, is amplified from gDNA in a multiplex amplification reaction. In some embodiments, at least two CDR portions of TCR are amplified from gDNA in a multiplex amplification reaction. In certain embodiments, a multiplex amplification reaction is used to amplify at least the CDR1, CDR2, and CDR3 regions of a TCR gDNA. In some embodiments, the resulting amplicons are used to determine the rearranged TCR CDR nucleotide sequence.

In some embodiments, the multiplex amplification reaction uses (i) a set of primers each of which anneals to at least a portion of the V gene FR3 region and (ii) a set of primers which anneal to a portion of the J gene to amplify TCR gDNA such that the resultant amplicons include the CDR3 coding portion of the rearranged TCR DNA. For example, exemplary primers specific for the TCR beta (TRB) V gene FR3 regions are shown in Table 3 and exemplary primers specific for TRB J genes are shown in Table 5.

In some embodiments, the multiplex amplification reaction uses (i) a set of primers each of which anneals to at least a portion of the V gene FR1 region and (ii) a set of primers which anneal to a portion of the J gene to amplify TCR gDNA such that the resultant amplicons include the CDR1, CDR2, and CDR3 coding portions of the rearranged TCR DNA. For example, exemplary primers specific for TRB V gene FR1 regions are shown in Table 2 and exemplary primers specific for TRB J genes are shown in Table 5.

In some embodiments, the multiplex amplification reaction uses (i) a set of primers each of which anneals to at least a portion of the V gene FR2 region and (ii) a set of primers which anneal to a portion of the J gene to amplify TCR gDNA such that the resultant amplicons include the CDR2 and CDR3 coding portions of the rearranged TCR DNA. For example, exemplary primers specific for TRB V gene FR2 regions are shown in Table 4 and exemplary primers specific for TRB J genes are shown in Table 5.

In some embodiments, provided are compositions for multiplex amplification of at least a portion of rearranged TCR or BCR variable region comprising V(D)J gene segments. In some embodiments, the composition comprises a plurality of sets of primer pair reagents directed to a portion of a V gene framework region and a portion of a J gene of target immune receptor genes selected from the group consisting of TCR beta, TCR alpha, TCR gamma, TCR delta, immunoglobulin heavy chain, immunoglobulin light chain lambda, and immunoglobulin light chain kappa.

Amplification by PCR is performed with at least two primers. For the methods provided herein, a set of primers is used that is sufficient to amplify all or a defined portion of the variable region (V(D)J) sequences at the locus of interest, which locus may include any or all of the aforementioned TCR and immunoglobulin loci. In some embodiments, various parameters or criteria outlined herein may be used to select the set of target-specific primers for the multiplex amplification.

In some embodiments, primer sets used in the multiplex reactions are designed to amplify at least 50% of the known gDNA rearrangements at the locus of interest. In certain embodiments, primer sets used in the multiplex reactions are designed to amplify at least 75%, at least 85%, at least 90%, at least 95%, at least 97%, at least 98% or more of the known gDNA rearrangements at the locus of interest. For example, use of 59 forward primers of Table 3, each directed to a portion of the FR3 region from different TCR beta V genes, in combination with 16 reverse primers of Table 5, each directed to a portion of different TCR beta J genes, will amplify all of the currently known TCR beta gene rearrangements. In some embodiments, use of 59 forward primers of Table 3, each directed to a portion of the FR3 region from different TCR beta V genes, in combination with 14 reverse primers of Table 5, each directed to a portion of different TCR beta J genes, will amplify all of the currently known TCR beta gene rearrangements. For another example, use of 64 forward primers of Table 2, each directed to a portion of the FR1 region from different TCR beta V genes, in combination with 16 reverse primers of Table 5, each directed to a portion of different TCR beta J genes, will amplify all of the currently known TCR beta gene rearrangements. In other embodiments, use of 64 forward primers of Table 2, each directed to a portion of the FR1 region from different TCR beta V genes, in combination with 14 reverse primers of Table 5, each directed to a portion of different TCR beta J genes, will amplify all of the currently known TCR beta gene rearrangements.

In some embodiments, a multiplex amplification reaction includes at least 20, 25, 30, 40, 45, preferably 50, 55, 60, 65, 70, 75, 80, 85, or 90 reverse primers in which each reverse primer is directed to a sequence corresponding to at least a portion of one or more TCR V gene FR3 regions. In such embodiments, the plurality of reverse primers directed to the TCR V gene FR3 regions is combined with at least 10, 12, 14, 16, 18, 20, or about 15 to about 20 forward primers directed to a sequence corresponding to at least a portion of a J gene of the same TCR gene. In some embodiments of the multiplex amplification reactions, the TCR V gene FR3-directed primers may be the forward primers and the TCR J gene-directed primers may be the reverse primers. Accordingly, in some embodiments, a multiplex amplification reaction includes at least 20, 25, 30, 40, 45, preferably 50, 55, 60, 65, 70, 75, 80, 85, or 90 forward primers in which each forward primer is directed to a sequence corresponding to at least a portion of one or more TCR V gene FR3 regions. In such embodiments, the plurality of forward primers directed to the TCR V gene FR3 regions is combined with at least 10, 12, 14, 16, 18, 20, or about 15 to about 20 reverse primers directed to a sequence corresponding to at least a portion of a J gene of the same TCR gene. In some embodiments, such FR3 and J gene amplification primer sets may be directed to TCR beta gene sequences. In some preferred embodiments, about 55 to about 65 forward primers directed to different TRB V gene FR3 regions are combined with about 15 to about 20 reverse primers directed to different TRB J genes. In some preferred embodiments, about 55 to about 65 forward primers directed to different TRB V gene FR3 regions are combined with about 12 to about 18 reverse primers directed to different TRB J genes. In some preferred embodiments, the forward primers directed to TRB V gene FR3 regions are selected from those listed in Table 3 and the reverse primers directed to the TRB J gene are selected from those listed in Table 5. In other embodiments, the FR3 and J gene amplification primer sets may be directed to TCR alpha, TCR gamma, TCR delta, immunoglobulin heavy chain, immunoglobulin light chain lambda, and immunoglobulin light chain kappa gene sequences.

In some embodiments, such a multiplex amplification reaction includes at least 20, 25, 30, 40, 45, 49, preferably 50, 55, 60, 65, 70, 75, 80, 85, or 90 reverse primers in which each reverse primer is directed to a sequence corresponding to at least a portion of one or more TCR V gene FR1 regions. In such embodiments, the plurality of reverse primers directed to the TCR V gene FR1 regions is combined with at least 10, 12, 14, 16, 18, 20, or about 15 to about 20 forward primers directed to a sequence corresponding to at least a portion of a J gene of the same TCR gene. In some embodiments of the multiplex amplification reactions, the TCR V gene FR1-directed primers may be the forward primers and the TCR J gene-directed primers may be the reverse primers. Accordingly, in some embodiments, a multiplex amplification reaction includes at least 20, 25, 30, 40, 45, 49, preferably 50, 55, 60, 65, 70, 75, 80, 85, or 90 forward primers in which each forward primer is directed to a sequence corresponding to at least a portion of one or more TCR V gene FR1 regions. In such embodiments, the plurality of forward primers directed to the TCR V gene FR1 regions is combined with at least 10, 12, 14, 16, 18, 20, or about 15 to about 20 reverse primers directed to a sequence corresponding to at least a portion of a J gene of the same TCR gene. In some embodiments, such FR1 and J gene amplification primer sets may be directed to TCR beta gene sequences. In some preferred embodiments, about 60 to about 70 forward primers directed to different TRB V gene FR1 regions are combined with about 15 to about 20 reverse primers directed to different TRB J genes. In some preferred embodiments, about 60 to about 70 forward primers directed to different TRB V gene FR1 regions are combined with about 12 to about 18 reverse primers directed to different TRB J genes. In some preferred embodiments, the forward primers directed to TRB V gene FR1 regions are selected from those listed in Table 2 and the reverse primers directed to the TRB J gene are selected from those listed in Table 5. In other embodiments, the FR1 and J gene amplification primer sets may be directed to TCR alpha, TCR gamma, TCR delta, immunoglobulin heavy chain, immunoglobulin light chain lambda, or immunoglobulin light chain kappa gene sequences.

In some embodiments, a multiplex amplification reaction includes at least 20, 25, 30, 40, 45, 50, 55, 60, 65, 70, 75, 80, 85, or 90 reverse primers in which each reverse primer is directed to a sequence corresponding to at least a portion of one or more TCR V gene FR2 regions. In such embodiments, the plurality of reverse primers directed to the TCR V gene FR2 regions is combined with at least 10, 12, 14, 16, 18, 20, or about 15 to about 20 forward primers directed to a sequence corresponding to at least a portion of a J gene of the same TCR gene. In some embodiments of the multiplex amplification reactions, the TCR V gene FR2-directed primers may be the forward primers and the TCR J gene-directed primers may be the reverse primers. Accordingly, in some embodiments, a multiplex amplification reaction includes at least 20, 25, 30, 40, 45, 50, 55, 60, 65, 70, 75, 80, 85, or 90 forward primers in which each forward primer is directed to a sequence corresponding to at least a portion of one or more TCR V gene FR2 regions. In such embodiments, the plurality of forward primers directed to the TCR V gene FR2 regions is combined with at least 10, 12, 14, 16, 18, 20, or about 15 to about 20 reverse primers directed to a sequence corresponding to at least a portion of a J gene of the same TCR gene. In some embodiments, such FR2 and J gene amplification primer sets may be directed to TCR beta gene sequences. In some preferred embodiments, about 20 to about 30 forward primers directed to different TRB V gene FR2 regions are combined with about 15 to about 20 reverse primers directed to different TRB J genes. In some preferred embodiments, about 20 to about 30 forward primers directed to different TRB V gene FR2 regions are combined with about 12 to about 18 reverse primers directed to different TRB J genes. In some preferred embodiments, the forward primers directed to TRB V gene FR2 regions are selected from those listed in Table 4 and the reverse primers directed to the TRB J gene are selected from those listed in Table 5. In other embodiments, the FR2 and J gene amplification primer sets may be directed to TCR alpha, TCR gamma, TCR delta, immunoglobulin heavy chain, immunoglobulin light chain lambda, or immunoglobulin light chain kappa gene sequences.

In some embodiments, the concentration of the forward primer is about equal to that of the reverse primer in a multiplex amplification reaction. In other embodiments, the concentration of the forward primer is about twice that of the reverse primer in a multiplex amplification reaction. In other embodiments, the concentration of the forward primer is about half that of the reverse primer in a multiplex amplification reaction. In some embodiments, the concentration of each of the primers targeting the V gene FR region is about 5 nM to about 2000 nM. In some embodiments, the concentration of each of the primers targeting the V gene FR region is about 50 nM to about 800 nM. In some embodiments, the concentration of each of the primers targeting the V gene FR region is about 50 nM to about 400 nM or about 100 nM to about 500 nM. In some embodiments, the concentration of each of the primers targeting the V gene FR region is about 200 nM, about 400 nM, about 600 nM, or about 800 nM. In some embodiments, the concentration of each of the primers targeting the V gene FR region is about 5 nM, about 10 nM, about 50 nM, about 100 nM, about 150 nM. In some embodiments, the concentration of each of the primers targeting the V gene FR region is about 1000 nM, about 1250 nM, about 1500 nM, about 1750 nM, or about 2000 nM. In some embodiments, the concentration of each of the primers targeting the V gene FR region is about 50 nM to about 800 nM. In some embodiments, the concentration of each of the primers targeting the J gene is about 5 nM to about 2000 nM. In some embodiments, the concentration of each of the primers targeting the J gene is about 50 nM to about 800 nM. In some embodiments, the concentration of each of the primers targeting the J gene is about 50 nM to about 400 nM or about 100 nM to about 500 nM. In some embodiments, the concentration of each of the primers targeting the J gene is about 200 nM, about 400 nM, about 600 nM, or about 800 nM. In some embodiments, the concentration of each of the primers targeting the J gene is about 5 nM, about 10 nM, about 50 nM, about 100 nM, about 150 nM. In some embodiments, the concentration of each of the primers targeting the J gene is about 1000 nM, about 1250 nM, about 1500 nM, about 1750 nM, or about 2000 nM. In some embodiments, the concentration of each of the primers targeting the J gene is about 50 nM to about 800 nM. In some embodiments, the concentration of each forward and reverse primer in a multiplex reaction is about 50 nM, about 100 nM, about 200 nM, or about 400 nM. In some embodiments, the concentration of each forward and reverse primer in a multiplex reaction is about 5 nM to about 2000 nM. In some embodiments, the concentration of each forward and reverse primer in a multiplex reaction is about 50 nM to about 800 nM. In some embodiments, the concentration of each forward and reverse primer in a multiplex reaction is about 50 nM to about 400 nM or about 100 nM to about 500 nM. In some embodiments, the concentration of each forward and reverse primer in a multiplex reaction is about 600 nM, about 800 nM, about 1000 nM, about 1250 nM, about 1500 nM, about 1750 nM, or about 2000 nM. In some embodiments, the concentration of each forward and reverse primer in a multiplex reaction is about 5 nM, about 10 nM, about about 150 nM or 50 nM to about 800 nM.

In some embodiments, the V gene FR and J gene target-directed primers combine as amplification primer pairs to amplify target rearranged immune receptor gDNA sequences and generate target amplicons. Generally, the length of a target amplicon will depend upon which V gene primer set (eg, FR1-, FR2-, or FR3-directed primers) is paired with the J gene primers. Accordingly, in some embodiments, target amplicons (including TCR beta amplicons) can range from about 50 nucleotides to about 350 nucleotides in length. In some embodiments, target amplicons are about 50 to about 200, about 70 to about 170, about 200 to about 350, about 250 to about 320, about 270 to about 300, about 225 to about 300, about 250 to about 275, about 200 to about 235, about 200 to about 250, or about 175 to about 275 nucleotides in length. In some embodiments, TCR beta amplicons, such as those generated using V gene FR3- and J gene-directed primer pairs, are about 50 to about 200, about 60 to about 160, about 65 to about 120, about 70 to about 100, about 70 to about 90 nucleotides, or about 80 nucleotides in length. In some embodiments, generating amplicons of such short lengths allows the provided methods and compositions to effectively detect and analyze the immune repertoire from highly degraded gDNA template material, such as that derived from an FFPE sample.

In some embodiments, amplification primers may include a barcode sequence, for example to distinguish or separate a plurality of amplified target sequences in a sample. In some embodiments, amplification primers may include two or more barcode sequences, for example to distinguish or separate a plurality of amplified target sequences in a sample. In some embodiments, amplification primers may include a tagging sequence that can assist in subsequent cataloguing, identification or sequencing of the generated amplicon. In some embodiments, the barcode sequence(s) or the tagging sequence(s) is incorporated into the amplified nucleotide sequence through inclusion in the amplification primer or by ligation of an adapter. Primers may further comprise nucleotides useful in subsequent sequencing, e.g., pyrosequencing. Such sequences are readily designed by commercially available software programs or companies.

In some embodiments, multiplex amplification is performed with target-directed amplification primers which do not include a tagging sequence. In other embodiments, multiplex amplification is performed with amplification primers each of which include a target-directed sequence and a tagging sequence such as, for example, the forward primer or primer set includes tagging sequence 1 and the reverse primer or primer set includes tagging sequence 2. In still other embodiments, multiplex amplification is performed with amplification primers where one primer or primer set includes target directed sequence and a tagging sequence and the other primer or primer set includes a target-directed sequence but does not include a tagging sequence, such as, for example, the forward primer or primer set includes a tagging sequence and the reverse primer or primer set does not include a tagging sequence.

Accordingly, in some embodiments, a plurality of target gDNA template molecules are amplified in a single multiplex amplification reaction mixture with TCR or BCR directed amplification primers in which the forward and/or reverse primers include a tagging sequence and the resultant amplicons include the target rearranged TCR or BCR sequence and a tagging sequence on one or both ends. In some embodiments, the forward and/or reverse amplification primer or primer sets may also include a barcode and the one or more barcode is then included in the resultant amplicon.

In some embodiments, a plurality of target gDNA template molecules are amplified in a single multiplex amplification reaction mixture with TCR or BCR directed amplification primers and the resultant amplicons contain only TCR or BCR sequences. In some embodiments, a tagging sequence is added to the ends of such amplicons through, for example, adapter ligation. In some embodiments, a barcode sequence is added to one or both ends of such amplicons through, for example, adapter ligation.

Nucleotide sequences suitable for use as barcodes and for barcoding libraries are known in the art. Adapters and amplification primers and primer sets including a barcode sequence are commercially available. Oligonucleotide adapters containing a barcode sequence are also commercially available including, for example, IonXpress™, IonCode™ and Ion Select barcode adapters (Thermo Fisher Scientific). Similarly, additional and other universal adapter/primer sequences described and known in the art (e.g., Illumina universal adapter/primer sequences, PacBio universal adapter/primer sequences, etc.) can be used in conjunction with the methods and compositions provided herein and the resultant amplicons sequenced using the associated analysis platform.

In some embodiments, two or more barcodes are added to amplicons when sequencing multiplexed samples. In some embodiments, at least two barcodes are added to amplicons prior to sequencing multiplexed samples to reduce the frequency of artefactual results (e.g., immune receptor gene rearrangements or clone identification) derived from barcode cross-contamination or barcode bleed-through between samples. In some embodiments, at least two bar codes are used to label samples when tracking low frequency clones of the immune repertoire. In some embodiments, at least two barcodes are added to amplicons when the assay is used to detect clones of frequency less than 1:1,000. In some embodiments, at least two barcodes are added to amplicons when the assay is used to detect clones of frequency less than 1:10,000. In other embodiments, at least two barcodes are added to amplicons when the assay is used to detect clones of frequency less than 1:20,000, less than 1:40,000, less than 1:100,000, less than 1:200,000, less than 1:400,000, less than 1:500,00, or less than 1:1,000,000. Methods for characterizing the immune repertoire which benefit from a high sequencing depth per clone and/or detection of clones at such low frequencies include, but are not limited to, monitoring a patient with a hyperproliferative disease undergoing treatment and testing for minimal residual disease following treatment.

In some embodiments, target-specific primers (e.g., the V gene FR1-, FR2- and FR3-directed primers and the J gene directed primers) used in the methods of the invention are selected or designed to satisfy any one or more of the following criteria: (1) includes two or more modified nucleotides within the primer sequence, at least one of which is included near or at the termini of the primer and at least one of which is included at, or about the center nucleotide position of the primer sequence; (2) length of about 15 to about 40 bases in length; (3) Tm of from above 60'C to about 70° C.; (4) has low cross-reactivity with non-target sequences present in the sample of interest; (5) at least the first four nucleotides (going from 3' to 5' direction) are non-complementary to any sequence within any other primer present in the same reaction; and (6) non-complementarity to any consecutive stretch of at least 5 nucleotides within any other produced target amplicon. In some embodiments, the target-specific primers used in the methods provided are selected or designed to satisfy any 2, 3, 4, 5, or 6 of the above criteria.

In some embodiments, the target-specific primers used in the methods of the invention include one or more modified nucleotides having a cleavable group. In some embodiments, the target-specific primers used in the methods of the invention include two or more modified nucleotides having cleavable groups. In some embodiments, the target-specific primers comprise at least one modified nucleotide having a cleavable group selected from methylguanine, 8-oxo-guanine, xanthine, hypoxanthine, 5,6-dihydrouracil, uracil, 5-methylcytosine, thymine-dimer, 7-methylguanosine, 8-oxo-deoxyguanosine, xanthosine, inosine, dihydrouridine, bromodeoxyuridine, uridine or 5-methylcytidine.

In some embodiments, target amplicons using the amplification methods (and associated compositions, systems, and kits) disclosed herein, are used in the preparation of an immune receptor repertoire library. In some embodiments, the immune receptor repertoire library includes introducing adapter sequences to the termini of the target amplicon sequences. In certain embodiments, a method for preparing an immune receptor repertoire library includes generating target immune receptor amplicon molecules according to any of the multiplex amplification methods described herein, treating the amplicon molecule by digesting a modified nucleotide within the amplicon molecules' primer sequences, and ligating at least one adapter to at least one of the treated amplicon molecules, thereby producing a library of adapter-ligated target immune receptor amplicon molecules comprising the target immune receptor repertoire. In some embodiments, the steps of preparing the library are carried out in a single reaction vessel involving only addition steps. In certain embodiments, the method further includes clonally amplifying a portion of the at least one adapter-ligated target amplicon molecule.

In some embodiments, target amplicons using the methods (and associated compositions, systems, and kits) disclosed herein, are coupled to a downstream process, such as but not limited to, library preparation and nucleic acid sequencing. For example, target amplicons can be amplified using bridge amplification, emulsion PCR or isothermal amplification to generate a plurality of clonal templates suitable for nucleic acid sequencing. In some embodiments, the amplicon library is sequenced using any suitable DNA sequencing platform such as any next generation sequencing platform, including semi-conductor sequencing technology such as the Ion Torrent sequencing platform. In some embodiments, an amplicon library is sequenced using an Ion Torrent S5 520™ System, an Ion Torrent S5 530™ System, an Ion Torrent S5 540™ System or an Ion Torrent PGM 318™ System.

In some embodiments, sequencing of immune receptor amplicons generated using the methods (and associated compositions and kits) disclosed herein, produces contiguous sequence reads from about 50 to about 170 nucleotides, about 60 to about 160 nucleotides, about 60 to about 120 nucleotides, about 70 to about 100 nucleotides, about 70 to about 90 nucleotides, or about 80 nucleotides in length. In some embodiments, read lengths average about 70, about 80, about 85, about 90, about 100, about 110, or about 120 nucleotides. In some embodiments, contiguous read lengths are from about 250 to about 350 nucleotides, about 275 to about 340, or about 295 to about 325 nucleotides in length. In some embodiments, read lengths average about 270, about 280, about 290, about 300, or about 325 nucleotides in length. In other embodiments, contiguous read lengths are from about 180 to about 300 nucleotides, about 200 to about 290 nucleotides, about 225 to about 280 nucleotides, or about 230 to about 250 nucleotides in length. In some embodiments, read lengths average about 200, about 220, about 230, about 240, or about 250 nucleotides in length. In some embodiments, the sequence read length include the amplicon sequence and a barcode sequence. In some embodiments, the sequence read length does not include a barcode sequence.

In some embodiments, the amplification primers and primer pairs are target-specific sequences that can amplify specific regions of a nucleic acid molecule. In some embodiments, the target-specific primers can amplify DNA, such as gDNA. In some embodiments, the target-specific primers can amplify mammalian DNA, such as human DNA or murine DNA.

In methods and compositions provided herein, for example those for determining, characterizing, and/or tracking the immune repertoire in a biological sample, the amount of input gDNA required for amplification of target sequences will depend in part on the fraction of immune receptor bearing cells (e.g., T cells or B cells) in the sample. For example, a higher fraction of T cells in the sample permits use of a lower amount of input gDNA for amplification. In some embodiments, the amount of input gDNA for amplification of one or more target sequences can be about 0.1 ng to about 10 micrograms. In some embodiments, the amount of gDNA required for amplification of one or more target sequences can be from about 0.5 ng to about 5 micrograms. In some embodiments, the amount of gDNA required for amplification of one or more target sequences can be from about 1 ng to about 1 microgram or about 10 ng to about 1 microgram. In some embodiments, the amount of gDNA required for amplification of one or more immune repertoire target sequences is from about 10 ng to about 500 ng, about 25 ng to about 400 ng, or from about 50 ng to about 200 ng. In some embodiments, the amount of gDNA required for amplification of one or more target sequences is about 0.5 ng, about 1 ng, about 5 ng, about 10 ng, about 20 ng, about 50 ng, about 100 ng, or about 200 ng. In some embodiments, the amount of gDNA required for amplification of one or more immune repertoire target sequences is about 1 microgram, about 2 micrograms, about 3 micrograms, about 4.0 micrograms, or about 5 micrograms.

In some embodiments, gDNA is obtained from a biological sample using conventional methods. Methods and reagents for extracting or isolating nucleic acid from biological samples are well known and commercially available. In some embodiments, DNA extraction from biological samples is performed by any method described herein or otherwise known to those of skill in the art, e.g., methods involving proteinase K tissue digestion and alcohol-based nucleic acid precipitation, treatment with RNAse to digest contaminating RNA, and DNA purification using silica-gel-membrane technology, or any combination thereof. Exemplary methods for DNA extraction from biological samples using commercially available kits including Ion AmpliSeq™ Direct FFPE DNA Kit, MagMAX™ FFPE DNA/ RNA Ultra Kit, TRI Reagent™ (Invitrogen), PureLink™ Genomic DNA Mini kit (Invitrogen), RecoverAll™ Total Nucleic Acid Isolation Kit (Invitrogen), MagMAX™ DNA Multi-Sample Kit (Invitrogen) and DNA extraction kits from BioChain Institute Inc. (e.g., FFPE Tissue DNA Extraction Kit, Genomic DNA Extraction Kit, Blood and Serum DNA Isolation Kit).

A sample or biological sample, as used herein, refers to a composition from an individual that contains or may contain cells related to the immune system. Exemplary biological samples, include without limitation, tissue (for example, lymph node, organ tissue, bone marrow), whole blood, synovial fluid, cerebral spinal fluid, tumor biopsy, and other clinical specimens containing cells. The sample may include normal and/or diseased cells and be a fine needle aspirate, fine needle biopsy, core sample, or other sample. In some embodiments, the sample may be fresh (e.g., not preserved), frozen, or formalin-fixed paraffin-embedded tissue (FFPE). Some samples comprise cancer cells, such as carcinomas, melanomas, sarcomas, lymphomas, myelomas, leukemias, and the like.

The biological sample can be a mix of tissue or cell types, a preparation of cells enriched for at least one particular category or type of cell, or an isolated population of cells of a particular type or phenotype. Samples can be separated by centrifugation, elutriation, density gradient separation, apheresis, affinity selection, panning, FACS, centrifugation with Hypaque, etc. prior to analysis. Methods for sorting, enriching for, and isolating particular cell types are well-known and can be readily carried out by one of ordinary skill.

In one aspect, the provided methods and systems include processes for analysis of immune receptor gDNA sequence data and for identification and/or removing PCR or sequencing-derived error(s) from at least portions of the V gene sequences of the determined immune receptor sequence.

As provided herein, V gene-directed primers are paired with J gene-directed primers in multiplex amplification of the immune receptor gDNA sequences, for example multiplex amplification with primers pairs directed to V gene FR3 regions and J genes. Raw sequence reads derived from the assay undergo a J gene sequence inference process before any downstream analysis. In this process, the beginning and end of raw read sequences are interrogated for the presence of characteristic sequences of 10-30 nucleotides corresponding to the portion of the J gene sequences expected to exist after amplification with the J primer and any subsequent manipulation or processing (for example, digestion) of the amplicon termini prior to sequencing. The characteristic nucleotide sequences permit one to infer the sequence of the J primer, as well as the remaining portion of the J gene that was targeted since the sequence of each J gene is known. To complete the J gene sequence inference process, the inferred J gene sequence is added to the raw read to create an extended read that then spans the entire J gene. The extended read then contains the entire J gene sequence, the entire sequence of the CDR3 region, and at least a portion of the V gene sequence, which will be reported after downstream analysis. The portion of V gene sequence in the extended read will depend on the V gene-directed primers used for the multiplex amplification, for example, FR3-, FR2- or FR1-directed primers.

In some embodiments, the error correction strategy includes the following steps:
  1) Align the sequenced rearrangement to a reference database of variable, diversity and joining genes to produce a query sequence/reference sequence pair.

Many alignment procedures may be used for this purpose including, for example, IgBLAST, a freely-available tool from the NCBI, and custom computer scripts.
2) Realign the reference and query sequences to each other, taking into account the flow order used for sequencing. The flow order provides information that allows one to identify and correct some types of erroneous alignments.
3) Identify the borders of the CDR3 region by their characteristic sequence motifs.
4) Over the aligned portion of the rearrangement corresponding to the variable gene and joining genes, excluding the CDR3 region, identify indels in the query with respect to the reference and alter the mismatching query base position so that it is consistent with the reference.

Figure 2:
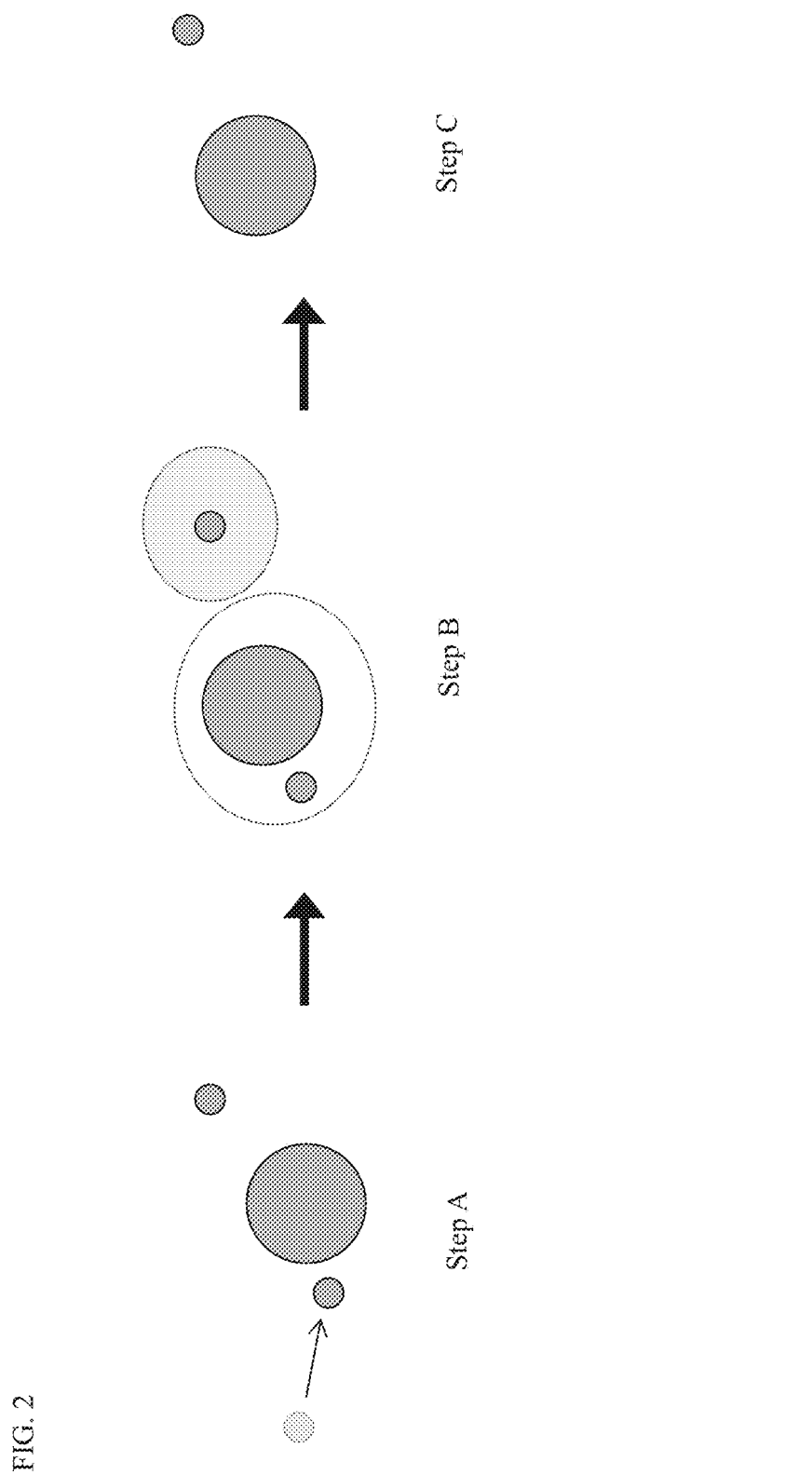
FIG. 2 is a diagram of an exemplary workflow for removal of residual insertion/deletion (indel) error by comparing homopolymer collapsed CDR3 sequences using Levenshtein distance with the steps: (A) collapse homopolymers and calculate Levenshtein distances between cluster representatives; (b) merge reads that now cluster together, these represent complex indel errors; (C) report lineages to user.

In some embodiments, methods are provided to identify T cell or B cell clones in repertoire data that are robust to PCR and sequencing error. Accordingly, the following describes steps that may be employed in such methods to identify T cell or B cell clones in a manner that is robust to PCR and sequencing error. Table 1 provides a diagram of an exemplary workflow for use in identifying and removing PCR or sequencing-derived errors from immune receptor sequencing data. Exemplary portions and embodiments of this workflow are also represented in FIGS. 1-2.

TABLE 1

SEQUENCE CORRECTION WORKFLOW

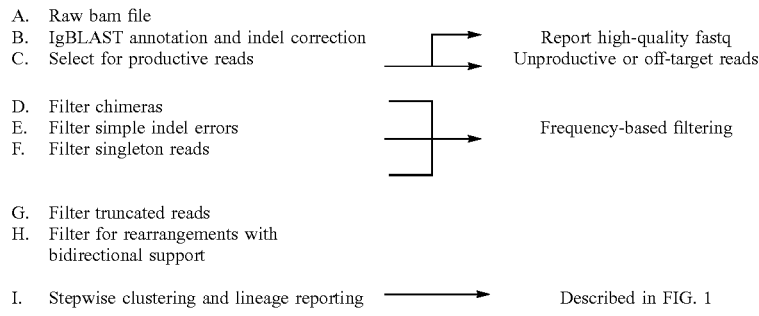

For a set of TCR or BCR sequences derived from gDNA, where 1) each sequence has been annotated as a productive rearrangement or an unproductive rearrangement, either natively or after error correction, such as previously described, and 2) each sequence has an identified variable gene and CDR3 nucleotide region, in some embodiments, methods include the following:
1) Identify and exclude chimeric sequences. For each unique CDR3 nucleotide sequence present in the dataset, tally the number of reads having that CDR3 nucleotide sequence and any of the possible variable genes. Any variable gene-CDR3 combination making up less than 10% of total reads for that CDR3 nucleotide sequence is flagged as a chimera and eliminated from downstream analyses. As an example, for the sequences below having the same CDR3 nucleotide sequence, e.g., the sequences having TRBV3 and TRBV6 paired with CDR3nt sequence AATTGGT (SEQ ID NO: 181) will be flagged as chimeric.

| Variable | CDR3nt | Read counts |
|---|---|---|
| TRBV2 | AATTGGT (SEQ ID NO: 181) | 1000 |
| TRBV3 | AATTGGT (SEQ ID NO: 181) | 10 |
| TRBV6 | AATTGGT (SEQ ID NO: 181) | 3 |

2) Identify and exclude sequences containing simple indel errors. For each read in the dataset, obtain the homopolymer-collapsed representation of the CDR3 sequence of that read. For each set of reads having the same variable gene and collapsed-CDR3 combination, tally the number of occurrences of each non-collapsed CDR3 nucleotide sequence. Any non-collapsed CDR3 sequence making up <10% of total reads for that read set is flagged as having a simple homopolymer error. As an example, three different variable gene-CDR3 nucleotide sequences are presented that are identical after homopolymer collapsing of the CDR3 nucleotide sequence. The two less frequent variable gene-CDR3 combinations make up <10% of total reads for the read set and will be flagged as containing a simple indel error. For example:

| Variable | CDR3nt | Homopolymer collapsed CDR3nt | Read counts |
|---|---|---|---|
| TRBV2 | AATTGGT (SEQ ID NO: 181) | ATGT | 1000 |
| TRBV2 | AAATGGT (SEQ ID NO: 182) | ATGT | 10 |
| TRBV2 | AAAATTTGGT (SEQ ID NO: 183) | ATGT | 3 |

3) Identify and exclude singleton reads. For each read in the dataset, tally the number of times that the exact read sequence is found in the dataset. Reads that appear only once in the dataset will be flagged as singleton reads.
4) Identify and exclude truncated reads. For each read in the dataset, determine whether the read possesses an annotated variable gene FR1, CDR1, FR2, CDR2, and FR3 region, as indicated by the IgBLAST alignment of the read to the IgBLAST reference variable gene set. Reads that do not possess the above regions are flagged as truncated if the region(s) is expected based on the particular V gene primer used for amplification.

5) Identify and exclude rearrangements lacking bidirectional support. For each read in the dataset, obtain the variable gene and CDR3 sequence of the read as well as the strand orientation of the read (plus or minus strand). For each variable gene-CDR3 combination in the dataset, tally the number of plus and minus strand reads having that variable gene-CDR3nt combination. Variable gene-CDR3nt combinations that are only present in reads of one orientation will be deemed to be a spurious. All reads having a spurious variable gene-CDR3nt combination will be flagged as lacking bidirectional support.

6) For genes that have not been flagged, perform stepwise clustering based on CDR3 nucleotide similarity. Separate the sequences into groups based on the variable gene identity of the read, excluding allele information (v-gene groups). For each group:

a. Arrange reads in each group into clusters using cd-hit-est and the following parameters:
   cd-hit-est-i vgene_groups.fa-o clustered_vgenegroups.cdhit-T 24-d 0-M 100000-B 0-r 0-g1-S0-U2-uL.05-n10-17
   Where vgene_groups.fa is a fasta format file of the CDR3 nucleotide regions of sequences having the same variable gene and clustered_vgene_groups.cdhit is the output, containing the subdivided sequences.

b. Assign each sequence in a cluster the same clone ID, used to denote that members of the subgroup are believed to represent the same T cell clone or B cell clone.

c. Chose a representative sequence for each cluster, such that the representative sequence is the sequence that appears the greatest number of times, or, in cases of a tie, is randomly chosen.

d. Merge all other reads in the cluster into the representative sequence such that the number of reads for the representative sequence is increased according to the number of reads for the merged sequences.

e. Compare the representative sequences within a v-gene group to each other on the basis of hamming distance. If a representative sequence is within a hamming distance of 1 to a representative sequence that is >50 times more abundant, merge that sequence into the more common representative sequence. If a representative sequence is within a hamming distance of 2 to a representative sequence that is >10000 times more abundant, merge that sequence into the more common representative sequence.

f. Identify complex sequence errors. Homopolymer-collapse the representative sequences within each variable gene group, then compare to each other using Levenshtein distances. If a representative sequence is within a Levenshtein distance of 1 to a representative sequence that is >50 times more abundant, merge that sequence into the more common representative sequence.

g. Identify CDR3 misannotation errors. Homopolymer-collapse the representative sequences within each variable gene group, then perform a pairwise comparison of each homopolymer-collapsed sequence. For each pair of sequences, determine whether one sequence is a subset of the other sequence. If so, merge the less abundant sequence into the more abundant sequence if the more abundance sequence is >500 fold more abundant.

7) Report cluster representatives to user.

In some embodiments, the provided workflow is not limited to the frequency ratios listed in the various steps, and other frequency ratios may be substituted for the representative ratios included above. For example, in some embodiments, comparing the representative sequences within a v-gene group to each other on the basis of hamming distance may use a frequency ratio other than those listed in step (e) above. For example and without limitation, frequency ratios of 1000, 5000, 20,000, etc may be used if a representative sequence is within a hamming distance of 2 to a representative sequence. For example and without limitation, frequency ratios of 20, 100, 200, etc may be used if a representative sequence is within a hamming distance of 1 to a representative sequence. The frequency ratios provided are representative of the general process of labeling the more abundant sequence of a similar pair as a correct sequence.

Similarly, when comparing the frequencies of two sequences at other steps in the workflow, eg, step (1), step (2), step (60 and step (6g), frequency ratios other than those listed in the step above may be used.

As used herein, the term "homopolymer-collapsed sequence" is intended to represent a sequence where repeated bases are collapsed to a single base representative. As an example, for the non-collapsed sequence AAAATTTTTATCCCCCCCCGGG (SEQ ID NO: 184), the homopolymer-collapsed sequence is ATATCG.

As used herein, the terms "clone," "clonotype," "lineage," or "rearrangement" are intended to describe a unique variable gene nucleotide combination for an immune receptor, such as a TCR or BCR. For example, a unique variable gene-CDR3 nucleotide combination.

As used herein, the term "productive reads" refers to a TCR or BCR sequence reads that have no stop codon and have in-frame variable gene and joining gene segments. Productive reads are biologically plausible in coding for a polypeptide.

As used herein, "chimeras" or chimeric sequences" refer to artefactual sequences that arise from template switching during target amplification, such as PCR. Chimeras typically present as a CDR3 sequence grafted onto an unrelated variable gene, resulting in a CDR3 sequence that is associated with multiple variable genes within a dataset. The chimeric sequence is usually far less abundant than the true sequence in the dataset.

As used herein, the term "indel" refers to an insertion and/or deletion of one or more nucleotide bases in a nucleic acid sequence. In coding regions of a nucleic acid sequence, unless the length of an indel is a multiple of 3, it will produce a frameshift when the sequence is translated. As used herein, "simple indel errors" are errors that do not alter the homopolymer-collapsed representation of the sequence. As used herein, "complex indel errors" are indel sequencing errors that alter the homopolymer-collapsed representation of the sequence and include, without limitation, errors that eliminate a homopolymer, insert a homopolymer into the sequence, or create a dyslexic-type error.

As used herein, "singleton reads" refer to sequence reads whose indel-corrected sequence appears only once in a dataset. Typically, singleton reads are enriched for reads containing a PCR or sequencing error.

As used herein, "truncated reads" refer to immune receptor sequence reads that are missing annotated variable gene regions. For example, truncated reads include, without limitation, sequence reads that are missing annotated TCR or BCR variable gene FR1, CDR1, FR2, CDR2, or FR3 regions. Such reads typically are missing a portion of the variable gene sequence due to quality trimming. Truncated reads can give rise to artifacts if the truncation leads one to misidentify the variable gene.

In the context of identified variable gene-CDR3 sequences (clonotypes), "bidirectional support" indicates that a particular variable gene-CDR3 sequence is found in at least one read that maps to the plus strand (proceeding from the variable gene to constant gene) and at least one reads that maps to the minus strand (proceeding form the constant gene to the variable gene). Systematic sequencing errors often lead to identification of variable gene-CDR3 sequences having unidirectional support.

For a set of sequences that have been grouped according to a predetermined sequence similarity threshold to account for variation due to PCR or sequencing error, the "cluster representative" is the sequence that is chosen as most likely to be error free. This is typically the most abundant sequence.

As used herein, "IgBLAST annotation error" refers to rare events where the border of the CDR3 is identified to be in an incorrect adjacent position. These events typically add three bases to the 5' or 3' end of a CDR3 nucleotide sequence.

For two sequences of equal length, the "Hamming distance" is the number of positions at which the corresponding bases are different. For any two sequences, the "Levenshtein distance" or the "edit distance" is the number of single base edits required to make one sequence into another sequence.

Use of V gene FR3 and J gene primers to amplify rearranged immune receptor gDNA sequences yields a minimum length amplicon (for example, about 60-100 or about 80 nucleotides in length) while still producing data that allows for reporting of the entire CDR3 region. With the expectation of short amplicon length, reads of amplicons <100 nucleotides in length are not eliminated as low-quality and/or off target products during the sequence analysis workflow. However, the explicit search for the expected J gene sequences in the raw reads allows one to eliminate amplicons deriving from off-target amplifications by the J gene primers. In addition, this short amplicon length improves the performance of the assay on highly degraded gDNA template material, such as that derived from an FFPE sample.

In some embodiments, provided methods comprise sequencing a rearranged immune receptor DNA library and subjecting the obtained sequence data to error identification and correction processes for the V gene portions to generate rescued productive reads, and identifying productive, rescued productive, and unproductive sequence reads. In some embodiments, provided methods comprise sequencing a rearranged immune receptor DNA library and subjecting the obtained sequence dataset to error identification and correction processes for the V gene portions, identifying productive, rescued productive, and unproductive sequence reads, and grouping the sequence reads by clonotype to identify immune receptor clonotypes in the library. In some embodiments, both productive and unproductive sequence reads of rearranged immune receptor DNA are separately reported.

In some embodiments, the provided error identification and correction workflow is used for identifying and resolving PCR or sequencing-derived errors for the V gene portion of the sequence that lead to a sequence read being identified as from an unproductive rearrangement. In some embodiments, the provided error identification and correction workflow is applied to immune receptor sequence data generated from a sequencing platform in which indel or other frameshift-causing errors occur while generating the sequence data.

In some embodiments, the provided error identification and correction workflow is applied to sequence data generated by an Ion Torrent sequencing platform. In some embodiments, the provided error identification and correction workflow is applied to sequence data generated by Roche 454 Life Sciences sequencing platforms, PacBio sequencing platforms, and Oxford Nanopore sequencing platforms.

In some embodiments, provided methods comprise preparation and formation of a plurality of immune receptor-specific amplicons. In some embodiments, the method comprises hybridizing a plurality of V gene gene-specific primers and a plurality of J gene-specific primers to a gDNA molecule, extending a first primer (eg, a V gene-specific primer) of the primer pair, denaturing the extended first primer from the gDNA molecule, hybridizing to the extended first primer product, a second primer (e.g., a J gene-specific primer) of the primer pair and extending the second primer, digesting the target-specific primer pairs to generate a plurality of target amplicons. In some embodiments, adapters are ligated to the ends of the target amplicons prior to performing a nick translation reaction to generate a plurality of target amplicons suitable for nucleic acid sequencing. In some embodiments, at least one of the ligated adapters includes at least one barcode sequence. In some embodiments, each adapter ligated to the ends of the target amplicons includes a barcode sequence. In some embodiments, the one or more target amplicons can be amplified using bridge amplification, emulsion PCR or isothermal amplification to generate a plurality of clonal templates suitable for nucleic acid sequencing.

In some embodiments, the disclosure provides methods for sequencing target amplicons and processing the sequence data to identify productive immune receptor gene rearrangements gDNA from a biological sample. In some embodiments, processing the sequence data includes inferring the nucleotide sequence of the J gene primer used for amplification as well as the remaining portion of the J gene that was targeted, as described herein. In some embodiments, processing the sequence data includes performing provided error identification and correction steps for the V gene sequence portion to generate rescued productive sequences. In some embodiments, use of the provided sequence processing and error identification and correction workflow can result in a combination of productive reads and rescued productive reads being at least 50% of the sequencing reads for an immune receptor gDNA sample. In some embodiments, use of the provided sequence processing and error identification and correction workflow can result in a combination of productive reads and rescued productive reads being at least 40%, at least 50%, at least 60%, at least 70%, at least 80%, at least 90%, or at least 95% of the sequencing reads for an immune receptor gDNA sample. In some embodiments, use of the provided sequence processing and error identification and correction workflow can result in a combination of productive reads and rescued productive reads being about 30-40%, about 40-50%, about 50-60%, about 60-70%, about 70-80%, about 80-90%, about 50-80%, or about 60-90% of the sequencing reads for an immune receptor gDNA sample. In some embodiments, use of the provided sequence processing and error identification and correction workflow can result in a combination of productive reads and rescued productive reads averaging about 40%, about 50%, about 55%, about 60%, about 65%, about 70%, about 75%, about 80%, about 85%, about 90% of the sequencing reads for an immune receptor gDNA sample.

In certain embodiments, methods of the invention comprise the use of target immune receptor primer sets wherein the primers are directed to sequences of the same target immune receptor gene. Immune receptors are selected from T cell receptors and antibody receptors. In some embodiments a T cell receptor is a T cell receptor selected from the group consisting of TCR alpha, TCR beta, TCR gamma, and TCR delta. In some embodiments the immune receptor is an antibody receptor selected from the group consisting of heavy chain alpha, heavy chain delta, heavy chain epsilon, heavy chain gamma, heavy chain mu, light chain kappa, and light chain lambda.

In certain embodiments, provided is a method for amplification of rearranged genomic nucleic acid sequences of an immune receptor repertoire in a sample, comprising performing a multiplex amplification reaction to amplify rearranged immune receptor nucleic acid template molecules having a J gene portion and a V gene portion using at least one set of: i) a plurality of V gene primers directed to a majority of different V genes of an immune receptor coding sequence comprising at least a portion of a framework region within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein performing amplification using each set results in amplicons representing the entire repertoire of the respective immune receptor in the sample; thereby generating immune receptor amplicons comprising the repertoire of the immune receptor. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In particular embodiments the one or more plurality of J gene primers of ii) are directed to sequences over about a 50 nucleotide portion of the J gene. In more particular embodiments the one or more plurality of J gene primers of ii) are directed to sequences over about a 30 nucleotide portion of the J gene. In certain embodiments, the one or more plurality of J gene primers of ii) are directed to sequences completely within the J gene.

In certain embodiments, provided is a method for amplification of rearranged genomic nucleic acid sequences of an immune receptor repertoire in a sample, comprising performing a multiplex amplification reaction to amplify rearranged immune receptor nucleic acid template molecules having a J gene portion and a V gene portion using at least one set of: i) a plurality of V gene primers directed to a majority of different V genes of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein performing amplification using each set results in amplicons representing the entire repertoire of the respective immune receptor in the sample; thereby generating immune receptor amplicons comprising the repertoire of the immune receptor. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In more particular embodiments the one or more plurality of V gene primers of i) are directed to sequences over about a 40 to about a 60 nucleotide portion of the framework region. In some embodiments the one or more plurality of V gene primers of i) anneal to at least a portion of the FR3 region of the template molecules. In certain embodiments the plurality of J gene primers of ii) comprises at least ten primers that anneal to at least a portion of the J gene portion of the template molecules. In some embodiments the plurality of J gene primers of ii) comprises about 14 primers that anneal to at least a portion of the J gene portion of the template molecules. In some embodiments the plurality of J gene primers of ii) comprises about 16 primers that anneal to at least a portion of the J gene portion of the template molecules. In some embodiments the plurality of J gene primers of ii) comprises about 10 to about 20 primers that anneal to at least a portion of the J gene portion of the template molecules. In some embodiments the plurality of J gene primers of ii) comprises about 12 to about 18 primers that anneal to at least a portion of the J gene portion of the template molecules. In particular embodiments at least one set of the generated amplicons includes complementarity determining region CDR3 of an immune receptor gene sequence. In some embodiments the amplicons are about 60 to about 160 nucleotides in length, about 70 to about 100 nucleotides in length, at least about 70 to about 90 nucleotides in length, or about 80 nucleotides in length. In some embodiments the nucleic acid template used in methods is gDNA extracted from a biological sample.

In certain embodiments, methods are provided for providing sequence of the immune repertoire in a sample, comprising performing a multiplex amplification reaction to amplify rearranged immune receptor nucleic acid template molecules having a J gene portion and a V gene portion using at least one set of primers comprising i) a plurality of V gene primers directed to a majority of different V gene of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. Sequencing of resulting immune receptor amplicon molecules is then performed and the sequences of the immune receptor amplicon molecules determined thereby provides sequence of the immune repertoire in the sample. In particular embodiments, determining the sequence of the immune receptor amplicon molecules includes obtaining initial sequence reads, adding the inferred J gene sequence to the sequence read to create an extended sequence read, aligning the extended sequence read to a reference sequence and identifying productive reads, identifying and correcting one or more indel errors in the V gene sequence to generate rescued productive sequence reads, and determining the sequences of the resulting immune receptor molecules. In particular embodiments the combination of productive reads and rescued productive reads is at least 40%, at least 50%, at least 60% at least 70% or at least 75% of the sequencing reads for the immune receptors. In additional embodiments the method further comprises sequence read clustering and immune receptor clonotype reporting. In some embodiments the sequence read lengths are about 60 to about 185 nucleotides, depending in part on inclusion of any barcode sequence in the read length. In some embodiments the average sequence read length is between 70 and 90 nucleotides, between about 75 and about 85 nucleotides, or is about 80 nucleotides. In certain embodiments at least one set of the sequenced amplicons includes complementarity determining region CDR3 of a rearranged immune receptor sequence.

In certain embodiments, methods provided utilize target immune receptor primer sets comprising V gene primers wherein the one or more of a plurality of V gene primers are directed to sequences over an FR3 region about 70 nucleotides in length. In particular embodiments, methods provided utilize target immune receptor primer sets comprising V gene primers wherein the one or more of a plurality of V gene primers are directed to sequences over an FR3 region about 50 nucleotides in length. In other particular embodiments the one or more of a plurality of V gene primers are directed to sequences over an FR3 region about 40 to about 60 nucleotides in length. In certain embodiments a target immune receptor primer set comprises V gene primers comprising about 45 to about 80 different FR3-directed primers. In certain embodiments a target immune receptor primer set comprises V gene primers comprising about 50 to about 70 different FR3-directed primers. In some embodiments, a target immune receptor primer set comprises V gene primers comprising about 55 to about 65 different FR3-directed primers. In some embodiments, a target immune receptor primer set comprises V gene primers comprising about 58, 59, 60, 61, or 62 different FR3-directed primers. In some embodiments the target immune receptor primer set comprises a plurality of J gene primers. In some embodiments a target immune receptor primer set comprises at least ten J gene primers wherein each is directed to at least a portion of a J gene within target polynucleotides. In some embodiments a target immune receptor primer set comprises at least 16 J gene primers wherein each is directed to at least a portion of a J gene within target polynucleotides. In some embodiments a target immune receptor primer set comprises about 10 to about 20 different J gene primers wherein each is directed to at least a portion of a J gene within target polynucleotides. In some embodiments a target immune receptor primer set comprises about 12, 13, 14, 15, 16, 17 or 18 different J gene primers. In particular embodiments a target immune receptor primer set comprises 16 J gene primers wherein each is directed to at least a portion of a J gene within target polynucleotides. In particular embodiments a target immune receptor primer set comprises 14 J gene primers wherein each is directed to at least a portion of a J gene within target polynucleotides.

In particular embodiments, methods of the invention comprise the use of at least one set of primers comprising V gene primers i) and J gene primers ii) selected from Tables 3 and 5, respectively. In certain embodiments methods of the invention comprise the use of at least one set of primers i) and ii) comprising primers selected from SEQ ID NOs: 185-248 and 313-397 or selected from SEQ ID NOs: 185-248 and 398-482. In certain other embodiments methods of the invention comprise the use of at least one set of primers i) and ii) comprising primers selected from SEQ ID NOs: 185-248 and 313-329 or selected from SEQ ID NOs: 185-248 and 329-342. In still other embodiments methods of the invention comprise the use of at least one set of primers of i) and ii) comprising primers selected from SEQ ID NOs: 185-248 and 398-414 or selected from SEQ ID NOs: 185-248 and 414-427. In other embodiments methods of the invention comprise the use of at least one set of primers i) and ii) comprising primers SEQ ID NOs: 185-243 and 313-328. In still other embodiments methods of the invention comprise the use of at least one set of primers of i) and ii) comprising primers SEQ ID NOs: 185-243 and 398-413. In certain other embodiments methods of the invention comprise the use of at least one set of primers i) and ii) comprising primers selected from SEQ ID NOs: 249-312 and 313-397 or selected from SEQ ID NOs: 249-312 and 398-482. In other embodiments methods of the invention comprise the use of at least one set of primers i) and ii) comprising primers selected from SEQ ID NOs: 249-312 and 313-329 or selected from SEQ ID NOs: 249-312 and 329-342. In other embodiments methods of the invention comprise the use of at least one set of primers i) and ii) comprising primers selected from SEQ ID NOs: 249-312 and 398-414 or selected from SEQ ID NOs: 249-312 and 414-427. In certain other embodiments methods of the invention comprise the use of at least one set of primers i) and ii) comprising primers SEQ ID NOs: 249-307 and 398-413. In still other embodiments methods of the invention comprise the use of at least one set of primers of i) and ii) comprising primers SEQ ID NOs: 249-307 and 313-328.

In some embodiments methods of the invention comprise the use of at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 398-482. In other embodiments methods of the invention comprise the use of at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 313-397. In some embodiments methods of the invention comprise the use of at least one set of primers i) and ii) comprising at least 50 primers selected from SEQ ID NOs: 185-248 and at least 10 primers, at least 12 primers, at least 14 primers, at least 16 primers, at least 18 primers, or at least 20 primers selected from SEQ ID NOs: 313-397. In other embodiments methods of the invention comprise the use of at least one set of primers i) and ii) comprising at least 50 primers selected from SEQ ID NOs: 185-248 and at least 10 primers, at least 12 primers, at least 14 primers, at least 16 primers, at least 18 primers, or at least 20 primers selected from SEQ ID NOs: 398-427.

In certain embodiments, provided is a method for amplification of rearranged genomic nucleic acid sequences of an immune receptor repertoire in a sample, comprising performing a multiplex amplification reaction to amplify rearranged immune receptor nucleic acid template molecules having a J gene portion and a V gene portion using at least one set of: i) a plurality of V gene primers directed to a majority of different V genes of at least one immune receptor coding sequence comprising at least a portion of framework region 1 (FR1) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein performing amplification using each set results in amplicons representing the entire repertoire of the respective immune receptor in the sample; thereby generating immune receptor amplicons comprising the repertoire of the immune receptor. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In some embodiments the one or more plurality of V gene primers of i) anneal to at least a portion of the FR1 region of the template molecules. In certain embodiments the plurality of J gene primers of ii) comprise at least ten primers that anneal to at least a portion of the J gene of the template molecules. In some embodiments the plurality of J gene primers of ii) comprises about 14 primers that anneal to at least a portion of the J gene portion of the template molecules. In some embodiments the plurality of J gene primers of ii) comprises about 16 primers that anneal to at least a portion of the J gene portion of the template molecules. In some embodiments the plurality of J gene primers of ii) comprises about 10 to about 20 primers that anneal to at least a portion of the J gene portion of the template molecules. In some embodiments the plurality of J gene primers of ii) comprises about 12 to about 18 primers that anneal to at least a portion of the J gene portion of the template molecules. In particular embodiments at least one set of the generated amplicons includes complementarity determining regions CDR1, CDR2, and CDR3 of an immune receptor gene sequence. In some embodiments the amplicons are about 220 to about 350 nucleotides in length, about 250 to about 325 nucleotides, or about 270 to about 300 nucleotides in length. In some embodiments the nucleic acid template used in methods is gDNA extracted from a biological sample.

In certain embodiments, methods are provided for providing sequence of the immune repertoire in a sample, comprising performing a multiplex amplification reaction to amplify rearranged immune receptor nucleic acid template molecules having a J gene portion and a V gene portion using at least one set of primers comprising i) a plurality of V gene primers directed to a majority of different V genes of at least one immune receptor coding sequence comprising at least a portion of framework region 1 (FR1) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. Sequencing of resulting immune receptor amplicon molecules is then performed and the sequences of the immune receptor amplicon molecules determined thereby provides sequence of the immune repertoire in the sample. In some embodiments, determining the sequence of the immune receptor amplicon molecules includes obtaining initial sequence reads, aligning the initial sequence read to a reference sequence, identifying productive reads, correcting one or more indel errors to generate rescued productive sequence reads, and determining the sequences of the resulting immune receptor molecules. In particular embodiments, determining the sequence of the immune receptor amplicon molecules includes obtaining initial sequence reads, adding the inferred J gene sequence to the sequence read to create an extended sequence read, aligning the extended sequence read to a reference sequence and identifying productive reads, identifying and correcting one or more indel errors in the V gene sequence to generate rescued productive sequence reads; and determining the sequences of the resulting immune receptor molecules. In particular embodiments the combination of productive reads and rescued productive reads is at least 40%, at least 50%, at least 60% at least 70% or at least 75% of the sequencing reads for the immune receptors. In additional embodiments the method further comprises sequence read clustering and immune receptor clonotype reporting. In some embodiments the average sequence read length is between about 200 and about 350 nucleotides, between about 225 and about 325 nucleotides, between about 250 and about 300 nucleotides, between about 270 and about 300 nucleotides, or between about 295 and about 325, depending in part on inclusion of any barcode sequence in the read length. In certain embodiments at least one set of the sequenced amplicons includes complementarity determining regions CDR1, CDR2, and CDR3 of a rearranged immune receptor sequence.

In particular embodiments, methods provided utilize target immune receptor primer sets comprising V gene primers wherein the one or more of a plurality of V gene primers are directed to sequences over an FR1 region about 70 nucleotides in length. In other certain embodiments the one or more of a plurality of V gene primers are directed to sequences over an FR1 region about 80 nucleotides in length. In other particular embodiments the one or more of a plurality of V gene primers are directed to sequences over an FR1 region about 50 nucleotides in length. In certain embodiments a target immune receptor primer set comprises V gene primers comprising about 45 to about 90 different FR1-directed primers. In some embodiments a target immune receptor primer set comprises V gene primers comprising about 50 to about 80 different FR1-directed primers. In some embodiments a target immune receptor primer set comprises V gene primers comprising about 55 to about 75 different FR1-directed primers. In some embodiments a target immune receptor primer set comprises V gene primers comprising about 60 to about 70 different FR1-directed primers. In some embodiments the target immune receptor primer set comprises a plurality of J gene primers. In some embodiments a target immune receptor primer set comprises at least ten J gene primers wherein each is directed to at least a portion of a J gene within target polynucleotides. In particular embodiments a target immune receptor primer set comprises at least 16 J gene primers wherein each is directed to at least a portion of a J gene within target polynucleotides. In some embodiments a target immune receptor primer set comprises about 10 to about 20 different J gene primers wherein each is directed to at least a portion of a J gene within target polynucleotides. In some embodiments a target immune receptor primer set comprises about 12, 13, 14, 15, 16, 17 or 18 different J gene primers. In particular embodiments a target immune receptor primer set comprises about 16 J gene primers wherein each is directed to at least a portion of a J gene within target polynucleotides. In particular embodiments a target immune receptor primer set comprises about 14 J gene primers wherein each is directed to at least a portion of a J gene within target polynucleotides.

In particular embodiments, methods of the invention comprise use of at least one set of primers comprising V gene primers i) and J gene primers ii) selected from Tables 2 and 5, respectively. In certain other embodiments methods of the invention comprise use of at least one set of primers i) and ii) comprising primers selected from SEQ ID NOs: 1-89 and 313-397 or selected from SEQ ID NOs: 90-180 and 398-482. In other embodiments methods of the invention comprise use of at least one set of primers i) and ii) comprising primers selected from SEQ ID NOs: 1-89 and 398-482 or selected from SEQ ID NOs: 90-180 and 313-397. In other embodiments methods of the invention comprise use of at least one set of primers i) and ii) comprising primers selected from SEQ ID NOs: 1-64 and 313-397 or selected from SEQ ID NOs: 1-64 and 398-482. In other embodiments methods of the invention comprise use of at least one set of primers i) and ii) comprising primers selected from SEQ ID NOs: 1-64 and 313-329 or selected from SEQ ID NOs: 1-64 and 329-342. In certain other embodiments methods of the invention comprise use of at least one set of primers i) and ii) comprising primers selected from SEQ ID NOs: 1-64 and 398-414 or selected from SEQ ID NOs: 1-64 and 414-427. In other embodiments methods of the invention comprise use of at least one set of primers of i) and ii) comprising primers SEQ ID NOs: 1-64 and 313-328. In still other embodiments methods of the invention comprise use of at least one set of primers of i) and ii) comprising primers SEQ ID NOs: 1-64 and 398-413. In other embodiments methods of the invention comprise use of at least one set of primers i) and ii) comprising primers selected from SEQ ID NOs: 90-180 and 313-342 or selected from SEQ ID NOs: 90-180 and 398-427. In other embodiments methods of the invention comprise use of at least one set of primers of i) and ii) comprising primers selected from SEQ ID NOs: 90-155 and 313-342. In still other embodiments methods of the invention comprise use of at least one set of primers of i) and ii) comprising primers selected from SEQ ID NOs: 90-155 and 398-427. In other embodiments methods of the invention comprise use of at least one set of primers of i) and ii) comprising primers selected from SEQ ID NOs: 90-155 and 398-414 or selected from SEQ ID NOs: 90-155 and 414-427. In other embodiments methods of the invention comprise use of at least one set of primers of i) and ii) comprising primers selected from SEQ ID NOs: 90-155 and 313-329 or selected from SEQ ID NOs: 90-155 and 329-342. In still other embodiments methods of the invention comprise use of at least one set of primers of i) and ii) comprising primers SEQ ID NOs: 90-153 and 398-413. In still other embodiments methods of the invention comprise use of at least one set of primers of i) and ii) comprising primers SEQ ID NOs: 90-153 and 313-328. In certain other embodiments methods of the invention comprise use of at least one set of primers of i) and ii) comprising primers selected from SEQ ID NOs: 90-92, 95-180 and 329-342 or selected from SEQ ID NOs: 90-92, 95-180 and 313-329. In still other embodiments methods of the invention comprise use of at least one set of primers of i) and ii) comprising primers selected from SEQ ID NOs: 90-92, 95-180, and 398-414 or selected from SEQ ID NOs: 90-92, 95-180 and 414-427. In other embodiments methods of the invention comprise use of at least one set of primers of i) and ii) comprising primers selected from SEQ ID NOs: 90-92, 95-180 and 398-413 or selected from SEQ ID NOs: 90-92, 95-180 and 398-427. In other embodiments methods of the invention comprise use of at least one set of primers of i) and ii) comprising primers SEQ ID NOs: 90-92, 95-180 and 398-413. In still other embodiments methods of the invention comprise use of at least one set of primers of i) and ii) comprising primers SEQ ID NOs: 90-92, 95-180, and 313-328.

In some embodiments methods of the invention comprise the use of at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 313-397. In other embodiments methods of the invention comprise the use of at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 398-482. In some embodiments methods of the invention comprise the use of at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 313-397. In other embodiments methods of the invention comprise the use of at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 398-482.

In some embodiments methods of the invention comprise the use of at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 313-342. In other embodiments methods of the invention comprise the use of at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 398-427. In some embodiments methods of the invention comprise the use of at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 313-342. In other embodiments methods of the invention comprise the use of at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 398-427.

In some embodiments methods of the invention comprise the use of at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 313-397. In other embodiments methods of the invention comprise the use of at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 398-482. In some embodiments methods of the invention comprise the use of at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 313-397. In other embodiments methods of the invention comprise the use of at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 398-482.

In some embodiments methods of the invention comprise the use of at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 313-342. In other embodiments methods of the invention comprise the use of at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 398-427. In some embodiments methods of the invention comprise the use of at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 313-342. In other embodiments methods of the invention comprise the use of at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 398-427.

In certain embodiments, provided is a method for amplification of rearranged genomic nucleic acid sequences of an immune receptor repertoire in a sample, comprising performing a multiplex amplification reaction to amplify rearranged immune receptor nucleic acid template molecules having a J gene portion and a V gene portion using at least one set of: i) a plurality of V gene primers directed to a majority of different V genes of at least one immune receptor coding sequence comprising at least a portion of framework region 2 (FR2) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein performing amplification using each set results in amplicons representing the entire repertoire of the respective immune receptor in the sample; thereby generating immune receptor amplicons comprising the repertoire of the immune receptor. In particular embodiments the one or more plurality of V gene primers of i) are directed to sequences over about an 80 nucleotide portion of the framework region. In more particular embodiments the one or more plurality of V gene primers of i) are directed to sequences over about a 50 nucleotide portion of the framework region. In some embodiments the one or more plurality of V gene primers of i) anneal to at least a portion of the FR2 region of the template molecules. In certain embodiments the plurality of J gene primers of ii) comprise at least ten primers that anneal to at least a portion of the J gene of the template molecules. In some embodiments the plurality of J gene primers of ii) comprises about 14 primers that anneal to at least a portion of the J gene portion of the template molecules. In some embodiments the plurality of J gene primers of ii) comprises about 16 primers that anneal to at least a portion of the J gene portion of the template molecules. In some embodiments the plurality of J gene primers of ii) comprises about 10 to about 20 primers that anneal to at least a portion of the J gene portion of the template molecules. In some embodiments the plurality of J gene primers of ii) comprises about 12 to about 18 primers that anneal to at least a portion of the J gene portion of the template molecules. In particular embodiments at least one set of the generated amplicons includes complementarity determining regions CDR2 and CDR3 of an immune receptor gene sequence. In some embodiments the amplicons are about 160 to about 270 nucleotides in length, about 180 to about 250 nucleotides, or about 195 to about 225 nucleotides in length. In some embodiments the nucleic acid template used in methods is gDNA extracted from a biological sample.

In certain embodiments, methods are provided for providing sequence of the immune repertoire in a sample, comprising performing a multiplex amplification reaction to amplify rearranged immune receptor nucleic acid template molecules having a J gene portion and a V gene portion using at least one set of primers comprising i) a plurality of V gene primers directed to a majority of different V genes of at least one immune receptor coding sequence comprising at least a portion of framework region 2 (FR2) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. Sequencing of resulting immune receptor amplicon molecules is then performed and the sequences of the immune receptor amplicon molecules determined thereby provides sequence of the immune repertoire in the sample. In particular embodiments, determining the sequence of the immune receptor amplicon molecules includes obtaining initial sequence reads, adding the inferred J gene sequence to the sequence read to create an extended sequence read, aligning the extended sequence read to a reference sequence and identifying productive reads, identifying and correcting one or more indel errors in the V gene sequence to generate rescued productive sequence reads; and determining the sequences of the resulting immune receptor molecules. In particular embodiments the combination of productive reads and rescued productive reads is at least 40%, at least 50%, at least 60% at least 70% or at least 75% of the sequencing reads for the immune receptors. In additional embodiments the method further comprises sequence read clustering and immune receptor clonotype reporting. In some embodiments the average sequence read length is between about 160 and about 300 nucleotides, between about 180 and about 280 nucleotides, between about 200 and about 260 nucleotides, or between about 225 and about 270 nucleotides, depending in part on inclusion of any barcode sequence in the read length. In certain embodiments at least one set of the sequenced amplicons includes complementarity determining regions CDR2 and CDR3 of a rearranged immune receptor sequence.

In particular embodiments, methods provided utilize target immune receptor primer sets comprising V gene primers wherein the one or more of a plurality of V gene primers are directed to sequences over an FR2 region about 70 nucleotides in length. In other particular embodiments the one or more of a plurality of V gene primers are directed to sequences over an FR2 region about 50 nucleotides in length. In certain embodiments a target immune receptor primer set comprises V gene primers comprising about 45 to about 90 different FR2-directed primers. In some embodiments a target immune receptor primer set comprises V gene primers comprising about 30 to about 60 different FR2-directed primers. In some embodiments a target immune receptor primer set comprises V gene primers comprising about 20 to about 50 different FR2-directed primers. In some embodiments a target immune receptor primer set comprises V gene primers comprising about 60 to about 70 different FR2-directed primers. In some embodiments a target immune receptor primer set comprises V gene primers comprising about 20 to about 30 different FR2-directed primers. In some embodiments the target immune receptor primer set comprises a plurality of J gene primers. In some embodiments a target immune receptor primer set comprises at least ten J gene primers wherein each is directed to at least a portion of a J gene within target polynucleotides. In particular embodiments a target immune receptor primer set comprises at least 16 J gene primers wherein each is directed to at least a portion of a J gene within target polynucleotides. In some embodiments a target immune receptor primer set comprises about 10 to about 20 different J gene primers wherein each is directed to at least a portion of a J gene within target polynucleotides. In some embodiments a target immune receptor primer set comprises about 12, 13, 14, 15, 16, 17 or 18 different J gene primers. In particular embodiments a target immune receptor primer set comprises 16 J gene primers wherein each is directed to at least a portion of a J gene within target polynucleotides. In particular embodiments a target immune receptor primer set comprises 14 J gene primers wherein each is directed to at least a portion of a J gene within target polynucleotides.

In particular embodiments, methods of the invention comprise use of at least one set of primers comprising V gene primers i) and J gene primers ii) selected from Tables 4 and 5, respectively. In certain other embodiments methods of the invention comprise use of at least one set of primers i) and ii) comprising primers selected from SEQ ID NOs: 483-505 and 313-397 or selected from SEQ ID NOs: 483-505 and 398-482. In some embodiments methods of the invention comprise use of at least one set of primers i) and ii) comprising primers selected from SEQ ID NOs: 483-505 and 313-342 or selected from SEQ ID NOs: 483-505 and 398-427. In other embodiments methods of the invention comprise use of at least one set of primers i) and ii) comprising primers selected from SEQ ID NOs: 483-505 and 313-329 or selected from SEQ ID NOs: 483-505 and 329-342. In other embodiments methods of the invention comprise use of at least one set of primers i) and ii) comprising primers selected from SEQ ID NOs: 483-505 and 398-414 or selected from SEQ ID NOs: 483-505 and 414-427. In other embodiments methods of the invention comprise use of at least one set of primers i) and ii) comprising primers SEQ ID NOs: 483-505 and 313-328. In certain other embodiments methods of the invention comprise use of at least one set of primers i) and ii) comprising primers SEQ ID NOs: 483-505 and 398-413.

In some embodiments methods of the invention comprise the use of at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 313-397. In other embodiments methods of the invention comprise the use of at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 398-482. In some embodiments methods of the invention comprise the use of at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 313-342. In other embodiments methods of the invention comprise the use of at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 398-427.

In certain embodiments, methods of the invention comprise use of a biological sample selected from the group consisting of hematopoietic cells, lymphocytes, and tumor cells. In some embodiments the biological sample is selected from the group consisting of peripheral blood mononuclear cells (PBMCs), T cells, B cells, circulating tumor cells, and tumor infiltrating lymphocytes (herein "TILs" or "TIL"). In some embodiments, the biological sample comprises cells selected from the group consisting of PBMCs, T cells, B cells, circulating tumor cells, and TILs. In some embodiments, the biological sample comprises cell-free DNA, such as found, for example, in blood or plasma. In some embodiments, the biological sample comprises T cells undergoing ex vivo activation and/or expansion.

In some embodiments, methods, compositions, and systems are provided for determining the immune repertoire of a biological sample by assessing both rearranged immune receptor gDNA and expressed immune receptor RNA from the sample. Genomic DNA of a sample may be assessed for rearranged immune receptor genes using the methods, compositions, and systems provided herein. The sample RNA may be assessed for expressed immune receptor sequences using the methods, composition, and systems described in the co-owned U.S. Provisional Application Nos. 62/553,736, filed Sep. 1, 2017, and 62/586,099 filed Nov. 14, 2017, each entitled "Compositions and Methods for Immune Repertoire Sequencing", the entirety of each is incorporated herein by reference. In some embodiments, the sample RNA and gDNA may be assessed concurrently and following reverse transcription of the RNA to form cDNA, the cDNA and gDNA may be amplified in the same multiplex amplification reaction. In some embodiments, cDNA from the sample RNA and the sample gDNA may undergo multiplex amplification in separate reactions. In some embodiments, cDNA from the sample RNA and sample gDNA may undergo multiplex amplification with parallel primer pools. In some embodiments, the same immune receptor-directed primer pools are used to assess the immune repertoire of gDNA and RNA from the sample. In some embodiments, the different immune receptor-directed primer pools are used to assess the immune repertoire of gDNA and RNA from the sample.

In some embodiments, the methods and compositions provided are used to identify and/or characterize an immune repertoire of a subject. In some embodiments, methods and compositions provided are used to identify and characterize novel TCR or BCR alleles of a subject's immune repertoire. In some embodiments, the sequences of the identified immune repertoire are compared to a contemporaneous or current version of the IMGT database and the sequence of at least one allelic variant absent from that IMGT database is identified. Characterizing the existence of undocumented TRB polymorphism, for example, may help with understanding factors that influence autoimmune disease and response to immunotherapy. Thus, in some embodiments, methods and compositions are provided to identify novel TRBV gene allele polymorphisms and allelic variants that may predict or detect autoimmune disease or immune-mediated adverse events. In other embodiments, provided are methods for making recombinant nucleic acids encoding identified novel TRBV allelic variants. In some embodiments, provided are methods for making recombinant TRBV allelic variant molecules and for making recombinant cells which express the same.

In some embodiments, methods and compositions provided are used to identify and characterize novel TCR or BCR alleles of a subject's immune repertoire. In some embodiments, a patient's immune repertoire may be identified or characterized before and/or after a therapeutic treatment, for example treatment for a cancer or immune disorder. In some embodiments, identification or characterization of an immune repertoire may be used to assess the effect or efficacy of a treatment, to modify therapeutic regimens, and to optimize the selection of therapeutic agents. In some embodiments, identification or characterization of the immune repertoire may be used to assess a patient's response to an immunotherapy, e.g., CAR (chimeric antigen receptor)-T cell therapy, a cancer vaccine and/or other immune-based treatment or combination(s) thereof. In some embodiments, identification or characterization of the immune repertoire may indicate a patient's likelihood to respond to a therapeutic agent or may indicate a patient's likelihood to not be responsive to a therapeutic agent.

In some embodiments, a patient's immune repertoire may be identified or characterized to monitor progression and/or treatment of hyperproliferative diseases, including detection of residual disease following patient treatment, monitor progression and/or treatment of autoimmune disease, transplantation monitoring, and to monitor conditions of antigenic stimulation, including following vaccination, exposure to bacterial, fungal, parasitic, or viral antigens, or infection by bacteria, fungi, parasites or virus. In some embodiments, identification or characterization of the immune repertoire may be used to assess a patient's response to an anti-infective or anti-inflammatory therapy.

In certain embodiments, the methods and compositions provided are used to monitor changes in immune repertoire clonal populations, for example changes in clonal expansion, changes in clonal contraction, and changes in relative ratios of clones or clonal populations. In some embodiments, the provided methods and compositions are used to monitor changes in immune repertoire clonal populations (e.g., clonal expansion, clonal contraction, changes in relative ratios) in response to tumor growth. In some embodiments, the provided methods and compositions are used to monitor changes in immune repertoire clonal populations (e.g., clonal expansion, clonal contraction, changes in relative ratios) in response to tumor treatment. In some embodiments, the provided methods and compositions provided are used to monitor changes in immune repertoire clonal populations (e.g., clonal expansion, clonal contraction, changes in relative ratios) during a remission period. For many lymphoid malignancies, a clonal B cell receptor or T cell receptor sequence can be used a biomarker for the malignant cells of the particular cancer (e.g., leukemia) and to monitor residual disease, tumor expansion, contraction, and/or treatment response. In certain embodiments a clonal B cell receptor or T cell receptor may be identified and further characterized to confirm a new utility in therapeutic, biomarker and/or diagnostic use.

In some embodiments, methods and compositions are provided for identifying and/or characterizing immune repertoire clonal populations in a sample from a subject, comprising performing one or more multiplex amplification reactions with the sample or with gDNA prepared from the sample to amplify rearranged immune repertoire nucleic acid template molecules having a J gene portion and a V gene portion using at least one set of primers comprising i) a plurality of V gene primers directed to a majority of different V genes of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying one or more immune repertoire clonal populations for the target immune receptor from the sample. In particular, embodiments determining the sequence of the immune receptor amplicon molecules includes obtaining initial sequence reads, adding the inferred J gene sequence to the sequence read to create an extended sequence read, aligning the extended sequence read to a reference sequence and identifying productive reads, identifying and correcting one or more indel errors in the V gene sequence to generate rescued productive sequence reads, and determining the sequences of the resulting immune receptor molecules. In other embodiments of such methods and compositions, the multiplex amplification reaction is performed using at least one set of primers comprising i) a plurality of FR1- or FR2-directed V gene primers, the plurality directed to a majority of different V genes of at least one immune receptor coding sequence comprising at least a portion of FR1 or at least a portion of FR2 within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor.

In some embodiments, methods and compositions are provided for monitoring changes in immune repertoire clonal populations in a subject, comprising performing one or more multiplex amplification reactions with a subject's sample to amplify rearranged immune repertoire nucleic acid template molecules having a J gene portion and a V gene portion using at least one set of FR3-, FR2- or FR1-directed primers, the set directed to a majority of different V genes of at least one immune receptor coding sequence comprising at least a portion of FR3, FR2 or FR1 within the V gene, and ii) a plurality of J gene primers directed to a majority of different J genes of the respective target immune receptor coding sequence, sequencing the resultant immune receptor amplicons, identifying immune repertoire clonal populations for the target immune receptor from the sample, and comparing the identified immune repertoire clonal populations to those identified in samples obtained from the subject at a different time. In various embodiments, the one or more multiplex amplification reactions performed in such methods may be a single multiplex amplification reaction or may be two or more multiplex amplification reactions performed in parallel, for example parallel, highly multiplexed amplification reactions performed with different primer pools. Samples for use in monitoring changes in immune repertoire clonal populations include, without limitation, samples obtained prior to a diagnosis, samples obtained at any stage of diagnosis, samples obtained during a remission, samples obtained at any time prior to a treatment (pre-treatment sample), samples obtained at any time following completion of treatment (post-treatment sample), and samples obtained during the course of treatment.

In certain embodiments, methods and compositions are provided for identifying and/or characterizing the immune repertoire of a patient to monitor progression and/or treatment of the patient's hyperproliferative disease. In some embodiments, the methods and compositions provided are used for minimal residual disease (MRD) monitoring for a patient following treatment. In some embodiments, the methods and compositions are used to identify and/or track B cell lineage malignancies or T cell lineage malignancies. In some embodiments, the methods and compositions are used to detect and/or monitor MRD in patients diagnosed with leukemia or lymphoma, including without limitation, acute lymphoblastic leukemia, chronic myeloid leukemia, chronic lymphocytic leukemia, chronic myelogenous leukemia, cutaneous T cell lymphoma, B cell lymphoma, mantle cell lymphoma, and multiple myeloma. In some embodiments, the methods and compositions are used to detect and/or monitor MRD in patients diagnosed with solid tumors, including without limitation, breast cancer, lung cancer, colorectal, and neuroblastoma. In some embodiments, the methods and compositions are used to detect and/or monitor MRD in patients following cancer treatment including without limitation bone marrow transplant, lymphocyte infusion, adoptive T-cell therapy, other cell-based immunotherapy, and antibody-based immunotherapy.

In some embodiments, methods and compositions are provided for identifying and/or characterizing the immune repertoire of a patient to monitor progression and/or treatment of the patient's hyperproliferative disease, comprising performing one or more multiplex amplification reactions with a sample from the patient or with gDNA prepared from the sample to amplify rearranged immune repertoire nucleic acid template molecules having a J gene portion and a V gene portion using at least one set of primers comprising i) a plurality of V gene primers directed to a majority of different V genes of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying immune repertoire for the target immune receptor from the sample. In particular, embodiments determining the sequence of the immune receptor amplicon molecules includes obtaining initial sequence reads, adding the inferred J gene sequence to the sequence read to create an extended sequence read, aligning the extended sequence read to a reference sequence and identifying productive reads, identifying and correcting one or more indel errors in the V gene sequence to generate rescued productive sequence reads; and determining the sequences of the resulting immune receptor molecules. In other embodiments of such methods and compositions, the multiplex amplification reaction is performed using at least one set of primers comprising i) a plurality of FR1- or FR2-directed V gene primers, the plurality directed to a majority of different V genes of at least one immune receptor coding sequence comprising at least a portion of FR1 or FR2 within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor.

In some embodiments, methods and compositions are provided for MRD monitoring for a patient having a hyperproliferative disease, comprising performing one or more multiplex amplification reactions with a patient's sample to amplify rearranged immune repertoire nucleic acid template molecules having a J gene portion and a V gene portion using at least one set of FR3-, FR2- or FR1-directed primers, the set directed to a majority of different V genes of at least one immune receptor coding sequence comprising at least a portion of FR3, FR2 or FR1 within the V gene, and ii) a plurality of J gene primers directed to a majority of different J genes of the respective target immune receptor coding sequence, sequencing the resultant immune receptor amplicons, identifying immune repertoire sequences for the target immune receptor, and detecting the presence or absence of immune receptor sequence(s) in the sample associated with the hyperproliferative disease. In various embodiments, the one or more multiplex amplification reactions performed in such methods may be a single multiplex amplification reaction or may be two or more multiplex amplification reactions performed in parallel, for example parallel, highly multiplexed amplification reactions performed with different primer pools. Samples for use in MRD monitoring include, without limitation, samples obtained during a remission, samples obtained at any time following completion of treatment (post-treatment sample), and samples obtained during the course of treatment.

In certain embodiments, methods and compositions are provided for identifying and/or characterizing the immune repertoire of a subject in response to a treatment. In some embodiments, the methods and compositions are used to characterize and/or monitor populations or clones of tumor infiltrating lymphocytes (TILs) before, during, and/or following tumor treatment. In some embodiments, the methods and compositions for determining immune repertoire are used to identify and/or track therapeutic T cell population(s) and B cell population(s). In some embodiments, the methods and compositions provided are used to identify and/or monitor the persistence of cell-based therapies following patient treatment, including but not limited to, presence (e.g., persistent presence) of engineered T cell populations including without limitation CAR-T cell populations, TCR engineered T cell populations, persistent CAR-T expression, presence (e.g., persistent presence) of administered TIL populations, TIL expression (e.g., persistent expression) following adoptive T-cell therapy, and/or immune reconstitution after allogeneic hematopoietic cell transplantation.

In some embodiments, the methods and compositions provided are used to characterize and/or monitor T cell clones or populations present in patient sample following administration of cell-based therapies to the patient, including but not limited to, e.g., cancer vaccine cells, CAR-T, TIL, and/or other engineered T cell-based therapy. In some embodiments, the provided methods and compositions are used to characterize and/or monitor immune repertoire in a patient sample following cell-based therapies in order to assess and/or monitor the patient's response to the administered cell-based therapy. Samples for use in such characterizing and/or monitoring following cell-based therapy include, without limitation, circulating blood cells, circulating tumor cells, TILs, tissue, and tumor sample(s) from a patient.

In some embodiments, methods and compositions are provided for monitoring T cell-based therapy for a patient receiving such therapy, comprising performing one or more multiplex amplification reactions with a patient's sample to amplify rearranged immune repertoire nucleic acid template molecules having a J gene portion and a V gene portion using at least one set of primers FR3-, FR2- or FR1-directed primers, the set directed to a majority of different V genes of at least one immune receptor coding sequence comprising at least a portion of FR3, FR2 or FR1 within the V gene, and ii) a plurality of J gene primers directed to a majority of different J genes of the respective target immune receptor coding sequence, sequencing the resultant immune receptor amplicons, identifying immune repertoire sequences for the target immune receptor, and detecting the presence or absence of immune receptor sequence(s) in the sample associated with the T cell-based therapy.

In some embodiments, methods and compositions are provided for monitoring a patient's response following administration of a T cell-based therapy, comprising performing one or more multiplex amplification reactions with a patient's sample to amplify rearranged immune repertoire nucleic acid template molecules having a J gene portion and a V gene portion using at least one set of FR3-, FR2- or FR1-directed primers, the set directed to a majority of different V genes of at least one immune receptor coding sequence comprising at least a portion of FR3, FR2 or FR1 within the V gene, and ii) a plurality of J gene primers directed to a majority of different J genes of the respective target immune receptor coding sequence, sequencing the resultant immune receptor amplicons, identifying immune repertoire sequences for the target immune receptor, and comparing the identified immune repertoire to the immune receptor sequence(s) identified in samples obtained from the patient at a different time. T cell-based therapies suitable for such monitoring include, without limitation, CAR-T cells, TCR engineered T cells, TILs, and other enriched autologous T cells. In various embodiments, the one or more multiplex amplification reactions performed in such monitoring methods may be a single multiplex amplification reaction or may be two or more multiplex amplification reactions performed in parallel, for example parallel, highly multiplexed amplification reactions performed with different primer pools. Samples for use in such monitoring include, without limitation, samples obtained prior to a diagnosis, samples obtained at any stage of diagnosis, samples obtained during a remission, samples obtained at any time prior to a treatment (pre-treatment sample), samples obtained at any time following completion of treatment (post-treatment sample), and samples obtained during the course of treatment.

In some embodiments, the methods and compositions for determining T cell and/or B cell receptor repertoires are used to measure and/or assess immunocompetence before, during, and/or following a treatment, including without limitation, solid organ transplant or bone marrow transplant. For example, the diversity of the T cell receptor beta repertoire can be used to measure immunocompetence and immune cell reconstitution following a hematopoietic stem cell transplant treatment. Also, the rate of change in diversity of the TRB repertoire between time points following a transplant can be used to modify patient treatment.

In some embodiments, methods and compositions are provided for identifying and/or characterizing the immune repertoire of a subject in response to a treatment, comprising obtaining a sample from the subject following initiation of a treatment, performing one or more multiplex amplification reactions with the sample or with gDNA prepared from the sample to amplify rearranged immune repertoire nucleic acid template molecules having a J gene portion and a V gene portion using at least one set of primers comprising i) a plurality of V gene primers directed to a majority of different V genes of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules.

The method further comprises sequencing the resulting immune receptor amplicon molecules, determining the sequences of the immune receptor amplicon molecules, and identifying immune repertoire for the target immune receptor from the sample. In some embodiments, the method further comprises comparing the identified immune repertoire from the sample obtained following treatment initiation to the immune repertoire from a sample of the patient obtained prior to treatment. In particular, embodiments determining the sequence of the immune receptor amplicon molecules includes obtaining initial sequence reads, adding the inferred J gene sequence to the sequence read to create an extended sequence read, aligning the extended sequence read to a reference sequence and identifying productive reads, identifying and correcting one or more indel errors in the V gene sequence to generate rescued productive sequence reads; and determining the sequences of the resulting immune receptor molecules. In other embodiments of such methods and compositions, the multiplex amplification reaction is performed using at least one set of primers comprising i) a plurality of FR1- or FR2-directed V gene primers, the plurality directed to a majority of different V genes of at least one immune receptor coding sequence comprising at least a portion of FR1 or FR2 within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor.

In some embodiments, methods and compositions are provided for monitoring changes in the immune repertoire of a subject in response to a treatment, comprising performing one or more multiplex amplification reactions with a subject's or patient's sample to amplify rearranged immune repertoire nucleic acid template molecules having a J gene portion and a V gene portion using at least one set of FR3-, FR2- or FR1-directed primers, the set directed to a majority of different V genes of at least one immune receptor coding sequence comprising at least a portion of FR3, FR2 or FR1 within the V gene, and ii) a plurality of J gene primers directed to a majority of different J genes of the respective target immune receptor coding sequence, sequencing the resultant immune receptor amplicons, identifying immune repertoire sequences for the target immune receptor from the sample, and comparing the identified immune repertoire to those identified in samples obtained from the subject at a different time. In various embodiments, the one or more multiplex amplification reactions performed in such methods may be a single multiplex amplification reaction or may be two or more multiplex amplification reactions performed in parallel, for example parallel, highly multiplexed amplification reactions performed with different primer pools. Samples for use in monitoring changes in immune repertoire include, without limitation, samples obtained prior to a diagnosis, samples obtained at any stage of diagnosis, samples obtained during a remission, samples obtained at any time prior to a treatment (pre-treatment sample), samples obtained at any time following completion of treatment (post-treatment sample), and samples obtained during the course of treatment.

In certain embodiments, the methods and compositions provided are used to characterize and/or monitor immune repertoires associated with immune system-mediated adverse event(s), including without limitation, those associated with inflammatory conditions, autoimmune reactions, and/or autoimmune diseases or disorders. In some embodiments, the methods and compositions provided are used to identify and/or monitor T cell and/or B cell immune repertoires associated with chronic autoimmune diseases or disorders including, without limitation, multiple sclerosis, Type I diabetes, narcoplesy, rheumatoid arthritis, ankylosing spondylitis, asthma, and SLE. In some embodiments, a systemic sample, such as a blood sample, is used to determine the immune repertoire(s) of an individual with an autoimmune condition. In some embodiments, a localized sample, such as a fluid sample from an affected joint or region of swelling, is used to determine the immune repertoire(s) of an individual with an autoimmune condition. In some embodiments, comparison of the immune repertoire found in a localized or affected area sample to the immune repertoire found in the systemic sample can identify clonal T or B cell populations to be targeted for removal.

In some embodiments, methods and compositions are provided for identifying and/or monitoring an immune repertoire associated with a patient's immune system-mediated adverse event(s), comprising performing one or more multiplex amplification reactions with a sample from the patient or with gDNA prepared from the sample to amplify rearranged immune repertoire nucleic acid template molecules having a J gene portion and a V gene portion using at least one set of primers comprising i) a plurality of V gene primers directed to a majority of different V genes of at least one immune receptor coding sequence comprising at least a portion of framework region 3 (FR3) within the V gene, and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor thereby generating immune receptor amplicon molecules. The method further comprises sequencing the resulting immune receptor amplicon molecules, determining the sequences of the immune receptor amplicon molecules, and identifying immune repertoire for the target immune receptor from the sample. In some embodiments, the method further comprises comparing the identified immune repertoire from the sample to an identified immune repertoire from a sample from the patient obtained at a different time. In particular, embodiments determining the sequence of the immune receptor amplicon molecules includes obtaining initial sequence reads, adding the inferred J gene sequence to the sequence read to create an extended sequence read, aligning the extended sequence read to a reference sequence and identifying productive reads, identifying and correcting one or more indel errors in the V gene sequence to generate rescued productive sequence reads; and determining the sequences of the resulting immune receptor molecules. In other embodiments of such methods and compositions, the multiplex amplification reaction is performed using at least one set of primers comprising i) a plurality of FR1- or FR2-directed V gene primers directed to a majority of different V genes of at least one immune receptor coding sequence comprising at least a portion of FR1 or FR2 within the V gene, and ii) a plurality of J gene primers directed to a majority of different J genes of the respective immune receptor coding sequence, wherein each set of i) and ii) primers directed to the same target immune receptor sequences is selected from the group consisting of a T cell receptor and an antibody receptor.

In some embodiments, methods and compositions are provided for identifying and/or monitoring an immune repertoire associated with progression and/or treatment of a patient's immune system-mediated adverse event(s), comprising performing one or more multiplex amplification reactions with a patient's sample to amplify rearranged immune repertoire nucleic acid template molecules having a J gene portion and a V gene portion using at least one set of FR3-, FR2- or FR1-directed primers, the set directed to a majority of different V genes of at least one immune receptor coding sequence comprising at least a portion of FR3, FR2 or FR1 within the V gene, and ii) a plurality of J gene primers directed to a majority of different J genes of the respective target immune receptor coding sequence, sequencing the resultant immune receptor amplicons, identifying immune repertoire sequences for the target immune receptor from the sample, and comparing the identified immune repertoire to the immune repertoire(s) identified in samples obtained from the patient at a different time. In various embodiments, the one or more multiplex amplification reactions performed in such methods may be a single multiplex amplification reaction or may be two or more multiplex amplification reactions performed in parallel, for example parallel, highly multiplexed amplification reactions performed with different primer pools. Samples for use in monitoring changes in immune repertoire associated with immune system-mediated adverse event(s) include, without limitation, samples obtained prior to a diagnosis, samples obtained at any stage of diagnosis, samples obtained during a remission, samples obtained at any time prior to a treatment (pre-treatment sample), samples obtained at any time following completion of treatment (post-treatment sample), and samples obtained during the course of treatment.

In some embodiments, the methods and compositions provided are used to characterize and/or monitor immune repertoires associated with passive immunity, including naturally acquired passive immunity and artificially acquired passive immunity therapies. For example, the methods and compositions provided may be used to identify and/or monitor protective antibodies that provide passive immunity to the recipient following transfer of antibody-mediated immunity to the recipient, including without limitation, antibody-mediated immunity conveyed from a mother to a fetus during pregnancy or to an infant through breast-feeding, or conveyed via administration of antibodies to a recipient. In another example, the methods and compositions provided may be used to identify and/or monitor B cell and/or T cell immune repertoires associated with passive transfer of cell-mediated immunity to a recipient, such as the administration of mature circulating lymphocytes to a recipient histocompatible with the donor. In some embodiments, the methods and compositions provided are used to monitor the duration of passive immunity in a recipient.

In some embodiments, the methods and compositions provided are used to characterize and/or monitor immune repertoires associated with active immunity or vaccination therapies. For example, following exposure to a vaccine or infectious agent, the methods and compositions provided may be used to identify and/or monitor protective antibodies or protective clonal B cell or T cell populations that may provide active immunity to the exposed individual. In some embodiments, the methods and compositions provided are used to monitor the duration of B or T cell clones which contribute to immunity in an exposed individual. In some embodiments, the methods and compositions provided are used to identify and/or monitor B cell and/or T cell immune repertoires associated with exposure to bacterial, fungal, parasitic, or viral antigens. In some embodiments, the methods and compositions provided are used to identify and/or monitor B cell and/or T cell immune repertoires associated with bacterial, fungal, parasitic, or viral infection.

In some embodiments, the methods and compositions provided are used to screen or characterize lymphocyte populations which are grown and/or activated in vitro for use as immunotherapeutic agents or in immunotherapeutic-based regimens. In some embodiments, the methods and compositions provided are used to screen or characterize TIL populations or other harvested T cell populations which are grown and/or activated in vitro, for example, TILs or other harvested T cells grown and/or activated for use in adoptive immunotherapy. In some embodiments, the methods and compositions provided are used to screen or characterize CAR-T populations or other engineered T cell populations which are grown and/or activated in vitro, for use, for example, in immunotherapy.

In some embodiments, the methods and compositions provided are used to assess cell populations by monitoring immune repertoires during ex vivo workflows for manufacturing engineered T cell preparations, for example, for quality control or regulatory testing purposes.

In some embodiments, the sequences of novel TCR or BCR alleles identified as described herein may be used to generate recombinant TCR or BCR nucleic acids or molecules. Such novel sequence information and amplicons can be used to generate new recombinant TRB allelic variants and/or nucleic acids encoding the same.

In some embodiments, the methods and compositions provided are used in the screening and/or production of recombinant antibody libraries. Compositions provided which are directed to identifying BCRs can be used to rapidly evaluate recombinant antibody library size and composition to identify antibodies of interest.

In some embodiments, profiling immune receptor repertoires as provided herein may be combined with profiling immune response gene expression to provide characterization of the tumor microenvironment. In some embodiments, combining or correlating a tumor sample's immune receptor repertoire profile with a targeted immune response gene expression profile provides a more thorough analysis of the tumor microenvironment and may suggest or provide guidance for immunotherapy treatments.

Suitable cells for analysis include, without limitation, various hematopoietic cells, lymphocytes, and tumor cells, such as peripheral blood mononuclear cells (PBMCs), T cells, B cells, circulating tumor cells, and tumor infiltrating lymphocytes (TILs). Lymphocytes expressing immunoglobulin include pre-B cells, B-cells, e.g. memory B cells, and plasma cells. Lymphocytes expressing T cell receptors include thymocytes, NK cells, pre-T cells and T cells, where many subsets of T cells are known in the art, e.g. Th1, Th2, Th17, CTL, T reg, etc. For example, in some embodiments, a sample comprising PBMCs may be used as a source for TCR and/or antibody immune repertoire analysis. The sample may contain, for example, lymphocytes, monocytes, and macrophages as well as antibodies and other biological constituents.

Analysis of the immune repertoire is of interest for conditions involving cellular proliferation and antigenic exposure, including without limitation, the presence of cancer, exposure to cancer antigens, exposure to antigens from an infectious agent, exposure to vaccines, exposure to allergens, exposure to food stuffs, presence of a graft or transplant, and the presence of autoimmune activity or disease. Conditions associated with immunodeficiency are also of interest for analysis, including congenital and acquired immunodeficiency syndromes.

B cell lineage malignancies of interest include, without limitation, multiple myeloma; acute lymphocytic leukemia (ALL); relapsed/refractory B cell ALL, chronic lymphocytic leukemia (CLL); diffuse large B cell lymphoma; mucosa-associated lymphatic tissue lymphoma (MALT); small cell lymphocytic lymphoma; mantle cell lymphoma (MCL); Burkitt lymphoma; mediastinal large B cell lymphoma; Waldenström macroglobulinemia; nodal marginal zone B cell lymphoma (NMZL); splenic marginal zone lymphoma (SMZL); intravascular large B-cell lymphoma; primary effusion lymphoma; lymphomatoid granulomatosis, etc. Non-malignant B cell hyperproliferative conditions include monoclonal B cell lymphocytosis (MBL).

T cell lineage malignancies of interest include, without limitation, precursor T-cell lymphoblastic lymphoma; T-cell prolymphocytic leukemia; T-cell granular lymphocytic leukemia; aggressive NK cell leukemia; adult T-cell lymphoma/leukemia (HTLV 1-positive); extranodal NK/T-cell lymphoma; enteropathy-type T-cell lymphoma; hepatosplenic γδ T-cell lymphoma; subcutaneous panniculitis-like T-cell lymphoma; mycosis fungoides/Sezary syndrome; anaplastic large cell lymphoma, T/null cell; peripheral T-cell lymphoma; angioimmunoblastic T-cell lymphoma; chronic lymphocytic leukemia (CLL); acute lymphocytic leukemia (ALL); prolymphocytic leukemia; and hairy cell leukemia.

Other malignancies of interest include, without limitation, acute myeloid leukemia, head and neck cancers, brain cancer, breast cancer, ovarian cancer, cervical cancer, colorectal cancer, endometrial cancer, gallbladder cancer, gastric cancer, bladder cancer, prostate cancer, testicular cancer, liver cancer, lung cancer, kidney (renal cell) cancer, esophageal cancer, pancreatic cancer, thyroid cancer, bile duct cancer, pituitary tumor, wilms tumor, kaposi sarcoma, osteosarcoma, thymus cancer, skin cancer, heart cancer, oral and larynx cancer, neuroblastoma and non-hodgkin lymphoma.

Neurological inflammatory conditions are of interest, e.g. Alzheimer's Disease, Parkinson's Disease, Lou Gehrig's Disease, etc. and demyelinating diseases, such as multiple sclerosis, chronic inflammatory demyelinating polyneuropathy, etc. as well as inflammatory conditions such as rheumatoid arthritis. Systemic lupus erythematosus (SLE) is an autoimmune disease characterized by polyclonal B cell activation, which results in a variety of anti-protein and non-protein autoantibodies (see Kotzin et al. (1996) Cell 85:303-306). These autoantibodies form immune complexes that deposit in multiple organ systems, causing tissue damage. An autoimmune component may be ascribed to atherosclerosis, where candidate autoantigens include Hsp60, oxidized LDL, and 2-Glycoprotein I (2GPI).

A sample for use in the methods described herein may be one that is collected from a subject with a malignancy or hyperproliferative condition, including lymphomas, leukemias, and plasmacytomas. A lymphoma is a solid neoplasm of lymphocyte origin, and is most often found in the lymphoid tissue. Thus, for example, a biopsy from a lymph node, e.g. a tonsil, containing such a lymphoma would constitute a suitable biopsy. Samples may be obtained from a subject or patient at one or a plurality of time points in the progression of disease and/or treatment of the disease.

In some embodiments, the disclosure provides methods for performing target-specific multiplex PCR on a gDNA sample having a plurality of rearranged immune receptor target sequences using primers having a cleavable group.

In certain embodiments, library and/or template preparation to be sequenced are prepared automatically from a population of nucleic acid samples using the compositions provided herein using an automated systems, e.g., the Ion Chef™ system.

As used herein, the term "subject" includes a person, a patient, an individual, someone being evaluated, etc.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or.

As used herein, "antigen" refers to any substance that, when introduced into a body, e.g., of a subject, can stimulate an immune response, such as the production of an antibody or T cell receptor that recognizes the antigen. Antigens include molecules such as nucleic acids, lipids, ribonucleoprotein complexes, protein complexes, proteins, polypeptides, peptides and naturally occurring or synthetic modifications of such molecules against which an immune response involving T and/or B lymphocytes can be generated. With regard to autoimmune disease, the antigens herein are often referred to as autoantigens. With regard to allergic disease the antigens herein are often referred to as allergens. Autoantigens are any molecule produced by the organism that can be the target of an immunologic response, including peptides, polypeptides, and proteins encoded within the genome of the organism and post-translationally-generated modifications of these peptides, polypeptides, and proteins. Such molecules also include carbohydrates, lipids and other molecules produced by the organism. Antigens also include vaccine antigens, which include, without limitation, pathogen antigens, cancer associated antigens, allergens, and the like.

As used herein, "amplify", "amplifying" or "amplification reaction" and their derivatives, refer to any action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. In some embodiments, amplification includes a template-dependent in vitro enzyme-catalyzed reaction for the production of at least one copy of at least some portion of the nucleic acid molecule or the production of at least one copy of a nucleic acid sequence that is complementary to at least some portion of the nucleic acid molecule. Amplification optionally includes linear or exponential replication of a nucleic acid molecule. In some embodiments, such amplification is performed using isothermal conditions; in other embodiments, such amplification can include thermocycling. In some embodiments, the amplification is a multiplex amplification that includes the simultaneous amplification of a plurality of target sequences in a single amplification reaction. At least some of the target sequences can be situated on the same nucleic acid molecule or on different target nucleic acid molecules included in the single amplification reaction. In some embodiments, "amplification" includes amplification of at least some portion of DNA- and RNA-based nucleic acids alone, or in combination. The amplification reaction can include single or double-stranded nucleic acid substrates and can further including any of the amplification processes known to one of ordinary skill in the art. In some embodiments, the amplification reaction includes polymerase chain reaction (PCR).

As used herein, "amplification conditions" and its derivatives, refers to conditions suitable for amplifying one or more nucleic acid sequences. Such amplification can be linear or exponential. In some embodiments, the amplification conditions can include isothermal conditions or alternatively can include thermocycling conditions, or a combination of isothermal and thermocycling conditions. In some embodiments, the conditions suitable for amplifying one or more nucleic acid sequences includes polymerase chain reaction (PCR) conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as Mg2+ or Mn2+(e.g., MgCl2, etc) and can also include various modifiers of ionic strength.

As used herein, "target sequence" or "target sequence of interest" and its derivatives, refers to any single or double-stranded nucleic acid sequence that can be amplified or synthesized according to the disclosure, including any nucleic acid sequence suspected or expected to be present in a sample. In some embodiments, the target sequence is present in double-stranded form and includes at least a portion of the particular nucleotide sequence to be amplified or synthesized, or its complement, prior to the addition of target-specific primers or appended adapters. Target sequences can include the nucleic acids to which primers useful in the amplification or synthesis reaction can hybridize prior to extension by a polymerase. In some embodiments, the term refers to a nucleic acid sequence whose sequence identity, ordering or location of nucleotides is determined by one or more of the methods of the disclosure.

As defined herein, "sample" and its derivatives, is used in its broadest sense and includes any specimen, culture and the like that is suspected of including a target. In some embodiments, the sample comprises cDNA, RNA, PNA, LNA, chimeric, hybrid, or multiplex-forms of nucleic acids. The sample can include any biological, clinical, surgical, agricultural, atmospheric or aquatic-based specimen containing one or more nucleic acids. The term also includes any isolated nucleic acid sample such as genomic DNA, fresh-frozen or formalin-fixed paraffin-embedded nucleic acid specimen.

As used herein, "contacting" and its derivatives, when used in reference to two or more components, refers to any process whereby the approach, proximity, mixture or commingling of the referenced components is promoted or achieved without necessarily requiring physical contact of such components, and includes mixing of solutions containing any one or more of the referenced components with each other. The referenced components may be contacted in any particular order or combination and the particular order of recitation of components is not limiting. For example, "contacting A with B and C" encompasses embodiments where A is first contacted with B then C, as well as embodiments where C is contacted with A then B, as well as embodiments where a mixture of A and C is contacted with B, and the like. Furthermore, such contacting does not necessarily require that the end result of the contacting process be a mixture including all of the referenced components, as long as at some point during the contacting process all of the referenced components are simultaneously present or simultaneously included in the same mixture or solution. Where one or more of the referenced components to be contacted includes a plurality (e.g, "contacting a target sequence with a plurality of target-specific primers and a polymerase"), then each member of the plurality can be viewed as an individual component of the contacting process, such that the contacting can include contacting of any one or more members of the plurality with any other member of the plurality and/or with any other referenced component (e.g., some but not all of the plurality of target specific primers can be contacted with a target sequence, then a polymerase, and then with other members of the plurality of target-specific primers) in any order or combination.

As used herein, the term "primer" and its derivatives refer to any polynucleotide that can hybridize to a target sequence of interest. In some embodiments, the primer can also serve to prime nucleic acid synthesis. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer may be comprised of any combination of nucleotides or analogs thereof, which may be optionally linked to form a linear polymer of any suitable length. In some embodiments, the primer is a single-stranded oligonucleotide or polynucleotide. (For purposes of this disclosure, the terms 'polynucleotide" and "oligonucleotide" are used interchangeably herein and do not necessarily indicate any difference in length between the two). In some embodiments, the primer is single-stranded but it can also be double-stranded. The primer optionally occurs naturally, as in a purified restriction digest, or can be produced synthetically. In some embodiments, the primer acts as a point of initiation for amplification or synthesis when exposed to amplification or synthesis conditions; such amplification or synthesis can occur in a template-dependent fashion and optionally results in formation of a primer extension product that is complementary to at least a portion of the target sequence. Exemplary amplification or synthesis conditions can include contacting the primer with a polynucleotide template (e.g., a template including a target sequence), nucleotides and an inducing agent such as a polymerase at a suitable temperature and pH to induce polymerization of nucleotides onto an end of the target-specific primer. If double-stranded, the primer can optionally be treated to separate its strands before being used to prepare primer extension products. In some embodiments, the primer is an oligodeoxyribonucleotide or an oligoribonucleotide. In some embodiments, the primer can include one or more nucleotide analogs. The exact length and/or composition, including sequence, of the target-specific primer can influence many properties, including melting temperature (Tm), GC content, formation of secondary structures, repeat nucleotide motifs, length of predicted primer extension products, extent of coverage across a nucleic acid molecule of interest, number of primers present in a single amplification or synthesis reaction, presence of nucleotide analogs or modified nucleotides within the primers, and the like. In some embodiments, a primer can be paired with a compatible primer within an amplification or synthesis reaction to form a primer pair consisting or a forward primer and a reverse primer. In some embodiments, the forward primer of the primer pair includes a sequence that is substantially complementary to at least a portion of a strand of a nucleic acid molecule, and the reverse primer of the primer of the primer pair includes a sequence that is substantially identical to at least of portion of the strand. In some embodiments, the forward primer and the reverse primer are capable of hybridizing to opposite strands of a nucleic acid duplex. Optionally, the forward primer primes synthesis of a first nucleic acid strand, and the reverse primer primes synthesis of a second nucleic acid strand, wherein the first and second strands are substantially complementary to each other, or can hybridize to form a double-stranded nucleic acid molecule. In some embodiments, one end of an amplification or synthesis product is defined by the forward primer and the other end of the amplification or synthesis product is defined by the reverse primer. In some embodiments, where the amplification or synthesis of lengthy primer extension products is required, such as amplifying an exon, coding region, or gene, several primer pairs can be created than span the desired length to enable sufficient amplification of the region. In some embodiments, a primer can include one or more cleavable groups. In some embodiments, primer lengths are in the range of about 10 to about 60 nucleotides, about 12 to about 50 nucleotides and about 15 to about 40 nucleotides in length. Typically, a primer is capable of hybridizing to a corresponding target sequence and undergoing primer extension when exposed to amplification conditions in the presence of dNTPs and a polymerase. In some embodiments, the primer includes one or more cleavable groups at one or more locations within the primer.

As used herein, "target-specific primer" and its derivatives, refers to a single stranded or double-stranded polynucleotide, typically an oligonucleotide, that includes at least one sequence that is at least 50% complementary, typically at least 75% complementary or at least 85% complementary, more typically at least 90% complementary, more typically at least 95% complementary, more typically at least 98% or at least 99% complementary, or identical, to at least a portion of a nucleic acid molecule that includes a target sequence. In such instances, the target-specific primer and target sequence are described as "corresponding" to each other. In some embodiments, the target-specific primer is capable of hybridizing to at least a portion of its corresponding target sequence (or to a complement of the target sequence); such hybridization can optionally be performed under standard hybridization conditions or under stringent hybridization conditions. In some embodiments, the target-specific primer is not capable of hybridizing to the target sequence, or to its complement, but is capable of hybridizing to a portion of a nucleic acid strand including the target sequence, or to its complement. In some embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the target sequence itself; in other embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the nucleic acid molecule other than the target sequence. In some embodiments, the target-specific primer is substantially non-complementary to other target sequences present in the sample; optionally, the target-specific primer is substantially non-complementary to other nucleic acid molecules present in the sample. In some embodiments, nucleic acid molecules present in the sample that do not include or correspond to a target sequence (or to a complement of the target sequence) are referred to as "non-specific" sequences or "non-specific nucleic acids". In some embodiments, the target-specific primer is designed to include a nucleotide sequence that is substantially complementary to at least a portion of its corresponding target sequence. In some embodiments, a target-specific primer is at least 95% complementary, or at least 99% complementary, or identical, across its entire length to at least a portion of a nucleic acid molecule that includes its corresponding target sequence. In some embodiments, a target-specific primer is at least 90%, at least 95% complementary, at least 98% complementary or at least 99% complementary, or identical, across its entire length to at least a portion of its corresponding target sequence. In some embodiments, a forward target-specific primer and a reverse target-specific primer define a target-specific primer pair that are used to amplify the target sequence via template-dependent primer extension. Typically, each primer of a target-specific primer pair includes at least one sequence that is substantially complementary to at least a portion of a nucleic acid molecule including a corresponding target sequence but that is less than 50% complementary to at least one other target sequence in the sample. In some embodiments, amplification is performed using multiple target-specific primer pairs in a single amplification reaction, wherein each primer pair includes a forward target-specific primer and a reverse target-specific primer, each including at least one sequence that substantially complementary or substantially identical to a corresponding target sequence in the sample, and each primer pair having a different corresponding target sequence. In some embodiments, the target-specific primer is substantially non-complementary at its 3' end or its 5' end to any other target-specific primer present in an amplification reaction. In some embodiments, the target-specific primer can include minimal cross hybridization to other target-specific primers in the amplification reaction. In some embodiments, target-specific primers include minimal cross-hybridization to non-specific sequences in the amplification reaction mixture. In some embodiments, the target-specific primers include minimal self-complementarity. In some embodiments, the target-specific primers can include one or more cleavable groups located at the 3' end. In some embodiments, the target-specific primers can include one or more cleavable groups located near or about a central nucleotide of the target-specific primer. In some embodiments, one of more targets-specific primers includes only non-cleavable nucleotides at the 5' end of the target-specific primer. In some embodiments, a target specific primer includes minimal nucleotide sequence overlap at the 3' end or the 5' end of the primer as compared to one or more different target-specific primers, optionally in the same amplification reaction. In some embodiments 1, 2, 3, 4, 5, 6, 7, 8, 9, 10 or more, target-specific primers in a single reaction mixture include one or more of the above embodiments. In some embodiments, substantially all of the plurality of target-specific primers in a single reaction mixture includes one or more of the above embodiments.

As used herein, "polymerase" and its derivatives, refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase is a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain. Optionally, the polymerase can possess 5' exonuclease activity or terminal transferase activity. In some embodiments, the polymerase is optionally reactivated, for example through the use of heat, chemicals or re-addition of new amounts of polymerase into a reaction mixture. In some embodiments, the polymerase can include a hot-start polymerase or an aptamer based polymerase that optionally is reactivated.

As used herein, the term "nucleotide" and its variants comprises any compound, including without limitation any naturally occurring nucleotide or analog thereof, which can bind selectively to, or is polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain is attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain is linked together with intervening O, NH, S, methylene, substituted methylene, ethylene, substituted ethylene, CNH2, C(O), C(CH2), CH2CH2, or C(OH)CH2R (where R can be a 4-pyridine or 1-imidazole). In one embodiment, the phosphorus atoms in the chain has side groups having O, BH3, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in U.S. Pat. No. 7,405,281. In some embodiments, the nucleotide comprises a label and referred to herein as a "labeled nucleotide"; the label of the labeled nucleotide is referred to herein as a "nucleotide label." In some embodiments, the label is in the form of a fluorescent dye attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group can include sulfur substitutions for the various oxygens, e.g. alpha-thio-nucleotide 5'-triphosphates. For a review of nucleic acid chemistry, see: Shabarova, Z. and Bogdanov, A. Advanced Organic Chemistry of Nucleic Acids, VCH, New York, 1994.

The term "extension" and its variants, as used herein, when used in reference to a given primer, comprises any in vivo or in vitro enzymatic activity characteristic of a given polymerase that relates to polymerization of one or more nucleotides onto an end of an existing nucleic acid molecule. Typically but not necessarily such primer extension occurs in a template-dependent fashion; during template-dependent extension, the order and selection of bases is driven by established base pairing rules, which can include Watson-Crick type base pairing rules or alternatively (and especially in the case of extension reactions involving nucleotide analogs) by some other type of base pairing paradigm. In one non-limiting example, extension occurs via polymerization of nucleotides on the 3'OH end of the nucleic acid molecule by the polymerase.

The term "portion" and its variants, as used herein, when used in reference to a given nucleic acid molecule, for example a primer or a template nucleic acid molecule, comprises any number of contiguous nucleotides within the length of the nucleic acid molecule, including the partial or entire length of the nucleic acid molecule.

The terms "identity" and "identical" and their variants, as used herein, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95%, 98% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 85% identity at the amino acid level or at the nucleotide level. Preferably, the identity exists over a region that is at least about 25, 50, or 100 residues in length, or across the entire length of at least one compared sequence. A typical algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent hybridization conditions.

The terms "complementary" and "complement" and their variants, as used herein, refer to any two or more nucleic acid sequences (e.g., portions or entireties of template nucleic acid molecules, target sequences and/or primers) that can undergo cumulative base pairing at two or more individual corresponding positions in antiparallel orientation, as in a hybridized duplex. Such base pairing can proceed according to any set of established rules, for example according to Watson-Crick base pairing rules or according to some other base pairing paradigm. Optionally there can be "complete" or "total" complementarity between a first and second nucleic acid sequence where each nucleotide in the first nucleic acid sequence can undergo a stabilizing base pairing interaction with a nucleotide in the corresponding antiparallel position on the second nucleic acid sequence. "Partial" complementarity describes nucleic acid sequences in which at least 20%, but less than 100%, of the residues of one nucleic acid sequence are complementary to residues in the other nucleic acid sequence. In some embodiments, at least 50%, but less than 100%, of the residues of one nucleic acid sequence are complementary to residues in the other nucleic acid sequence. In some embodiments, at least 70%, 80%, 90%, 95% or 98%, but less than 100%, of the residues of one nucleic acid sequence are complementary to residues in the other nucleic acid sequence. Sequences are said to be "substantially complementary" when at least 85% of the residues of one nucleic acid sequence are complementary to residues in the other nucleic acid sequence. In some embodiments, two complementary or substantially complementary sequences are capable of hybridizing to each other under standard or stringent hybridization conditions. "Non-complementary" describes nucleic acid sequences in which less than 20% of the residues of one nucleic acid sequence are complementary to residues in the other nucleic acid sequence. Sequences are said to be "substantially non-complementary" when less than 15% of the residues of one nucleic acid sequence are complementary to residues in the other nucleic acid sequence. In some embodiments, two non-complementary or substantially non-complementary sequences cannot hybridize to each other under standard or stringent hybridization conditions. A "mismatch" is present at any position in the sequences where two opposed nucleotides are not complementary. Complementary nucleotides include nucleotides that are efficiently incorporated by DNA polymerases opposite each other during DNA replication under physiological conditions. In a typical embodiment, complementary nucleotides can form base pairs with each other, such as the A-T/U and G-C base pairs formed through specific Watson-Crick type hydrogen bonding, or base pairs formed through some other type of base pairing paradigm, between the nucleobases of nucleotides and/or polynucleotides in positions antiparallel to each other. The complementarity of other artificial base pairs can be based on other types of hydrogen bonding and/or hydrophobicity of bases and/or shape complementarity between bases.

As used herein, "amplified target sequences" and its derivatives, refers to a nucleic acid sequence produced by the amplification of/amplifying the target sequences using target-specific primers and the methods provided herein. The amplified target sequences may be either of the same sense (the positive strand produced in the second round and subsequent even-numbered rounds of amplification) or antisense (i.e., the negative strand produced during the first and subsequent odd-numbered rounds of amplification) with respect to the target sequences. In some embodiments, the amplified target sequences is less than 50% complementary to any portion of another amplified target sequence in the reaction. In other embodiments, the amplified target sequences is greater than 50%, greater than 60%, greater than 70%, greater than 80%, or greater than 90% complementary to any portion of another amplified target sequence in the reaction.

As used herein, the terms "ligating", "ligation" and their derivatives refer to the act or process for covalently linking two or more molecules together, for example, covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, for example embodiments wherein the nucleic acid molecules to be ligated include conventional nucleotide residues, the ligation can include forming a covalent bond between a 5' phosphate group of one nucleic acid and a 3' hydroxyl group of a second nucleic acid thereby forming a ligated nucleic acid molecule. In some embodiments, any means for joining nicks or bonding a 5' phosphate to a 3' hydroxyl between adjacent nucleotides can be employed. In an exemplary embodiment, an enzyme such as a ligase is used. For the purposes of this disclosure, an amplified target sequence can be ligated to an adapter to generate an adapter-ligated amplified target sequence.

As used herein, "ligase" and its derivatives, refers to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. In some embodiments, the ligase is an isothermal ligase. In some embodiments, the ligase is a thermostable ligase. Suitable ligases may include, but not limited to, T4 DNA ligase, T4 RNA ligase, and E. coli DNA ligase.

As used herein, "ligation conditions" and its derivatives, refers to conditions suitable for ligating two molecules to each other. In some embodiments, the ligation conditions are suitable for sealing nicks or gaps between nucleic acids. As defined herein, a "nick" or "gap" refers to a nucleic acid molecule that lacks a directly bound 5' phosphate of a mononucleotide pentose ring to a 3' hydroxyl of a neighboring mononucleotide pentose ring within internal nucleotides of a nucleic acid sequence. As used herein, the term nick or gap is consistent with the use of the term in the art. Typically, a nick or gap is ligated in the presence of an enzyme, such as ligase at an appropriate temperature and pH. In some embodiments, T4 DNA ligase can join a nick between nucleic acids at a temperature of about 70-72° C.

As used herein, "blunt-end ligation" and its derivatives, refers to ligation of two blunt-end double-stranded nucleic acid molecules to each other. A "blunt end" refers to an end of a double-stranded nucleic acid molecule wherein substantially all of the nucleotides in the end of one strand of the nucleic acid molecule are base paired with opposing nucleotides in the other strand of the same nucleic acid molecule. A nucleic acid molecule is not blunt ended if it has an end that includes a single-stranded portion greater than two nucleotides in length, referred to herein as an "overhang". In some embodiments, the end of nucleic acid molecule does not include any single stranded portion, such that every nucleotide in one strand of the end is based paired with opposing nucleotides in the other strand of the same nucleic acid molecule. In some embodiments, the ends of the two blunt ended nucleic acid molecules that become ligated to each other do not include any overlapping, shared or complementary sequence. Typically, blunted-end ligation excludes the use of additional oligonucleotide adapters to assist in the ligation of the double-stranded amplified target sequence to the double-stranded adapter, such as patch oligonucleotides as described in US Pat. Publication No. 2010/0129874. In some embodiments, blunt-ended ligation includes a nick translation reaction to seal a nick created during the ligation process.

As used herein, the terms "adapter" or "adapter and its complements" and their derivatives, refers to any linear oligonucleotide which is ligated to a nucleic acid molecule of the disclosure. Optionally, the adapter includes a nucleic acid sequence that is not substantially complementary to the 3' end or the 5' end of at least one target sequences within the sample. In some embodiments, the adapter is substantially non-complementary to the 3' end or the 5' end of any target sequence present in the sample. In some embodiments, the adapter includes any single stranded or double-stranded linear oligonucleotide that is not substantially complementary to an amplified target sequence. In some embodiments, the adapter is substantially non-complementary to at least one, some or all of the nucleic acid molecules of the sample. In some embodiments, suitable adapter lengths are in the range of about 10-100 nucleotides, about 12-60 nucleotides and about 15-50 nucleotides in length. An adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a universal primer. The structure and properties of universal amplification primers are well known to those skilled in the art and can be implemented for utilization in conjunction with provided methods and compositions to adapt to specific analysis platforms (e.g., as described herein universal P1 and A primers have been described in the art and utilized for sequencing on Ion Torrent sequencing platforms). Similarly, additional and other universal adaptor/primer sequences described and known in the art (e.g., Illumina universal adaptor/primer sequences, PacBio universal adaptor/primer sequences, etc.) can be used in conjunction with the methods and compositions provided herein. In some embodiments, the adapter can include a barcode or tag to assist with downstream cataloguing, identification or sequencing. In some embodiments, a single-stranded adapter can act as a substrate for amplification when ligated to an amplified target sequence, particularly in the presence of a polymerase and dNTPs under suitable temperature and pH.

In some embodiments, an adapter is ligated to a polynucleotide through a blunt-end ligation. In other embodiments, an adapter is ligated to a polynucleotide via nucleotide overhangs on the ends of the adapter and the polynucleotide. For overhang ligation, an adapter may have a nucleotide overhang added to the 3' and/or 5' ends of the respective strands if the polynucleotides to which the adapters are to be ligated (eg, amplicons) have a complementary overhang added to the 3' and/or 5' ends of the respective strands. For example, adenine nucleotides can be added to the 3' terminus of an end-repaired PCR product. Adapters having with an overhang formed by thymine nucleotides can then dock with the A-overhang of the amplicon and be ligated to the amplicon by a DNA ligase, such as T4 DNA ligase.

As used herein, "reamplifying" or "reamplification" and their derivatives refer to any process whereby at least a portion of an amplified nucleic acid molecule is further amplified via any suitable amplification process (referred to in some embodiments as a "secondary" amplification or "reamplification", thereby producing a reamplified nucleic acid molecule. The secondary amplification need not be identical to the original amplification process whereby the amplified nucleic acid molecule was produced; nor need the reamplified nucleic acid molecule be completely identical or completely complementary to the amplified nucleic acid molecule; all that is required is that the reamplified nucleic acid molecule include at least a portion of the amplified nucleic acid molecule or its complement. For example, the reamplification can involve the use of different amplification conditions and/or different primers, including different target-specific primers than the primary amplification.

As defined herein, a "cleavable group" refers to any moiety that once incorporated into a nucleic acid can be cleaved under appropriate conditions. For example, a cleavable group can be incorporated into a target-specific primer, an amplified sequence, an adapter or a nucleic acid molecule of the sample. In an exemplary embodiment, a target-specific primer can include a cleavable group that becomes incorporated into the amplified product and is subsequently cleaved after amplification, thereby removing a portion, or all, of the target-specific primer from the amplified product. The cleavable group can be cleaved or otherwise removed from a target-specific primer, an amplified sequence, an adapter or a nucleic acid molecule of the sample by any acceptable means. For example, a cleavable group can be removed from a target-specific primer, an amplified sequence, an adapter or a nucleic acid molecule of the sample by enzymatic, thermal, photo-oxidative or chemical treatment. In one aspect, a cleavable group can include a nucleobase that is not naturally occurring. For example, an oligodeoxyribonucleotide can include one or more RNA nucleobases, such as uracil that can be removed by a uracil glycosylase. In some embodiments, a cleavable group can include one or more modified nucleobases (such as 7-methylguanine, 8-oxo-guanine, xanthine, hypoxanthine, 5,6-dihydrouracil or 5-methylcytosine) or one or more modified nucleosides (i.e., 7-methylguanosine, 8-oxo-deoxyguanosine, xanthosine, inosine, dihydrouridine or 5-methylcytidine). The modified nucleobases or nucleotides can be removed from the nucleic acid by enzymatic, chemical or thermal means. In one embodiment, a cleavable group can include a moiety that can be removed from a primer after amplification (or synthesis) upon exposure to ultraviolet light (i.e., bromodeoxyuridine). In another embodiment, a cleavable group can include methylated cytosine. Typically, methylated cytosine can be cleaved from a primer for example, after induction of amplification (or synthesis), upon sodium bisulfite treatment. In some embodiments, a cleavable moiety can include a restriction site. For example, a primer or target sequence can include a nucleic acid sequence that is specific to one or more restriction enzymes, and following amplification (or synthesis), the primer or target sequence can be treated with the one or more restriction enzymes such that the cleavable group is removed. Typically, one or more cleavable groups can be included at one or more locations with a target-specific primer, an amplified sequence, an adapter or a nucleic acid molecule of the sample.

As used herein, "cleavage step" and its derivatives, refers to any process by which a cleavable group is cleaved or otherwise removed from a target-specific primer, an amplified sequence, an adapter or a nucleic acid molecule of the sample. In some embodiments, the cleavage step involves a chemical, thermal, photo-oxidative or digestive process.

As used herein, the term "hybridization" is consistent with its use in the art, and refers to the process whereby two nucleic acid molecules undergo base pairing interactions. Two nucleic acid molecule molecules are said to be hybridized when any portion of one nucleic acid molecule is base paired with any portion of the other nucleic acid molecule; it is not necessarily required that the two nucleic acid molecules be hybridized across their entire respective lengths and in some embodiments, at least one of the nucleic acid molecules can include portions that are not hybridized to the other nucleic acid molecule. The phrase "hybridizing under stringent conditions" and its variants refers to conditions under which hybridization of a target-specific primer to a target sequence occurs in the presence of high hybridization temperature and low ionic strength. In one exemplary embodiment, stringent hybridization conditions include an aqueous environment containing about 30 mM magnesium sulfate, about 300 mM Tris-sulfate at pH 8.9, and about 90 mM ammonium sulfate at about 60-68° C., or equivalents thereof. As used herein, the phrase "standard hybridization conditions" and its variants refers to conditions under which hybridization of a primer to an oligonucleotide (i.e., a target sequence), occurs in the presence of low hybridization temperature and high ionic strength. In one exemplary embodiment, standard hybridization conditions include an aqueous environment containing about 100 mM magnesium sulfate, about 500 mM Tris-sulfate at pH 8.9, and about 200 mM ammonium sulfate at about 50-55° C., or equivalents thereof.

As used herein, "GC content" and its derivatives, refers to the cytosine and guanine content of a nucleic acid molecule. The GC content of a target-specific primer (or adapter) of the disclosure is 85% or lower. More typically, the GC content of a target-specific primer or adapter of the disclosure is between 15-85%.

As used herein, the term "end" and its variants, when used in reference to a nucleic acid molecule, for example a target sequence or amplified target sequence, can include the terminal 30 nucleotides, the terminal 20 and even more typically the terminal 15 nucleotides of the nucleic acid molecule. A linear nucleic acid molecule comprised of linked series of contiguous nucleotides typically includes at least two ends. In some embodiments, one end of the nucleic acid molecule can include a 3' hydroxyl group or its equivalent, and is referred to as the "3' end" and its derivatives. Optionally, the 3' end includes a 3' hydroxyl group that is not linked to a 5' phosphate group of a mononucleotide pentose ring. Typically, the 3' end includes one or more 5' linked nucleotides located adjacent to the nucleotide including the unlinked 3' hydroxyl group, typically the 30 nucleotides located adjacent to the 3' hydroxyl, typically the terminal 20 and even more typically the terminal 15 nucleotides. One or more linked nucleotides can be represented as a percentage of the nucleotides present in the oligonucleotide or can be provided as a number of linked nucleotides adjacent to the unlinked 3' hydroxyl. For example, the 3' end can include less than 50% of the nucleotide length of the oligonucleotide. In some embodiments, the 3' end does not include any unlinked 3' hydroxyl group but can include any moiety capable of serving as a site for attachment of nucleotides via primer extension and/or nucleotide polymerization. In some embodiments, the term "3' end" for example when referring to a target-specific primer, can include the terminal 10 nucleotides, the terminal 5 nucleotides, the terminal 4, 3, 2 or fewer nucleotides at the 3' end. In some embodiments, the term "3' end" when referring to a target-specific primer can include nucleotides located at nucleotide positions 10 or fewer from the 3' terminus.

As used herein, "5' end", and its derivatives, refers to an end of a nucleic acid molecule, for example a target sequence or amplified target sequence, which includes a free 5' phosphate group or its equivalent. In some embodiments, the 5' end includes a 5' phosphate group that is not linked to a 3' hydroxyl of a neighboring mononucleotide pentose ring. Typically, the 5' end includes to one or more linked nucleotides located adjacent to the 5' phosphate, typically the 30 nucleotides located adjacent to the nucleotide including the 5' phosphate group, typically the terminal 20 and even more typically the terminal 15 nucleotides. One or more linked nucleotides can be represented as a percentage of the nucleotides present in the oligonucleotide or can be provided as a number of linked nucleotides adjacent to the 5' phosphate. For example, the 5' end can be less than 50% of the nucleotide length of an oligonucleotide. In another exemplary embodiment, the 5' end can include about 15 nucleotides adjacent to the nucleotide including the terminal 5' phosphate. In some embodiments, the 5' end does not include any unlinked 5' phosphate group but can include any moiety capable of serving as a site of attachment to a 3' hydroxyl group, or to the 3' end of another nucleic acid molecule. In some embodiments, the term "5' end" for example when referring to a target-specific primer, can include the terminal 10 nucleotides, the terminal 5 nucleotides, the terminal 4, 3, 2 or fewer nucleotides at the 5' end. In some embodiments, the term "5' end" when referring to a target-specific primer can include nucleotides located at positions 10 or fewer from the 5' terminus. In some embodiments, the 5' end of a target-specific primer can include only non-cleavable nucleotides, for example nucleotides that do not contain one or more cleavable groups as disclosed herein, or a cleavable nucleotide as would be readily determined by one of ordinary skill in the art.

As used herein, "DNA barcode" and its derivatives, refers to a unique short (e.g., 6-14 nucleotide) nucleic acid sequence within an adapter that can act as a 'key' to distinguish or separate a plurality of amplified target sequences in a sample. For the purposes of this disclosure, a DNA barcode can be incorporated into the nucleotide sequence of an adapter.

As used herein, the phrases "two rounds of target-specific hybridization" or "two rounds of target-specific selection" and their derivatives refers to any process whereby the same target sequence is subjected to two consecutive rounds of hybridization-based target-specific selection, wherein a target sequence is hybridized to a target-specific sequence. Each round of hybridization based target-specific selection can include multiple target-specific hybridizations to at least some portion of a target-specific sequence. In one exemplary embodiment, a round of target-specific selection includes a first target-specific hybridization involving a first region of the target sequence and a second target-specific hybridization involving a second region of the target sequence. The first and second regions can be the same or different. In some embodiments, each round of hybridization-based target-specific selection can include use of two target specific oligonucleotides (e.g., a forward target-specific primer and a reverse target-specific primer), such that each round of selection includes two target-specific hybridizations.

As used herein, "comparable maximal minimum melting temperatures" and its derivatives, refers to the melting temperature (Tm) of each nucleic acid fragment for a single adapter or target-specific primer after cleavage of the cleavable groups. The hybridization temperature of each nucleic acid fragment generated by a single adapter or target-specific primer is compared to determine the maximal minimum temperature required preventing hybridization of any nucleic acid fragment from the target-specific primer or adapter to the target sequence. Once the maximal hybridization temperature is known, it is possible to manipulate the adapter or target-specific primer, for example by moving the location of the cleavable group along the length of the primer, to achieve a comparable maximal minimum melting temperature with respect to each nucleic acid fragment.

As used herein, "addition only" and its derivatives, refers to a series of steps in which reagents and components are added to a first or single reaction mixture. Typically, the series of steps excludes the removal of the reaction mixture from a first vessel to a second vessel in order to complete the series of steps. An addition only process excludes the manipulation of the reaction mixture outside the vessel containing the reaction mixture. Typically, an addition-only process is amenable to automation and high-throughput.

As used herein, "synthesizing" and its derivatives, refers to a reaction involving nucleotide polymerization by a polymerase, optionally in a template-dependent fashion. Polymerases synthesize an oligonucleotide via transfer of a nucleoside monophosphate from a nucleoside triphosphate (NTP), deoxynucleoside triphosphate (dNTP) or dideoxynucleoside triphosphate (ddNTP) to the 3' hydroxyl of an extending oligonucleotide chain. For the purposes of this disclosure, synthesizing includes to the serial extension of a hybridized adapter or a target-specific primer via transfer of a nucleoside monophosphate from a deoxynucleoside triphosphate.

As used herein, "polymerizing conditions" and its derivatives, refers to conditions suitable for nucleotide polymerization. In typical embodiments, such nucleotide polymerization is catalyzed by a polymerase. In some embodiments, polymerizing conditions include conditions for primer extension, optionally in a template-dependent manner, resulting in the generation of a synthesized nucleic acid sequence. In some embodiments, the polymerizing conditions include polymerase chain reaction (PCR). Typically, the polymerizing conditions include use of a reaction mixture that is sufficient to synthesize nucleic acids and includes a polymerase and nucleotides. The polymerizing conditions can include conditions for annealing of a target-specific primer to a target sequence and extension of the primer in a template dependent manner in the presence of a polymerase. In some embodiments, polymerizing conditions are practiced using thermocycling. Additionally, polymerizing conditions can include a plurality of cycles where the steps of annealing, extending, and separating the two nucleic strands are repeated. Typically, the polymerizing conditions include a cation such as MgCl2. Polymerization of one or more nucleotides to form a nucleic acid strand includes that the nucleotides be linked to each other via phosphodiester bonds, however, alternative linkages may be possible in the context of particular nucleotide analogs.

As used herein, the term "nucleic acid" refers to natural nucleic acids, artificial nucleic acids, analogs thereof, or combinations thereof, including polynucleotides and oligonucleotides. As used herein, the terms "polynucleotide" and "oligonucleotide" are used interchangeably and mean single-stranded and double-stranded polymers of nucleotides including, but not limited to, 2'-deoxyribonucleotides (nucleic acid) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as H+, NH4+, trialkylammonium, Mg2+, Na+ and the like. An oligonucleotide can be composed entirely of deoxyribonucleotides, entirely of ribonucleotides, or chimeric mixtures thereof. Oligonucleotides can be comprised of nucleobase and sugar analogs. Polynucleotides typically range in size from a few monomeric units, e.g. 5-40, when they are more commonly frequently referred to in the art as oligonucleotides, to several thousands of monomeric nucleotide units, when they are more commonly referred to in the art as polynucleotides; for purposes of this disclosure, however, both oligonucleotides and polynucleotides may be of any suitable length. Unless denoted otherwise, whenever a oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "U" denotes deoxyuridine. Oligonucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage.

As defined herein, the term "nick translation" and its variants comprise the translocation of one or more nicks or gaps within a nucleic acid strand to a new position along the nucleic acid strand. In some embodiments, a nick is formed when a double stranded adapter is ligated to a double stranded amplified target sequence. In one example, the primer can include at its 5' end, a phosphate group that can ligate to the double stranded amplified target sequence, leaving a nick between the adapter and the amplified target sequence in the complementary strand. In some embodiments, nick translation results in the movement of the nick to the 3' end of the nucleic acid strand. In some embodiments, moving the nick can include performing a nick translation reaction on the adapter-ligated amplified target sequence. In some embodiments, the nick translation reaction is a coupled 5' to 3' DNA polymerization/degradation reaction, or coupled to a 5' to 3' DNA polymerization/strand displacement reaction. In some embodiments, moving the nick can include performing a DNA strand extension reaction at the nick site. In some embodiments, moving the nick can include performing a single strand exonuclease reaction on the nick to form a single stranded portion of the adapter-ligated amplified target sequence and performing a DNA strand extension reaction on the single stranded portion of the adapter-ligated amplified target sequence to a new position. In some embodiments, a nick is formed in the nucleic acid strand opposite the site of ligation.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a polynucleotide of interest in a mixture of expressed RNA or cDNA without cloning or purification. This process for amplifying the polynucleotide of interest consists of introducing a large excess of two oligonucleotide primers to the DNA mixture containing the desired polynucleotide of interest, followed by a precise sequence of thermal cycling in the presence of a DNA polymerase. The two primers are complementary to their respective strands of the double stranded polynucleotide of interest. To effect amplification, the mixture is denatured and the primers then annealed to their complementary sequences within the polynucleotide of interest molecule. Following annealing, the primers are extended with a polymerase to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". As defined herein, target nucleic acid molecules within a sample including a plurality of target nucleic acid molecules are amplified via PCR. In a modification to the method discussed above, the target nucleic acid molecules are PCR amplified using a plurality of different primer pairs, in some cases, one or more primer pairs per target nucleic acid molecule of interest, thereby forming a multiplex PCR reaction. In some embodiments provided herein, multiplex PCR amplifications are performed using a plurality of different primer pairs, in typical cases, one primer pair per target nucleic acid molecule. Using multiplex PCR, it is possible to simultaneously amplify multiple nucleic acid molecules of interest from a sample to form amplified target sequences. It is also possible to detect the amplified target sequences by several different methodologies (e.g., quantitation with a bioanalyzer or qPCR, hybridization with a labeled probe; incorporation of biotinylated primers followed by avidin-enzyme conjugate detection; incorporation of 32P-labeled deoxynucleotide triphosphates, such as dCTP or dATP, into the amplified target sequence). Any oligonucleotide sequence can be amplified with the appropriate set of primers, thereby allowing for the amplification of target nucleic acid molecules from RNA, cDNA, formalin-fixed paraffin-embedded DNA, fine-needle biopsies and various other sources. In particular, the amplified target sequences created by the multiplex PCR process as disclosed herein, are themselves efficient substrates for subsequent PCR amplification or various downstream assays or manipulations.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers to the number of different target-specific sequences that are amplified during that single multiplex amplification. In some embodiments, the plexy is about 12-plex, 24-plex, 48-plex, 74-plex, 96-plex, 120-plex, 144-plex, 168-plex, 192-plex, 216-plex, 240-plex, 264-plex, 288-plex, 312-plex, 336-plex, 360-plex, 384-plex, or 398-plex. In some embodiments, highly multiplexed amplification reactions include reactions with a plexy of greater than 12-plex.

In some embodiments, the amplified target sequences are formed via PCR. Extension of target-specific primers can be accomplished using one or more DNA polymerases. In one embodiment, the polymerase is any Family A DNA polymerase (also known as pol I family) or any Family B DNA polymerase. In some embodiments, the DNA polymerase is a recombinant form capable of extending target-specific primers with superior accuracy and yield as compared to a non-recombinant DNA polymerase. For example, the polymerase can include a high-fidelity polymerase or thermostable polymerase. In some embodiments, conditions for extension of target-specific primers can include 'Hot Start' conditions, for example Hot Start polymerases, such as Amplitaq Gold™ DNA polymerase (Applied Biosciences), Platinum® Taq DNA Polymerase High Fidelity (Invitrogen) or KOD Hot Start DNA polymerase (EMD Biosciences). A 'Hot Start' polymerase includes a thermostable polymerase and one or more antibodies that inhibit DNA polymerase and 3'-5' exonuclease activities at ambient temperature. In some instances, 'Hot Start' conditions can include an aptamer.

In some embodiments, the polymerase is an enzyme such as Taq polymerase (from *Thermus aquaticus*), Tfi polymerase (from *Thermus filiformis*), Bst polymerase (from *Bacillus stearothermophilus*), Pfu polymerase (from *Pyrococcus furiosus*), Tth polymerase (from *Thermus thermophilus*), Pow polymerase (from *Pyrococcus woesei*), Tli polymerase (from *Thermococcus litoralis*), Ultima polymerase (from *Thermotoga maritima*), KOD polymerase (from *Thermococcus kodakaraensis*), Pol I and II polymerases (from *Pyrococcus abyssi*) and Pab (from *Pyrococcus abyssi*). In some embodiments, the DNA polymerase can include at least one polymerase such as Amplitaq Gold™ DNA polymerase (Applied Biosciences), Stoffel fragment of Amplitag™ DNA Polymerase (Roche), KOD polymerase (EMD Biosciences), KOD Hot Start polymerase (EMD Biosciences), Deep Vent™ DNA polymerase (New England Biolabs), Phusion polymerase (New England Biolabs), Klentaq1 polymerase (DNA Polymerase Technology, Inc), Klentaq Long Accuracy polymerase (DNA Polymerase Technology, Inc), Omni KlenTaq™ DNA polymerase (DNA Polymerase Technology, Inc), Omni KlenTaq™ LA DNA polymerase (DNA Polymerase Technology, Inc), Platinum™ Taq DNA Polymerase (Invitrogen), Hemo Klentaq™ (New England Biolabs), Platinum™ Taq DNA Polymerase High Fidelity (Invitrogen), Platinum™ Pfx (Invitrogen), Accuprime™ Pfx (Invitrogen), or Accuprime™ Taq DNA Polymerase High Fidelity (Invitrogen).

In some embodiments, the DNA polymerase is a thermostable DNA polymerase. In some embodiments, the mixture of dNTPs is applied concurrently, or sequentially, in a random or defined order. In some embodiments, the amount of DNA polymerase present in the multiplex reaction is significantly higher than the amount of DNA polymerase used in a corresponding single plex PCR reaction. As defined herein, the term "significantly higher" refers to an at least 3-fold greater concentration of DNA polymerase present in the multiplex PCR reaction as compared to a corresponding single plex PCR reaction.

In some embodiments, the amplification reaction does not include a circularization of amplification product, for example as disclosed by rolling circle amplification.

The practice of the present subject matter may employ, unless otherwise indicated, conventional techniques and descriptions of organic chemistry, molecular biology (including recombinant techniques), cell biology, and biochemistry, which are within the skill of the art. Such conventional techniques include, but are not limited to, preparation of synthetic polynucleotides, polymerization techniques, chemical and physical analysis of polymer particles, preparation of nucleic acid libraries, nucleic acid sequencing and analysis, and the like. Specific illustrations of suitable techniques can be used by reference to the examples provided herein. Other equivalent conventional procedures can also be used. Such conventional techniques and descriptions can be found in standard laboratory manuals such as Genome Analysis: A Laboratory Manual Series (Vols. I-IV), PCR Primer: A Laboratory Manual, and Molecular Cloning: A Laboratory Manual (all from Cold Spring Harbor Laboratory Press), Hermanson, Bioconjugate Techniques, Second Edition (Academic Press, 2008); Merkus, Particle Size Measurements (Springer, 2009); Rubinstein and Colby, Polymer Physics (Oxford University Press, 2003); and the like.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and nonvolatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

Various additional exemplary embodiments may be derived by repeating, adding, or substituting any generically or specifically described features and/or components and/or substances and/or steps and/or operating conditions set forth in one or more of the above-described exemplary embodiments. Further, it should be understood that an order of steps or order for performing certain actions is immaterial so long as the objective of the steps or action remains achievable, unless specifically stated otherwise. Furthermore, two or more steps or actions can be conducted simultaneously so long as the objective of the steps or action remains achievable, unless specifically stated otherwise. Moreover, any one or more feature, component, aspect, step, or other characteristic mentioned in one of the above-discussed exemplary embodiments may be considered to be a potential optional feature, component, aspect, step, or other characteristic of any other of the above-discussed exemplary embodiments so long as the objective of such any other of the above-discussed exemplary embodiments remains achievable, unless specifically stated otherwise.

In certain embodiments, compositions of the invention comprise target immune receptor primer sets wherein the primers are directed to sequences of the same target immune receptor gene. Immune receptors are selected from T cell receptors and antibody receptors. In some embodiments a T cell receptor is a T cell receptor selected from the group consisting of TCR alpha, TCR beta, TCR gamma, and TCR delta. In some embodiments the immune receptor is an antibody receptor selected from the group consisting of heavy chain alpha, heavy chain delta, heavy chain epsilon, heavy chain gamma, heavy chain mu, light chain kappa, and light chain lambda.

In some embodiments, compositions of the invention comprise target immune receptor primer sets selected to have various parameters or criteria outlined herein. In some embodiments, compositions of the invention comprise a plurality of target-specific primers (e.g., V gene FR1-, FR2- and FR3-directed primers and the J gene directed primers) of about 15 nucleotides to about 40 nucleotides in length and having at least two or more following criteria: a cleavable group located at a 3' end of substantially all of the plurality of primers, a cleavable group located near or about a central nucleotide of substantially all of the plurality of primers, substantially all of the plurality of primers at a 5' end including only non-cleavable nucleotides, minimal cross-hybridization to substantially all of the primers in the plurality of primers, minimal cross-hybridization to non-specific sequences present in a sample, minimal self-complementarity, and minimal nucleotide sequence overlap at a 3' end or a 5' end of substantially all of the primers in the plurality of primers. In some embodiments, the composition can include primers with any 3, 4, 5, 6 or 7 of the above criteria.

In some embodiments, composition comprise a plurality of target-specific primers of about 15 nucleotides to about 40 nucleotides in length having two or more of the following criteria: a cleavable group located near or about a central nucleotide of substantially all of the plurality of primers, substantially all of the plurality of primers at a 5' end including only non-cleavable nucleotides, substantially all of the plurality of primers having less than 20% of the nucleotides across the primer's entire length containing a cleavable group, at least one primer having a complementary nucleic acid sequence across its entire length to a target sequence present in a sample, minimal cross-hybridization to substantially all of the primers in the plurality of primers, minimal cross-hybridization to non-specific sequences present in a sample, and minimal nucleotide sequence overlap at a 3' end or a 5' end of substantially all of the primers in the plurality of primers. In some embodiments, the composition can include primers with any 3, 4, 5, 6 or 7 of the above criteria.

In some embodiments, target-specific primers (e.g., the V gene FR1-, FR2- and FR3-directed primers and the J gene directed primers) used in the compositions of the invention are selected or designed to satisfy any one or more of the following criteria: (1) includes two or more modified nucleotides within the primer sequence, at least one of which is included near or at the termini of the primer and at least one of which is included at, or about the center nucleotide position of the primer sequence; (2) length of about 15 to about 40 bases in length; (3) Tm of from above 60° C. to about 70° C.; (4) low cross-reactivity with non-target sequences present in the sample; (5) at least the first four nucleotides (going from 3' to 5' direction) are non-complementary to any sequence within any other primer present in the composition; and (6) non-complementary to any consecutive stretch of at least 5 nucleotides within any other sequence targeted for amplification with the primers. In some embodiments, the target-specific primers used in the compositions are selected or designed to satisfy any 2, 3, 4, 5, or 6 of the above criteria. In some embodiments, the two or more modified nucleotides have cleavable groups. In some embodiments, each of the plurality of target-specific primers comprises two or more modified nucleotides selected from a cleavable group of methylguanine, 8-oxo- guanine, xanthine, hypoxanthine, 5,6-dihydrouracil, uracil, 5-methylcytosine, thymine-dimer, 7-methylguanosine, 8-oxo-deoxyguanosine, xanthosine, inosine, dihydrouridine, bromodeoxyuridine, uridine or 5-methylcytidine.

In some embodiments compositions are provided for analysis of an immune repertoire in a sample, comprising at least one set of i) a plurality of V gene primers directed to a majority of different V gene of at least one immune receptor coding sequence comprising at least a portion of framework region 3 (FR3) within the V gene; and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein each set of i) and ii) primers directed to the same target immune receptor is configured to amplify the target immune receptor repertoire. In certain embodiments a single set of primers comprising i) and ii) is encompassed within a composition. In particular embodiments such set comprises primers directed to an immune receptor comprising a T cell receptor. In more particular embodiments such set comprises primers directed to TCR beta. In other embodiments such set comprises primers directed to TCR alpha. In still other embodiments at least two sets of primers are encompassed in a composition wherein the sets are directed to TCR alpha and TCR beta.

In particular embodiments, compositions provided include target immune receptor primer sets comprising V gene primers wherein the one or more of a plurality of V gene primers are directed to sequences over an FR3 region about 50 nucleotides in length. In other particular embodiments the one or more of a plurality of V gene primers are directed to sequences over an FR3 region about 40 to about 60 nucleotides in length. In certain embodiments a target immune receptor primer set comprises V gene primers comprising about 50 to about 70 different FR-3 directed primers. In some embodiments a target immune receptor primer set comprises V gene primers comprising about 55 to about 65 different FR-3 directed primers. In some embodiments, a target immune receptor primer set comprises V gene primers comprising about 58, 59, 60, 61, or 62 different FR-3 directed primers. In some embodiments the target immune receptor primer set comprises a plurality of J gene primers. In some embodiments a target immune receptor primer set comprises at least 10 J gene primers wherein each is directed to at least a portion of a J gene within target polynucleotides. In some embodiments a target immune receptor primer set comprises at least 16 J gene primers wherein each is directed to at least a portion of a J gene within target polynucleotides. In some embodiments a target immune receptor primer set comprises about 10 to about 20 J gene primers wherein each is directed to at least a portion of a J gene within target polynucleotides. In some embodiments a target immune receptor primer set comprises about 12 to about 18 J gene primers wherein each is directed to at least a portion of a J gene within target polynucleotides. In some embodiments a target immune receptor primer set comprises about 12, 13, 14, 15, 16, 17 or 18 different J gene primers. In particular embodiments a target immune receptor primer set comprises about 16 J gene primers wherein each is directed to at least a portion of a J gene within target polynucleotides. In particular embodiments a target immune receptor primer set comprises about 14 J gene primers wherein each is directed to at least a portion of a J gene within target polynucleotides.

In particular embodiments, compositions of the invention comprise at least one set of primers comprising V gene primers i) and J gene primers ii) selected from Tables 3 and 5, respectively. In certain embodiments compositions of the invention comprise at least one set of primers i) and ii) comprising primers selected from SEQ ID NOs: 185-248 and 313-397 or selected from SEQ ID NOs: 185-248 and 398-482. In other certain embodiments compositions of the invention comprise at least one set of primers i) and ii) comprising primers selected from SEQ ID NOs: 185-248 and 313-329 or selected from SEQ ID NOs: 185-248 and 329-342. In other embodiments compositions of the invention comprise at least one set of primers i) and ii) comprising primers selected from SEQ ID NOs: 185-248 and 398-414 or selected from SEQ ID NOs: 185-248 and 414-427. In certain other embodiments compositions of the invention comprise at least one set of primers i) and ii) comprising primers SEQ ID NOs: 185-243 and 313-328. In still other embodiments compositions of the invention comprise at least one set of primers of i) and ii) comprising primers SEQ ID NOs: 185-243 and 398-413. In certain embodiments compositions of the invention comprise at least one set of primers i) and ii) comprising primers selected from SEQ ID NOs: 249-312 and 313-397 or selected from SEQ ID NOs: 249-312 and 398-482. In other embodiments compositions of the invention comprise at least one set of primers i) and ii) comprising primers selected from SEQ ID NOs: 249-312 and 313-329 or selected from SEQ ID NOs: 249-312 and 329-342. In other embodiments compositions of the invention comprise at least one set of primers i) and ii) comprising primers selected from SEQ ID NOs: 249-312 and 398-414 or selected from SEQ ID NOs: 249-312 and 414-427. In certain other embodiments compositions of the invention comprise at least one set of primers i) and ii) comprising primers SEQ ID NOs: 249-307 and 398-413. In still other embodiments compositions of the invention comprise at least one set of primers of i) and ii) comprising primers SEQ ID NOs: 249-307 and 313-328.

In some embodiments compositions of the invention comprise at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 398-482. In other embodiments compositions of the invention comprise at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 313-397. In some embodiments compositions of the invention comprise at least one set of primers i) and ii) comprising at least 50 primers selected from SEQ ID NOs: 185-248 and at least 10 primers, at least 12 primers, at least 14 primers, at least 16 primers, at least 18 primers, or at least 20 primers selected from SEQ ID NOs: 313-397. In other embodiments compositions of the invention comprise at least one set of primers i) and ii) comprising at least 50 primers selected from SEQ ID NOs: 185-248 and at least 10 primers, at least 12 primers, at least 14 primers, at least 16 primers, at least 18 primers, or at least 20 primers selected from SEQ ID NOs: 398-482.

In some embodiments compositions of the invention comprise at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 398-427. In other embodiments compositions of the invention comprise at least one set of primers i) and ii) comprising at least 50 primers selected from SEQ ID NOs: 249-312 and at least 10 primers, at least 12 primers, at least 14 primers, at least 16 primers, at least 18 primers, or at least 20 primers selected from SEQ ID NOs: 313-342. In some embodiments compositions of the invention comprise at least one set of primers i) and ii) comprising at least 50 primers selected from SEQ ID NOs: 185-248 and at least 10 primers, at least 12 primers, at least 14 primers, at least 16 primers, at least 18 primers, or at least 20 primers selected from SEQ ID NOs: 313-342. In other embodiments compositions of the invention comprise at least one set of primers i) and ii) comprising at least 50 primers selected from SEQ ID NOs: 185-248 and at least 10 primers, at least 12 primers, at least 14 primers, at least 16 primers, at least 18 primers, or at least 20 primers selected from SEQ ID NOs: 398-427.

In some embodiments compositions are provided for analysis of an immune repertoire in a sample, comprising at least one set of i) a plurality of V gene primers directed to a majority of different V gene of at least one immune receptor coding sequence comprising at least a portion of framework region 1 (FR1) within the V gene; and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein each set of i) and ii) primers directed to the same target immune receptor is configured to amplify the target immune receptor repertoire. In certain embodiments a single set of primers comprising i) and ii) is encompassed within a composition. In particular embodiments such set comprises primers directed to an immune receptor comprising a T cell receptor. In more particular embodiments such set comprises primers directed to TCR beta. In other embodiments such set comprises primers directed to TCR alpha. In still other embodiments at least two sets of primers are encompassed in a composition wherein the sets are directed to TCR alpha and TCR beta.

In particular embodiments, compositions provided include target immune receptor primer sets comprising one or more of a plurality of V gene primers directed to a sequence over an FR1 region about 70 nucleotides in length. In other particular embodiments, the one or more of a plurality of V gene primers are directed to sequences over an FR1 region about 50 nucleotides in length. In certain embodiments a target immune receptor primer set comprises V gene primers comprising about 45 to about 90 different FR-1 directed primers. In some embodiments a target immune receptor primer set comprises V gene primers comprising about 50 to about 80 different FR1-directed primers. In some embodiments a target immune receptor primer set comprises V gene primers comprising about 55 to about 75 different FR1-directed primers. In some embodiments a target immune receptor primer set comprises V gene primers comprising about 60 to about 70 different FR-1 directed primers. In some embodiments the target immune receptor primer set comprises a plurality of J gene primers. In some embodiments a target immune receptor primer set comprises at least 10 J gene primers wherein each is directed to at least a portion of a J gene within target polynucleotides. In some embodiments a target immune receptor primer set comprises at least 16 J gene primers wherein each is directed to at least a portion of a J gene within target polynucleotides. In some embodiments a target immune receptor primer set comprises about 10 to about 20 J gene primers wherein each is directed to at least a portion of a J gene within target polynucleotides. In some embodiments a target immune receptor primer set comprises about 12 to about 18 J gene primers wherein each is directed to at least a portion of a J gene within target polynucleotides. In some embodiments a target immune receptor primer set comprises about 12, 13, 14, 15, 16, 17 or 18 different J gene primers. In particular embodiments a target immune receptor primer set comprises about 16 J gene primers wherein each is directed to at least a portion of a J gene within target polynucleotides. In particular embodiments a target immune receptor primer set comprises about 14 J gene primers wherein each is directed to at least a portion of a J gene within target polynucleotides.

In particular embodiments, compositions of the invention comprise at least one set of primers comprising V gene primers i) and J gene primers ii) selected from Tables 2 and 5, respectively. In certain other embodiments compositions of the invention comprise at least one set of primers i) and ii) comprising primers selected from SEQ ID NOs: 1-89 and 313-397 or selected from SEQ ID NOs: 90-180 and 313-397. In other embodiments compositions of the invention comprise at least one set of primers i) and ii) comprising primers selected from SEQ ID NOs: 1-89 and 398-482 or selected from SEQ ID NOs: 90-180 and 398-482. In other embodiments compositions of the invention comprise at least one set of primers i) and ii) comprising primers selected from SEQ ID NOs: 1-64 and 313-397 or selected from SEQ ID NOs: 1-64 and 398-482. In other embodiments compositions of the invention comprise at least one set of primers i) and ii) comprising primers selected from SEQ ID NOs: 1-64 and 313-329 or selected from SEQ ID NOs: 1-64 and 329-342. In certain other embodiments compositions of the invention comprise at least one set of primers i) and ii) comprising primers selected from SEQ ID NOs: 1-64 and 398-414 or selected from SEQ ID NOs: 1-64 and 414-427. In other embodiments compositions of the invention comprise at least one set of primers of i) and ii) comprising primers SEQ ID NOs: 1-64 and 313-328. In still other embodiments compositions of the invention comprise at least one set of primers of i) and ii) comprising primers SEQ ID NOs: 1-64 and 398-413. In other embodiments compositions of the invention comprise at least one set of primers i) and ii) comprising primers selected from SEQ ID NOs: 90-180 and 313-342 or selected from SEQ ID NOs: 90-180 and 398-427. In still other embodiments compositions of the invention comprise at least one set of primers of i) and ii) comprising primers SEQ ID NOs: 90-153 and 398-414. In still other embodiments compositions of the invention comprise at least one set of primers of i) and ii) comprising primers SEQ ID NOs: 90-153 and 313-328. In other embodiments compositions of the invention comprise at least one set of primers of i) and ii) comprising primers selected from SEQ ID NOs: 90-155 and 313-342. In other embodiments compositions of the invention comprise at least one set of primers i) and ii) comprising primers selected from SEQ ID NOs: 90-155 and 313-329 or selected from SEQ ID NOs: 90-155 and 398-427. In certain other embodiments compositions of the invention comprise at least one set of primers i) and ii) comprising primers selected from SEQ ID NOs: 90-155 and 398-414 or selected from SEQ ID NOs: 90-155 and 414-427. In other embodiments compositions of the invention comprise at least one set of primers of i) and ii) comprising primers selected from SEQ ID NOs: 90-92, 95-180 and 398-414 or selected from SEQ ID NOs: 90-92, 95-180 and 414-427. In still other embodiments compositions of the invention comprise at least one set of primers of i) and ii) comprising primers selected from SEQ ID NOs: 90-92, 95-180 and 313-329 or selected from SEQ ID NOs: 90-92, 95-180 and 329-342. In still other embodiments compositions of the invention comprise at least one set of primers of i) and ii) comprising primers selected from SEQ ID NOs: 90-92, 95-180 and 398-413 or selected from SEQ ID NOs: 90-92, 95-180 and 398-427. In certain other embodiments compositions of the invention comprise at least one set of primers of i) and ii) comprising primers SEQ ID NOs: 90-92, 95-180 and 398-413. In still other embodiments compositions of the invention comprise at least one set of primers of i) and ii) comprising primers SEQ ID NOs: 90-92, 95-180, and 313-328.

In some embodiments compositions of the invention comprise at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 313-397. In other embodiments compositions of the invention comprise at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 398-482. In some embodiments compositions of the invention comprise at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 313-397. In other embodiments compositions of the invention comprise at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 398-482.

In some embodiments compositions of the invention comprise at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 313-342. In other embodiments compositions of the invention comprise at least one set of primers i) and ii) comprising at least 50 primers selected from SEQ ID NOs: 1-89 and at least 10 primers, at least 12 primers, at least 14 primers, at least 16 primers, at least 18 primers, or at least 20 primers selected from SEQ ID NOs: 398-427. In some embodiments compositions of the invention comprise at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 313-342. In other embodiments compositions of the invention comprise at least one set of primers i) and ii) comprising at least 60 primers selected from SEQ ID NOs: 1-89 and at least 10 primers, at least 12 primers, at least 14 primers, at least 16 primers, at least 18 primers, or at least 20 primers selected from SEQ ID NOs: 398-427.

In some embodiments compositions of the invention comprise at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 313-397. In other embodiments compositions of the invention comprise at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 398-482. In some embodiments compositions of the invention comprise at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 313-397. In other embodiments compositions of the invention comprise at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 398-482.

In some embodiments compositions of the invention comprise at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 313-342. In other embodiments compositions of the invention comprise at least one set of primers i) and ii) comprising at least 50 primers selected from SEQ ID NOs: 90-180 and at least 10 primers, at least 12 primers, at least 14 primers, at least 16 primers, at least 18 primers, or at least 20 primers selected from SEQ ID NOs: 398-427. In some embodiments compositions of the invention comprise at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 313-342. In other embodiments compositions of the invention comprise at least one set of primers i) and ii) comprising at least 60 primers selected from SEQ ID NOs: 90-180 and at least 10 primers, at least 12 primers, at least 14 primers, at least 16 primers, at least 18 primers, or at least 20 primers selected from SEQ ID NOs: 398-427.

In some embodiments compositions are provided for analysis of an immune repertoire in a sample, comprising at least one set of i) a plurality of V gene primers directed to a majority of different V gene of at least one immune receptor coding sequence comprising at least a portion of FR2 within the V gene; and ii) a plurality of J gene primers directed to a majority of different J genes of the respective target immune receptor coding sequence, wherein each set of i) and ii) primers directed to the same target immune receptor sequences is selected from the group consisting of a T cell receptor and an antibody receptor and wherein each set of i) and ii) primers directed to the same target immune receptor is configured to amplify the target immune receptor repertoire. In certain embodiments a single set of primers comprising i) and ii) is encompassed within a composition. In particular embodiments such set comprises primers directed to an immune receptor comprising a T cell receptor. In more particular embodiments such set comprises primers directed to TCR beta. In other embodiments such set comprises primers directed to TCR alpha. In still other embodiments at least two sets of primers are encompassed in a composition wherein the sets are directed to TCR alpha and TCR beta.

In particular embodiments, compositions provided include target immune receptor primer sets comprising V gene primers wherein the one or more of a plurality of V gene primers are directed to sequences over an FR2 region about 70 nucleotides in length. In other particular embodiments the one or more of a plurality of V gene primers are directed to sequences over an FR2 region about 50 nucleotides in length. In certain embodiments a target immune receptor primer set comprises V gene primers comprising about 45 to about 90 different FR2-directed primers. In some embodiments a target immune receptor primer set comprises V gene primers comprising about 30 to about 60 different FR2-directed primers. In some embodiments a target immune receptor primer set comprises V gene primers comprising about 20 to about 50 different FR2-directed primers. In some embodiments a target immune receptor primer set comprises V gene primers comprising about 60 to about 70 different FR2-directed primers. In some embodiments, a target immune receptor primer set comprises about 20 to about 30 different FR2-directed primers. In some embodiments the target immune receptor primer set comprises a plurality of J gene primers. In some embodiments a target immune receptor primer set comprises at least 10 J gene primers wherein each is directed to at least a portion of a J gene within target polynucleotides. In some embodiments a target immune receptor primer set comprises at least 16 J gene primers wherein each is directed to at least a portion of a J gene within target polynucleotides. In some embodiments a target immune receptor primer set comprises about 10 to about 20 J gene primers wherein each is directed to at least a portion of a J gene within target polynucleotides. In some embodiments a target immune receptor primer set comprises about 12 to about 18 J gene primers wherein each is directed to at least a portion of a J gene within target polynucleotides. In some embodiments a target immune receptor primer set comprises about 12, 13, 14, 15, 16, 17 or 18 different J gene primers. In particular embodiments a target immune receptor primer set comprises about 16 J gene primers wherein each is directed to at least a portion of a J gene within target polynucleotides. In particular embodiments a target immune receptor primer set comprises about 14 J gene primers wherein each is directed to at least a portion of a J gene within target polynucleotides.

In particular embodiments, compositions of the invention comprise at least one set of primers comprising V gene primers i) and J gene primers ii) selected from Tables 4 and 5, respectively. In some embodiments compositions of the invention comprise at least one set of primers i) and ii) comprising primers selected from SEQ ID NOs: 483-505 and 313-397 or selected from SEQ ID NOs: 483-505 and 398-482. In certain embodiments compositions of the invention comprise at least one set of primers i) and ii) comprising primers selected from SEQ ID NOs: 483-505 and 313-342 or selected from SEQ ID NOs: 483-505 and 398-427. In some embodiments compositions of the invention comprise at least one set of primers i) and ii) comprising primers selected from SEQ ID NOs: 483-505 and 313-329 or selected from SEQ ID NOs: 483-505 and 329-342. In certain embodiments compositions of the invention comprise at least one set of primers i) and ii) comprising primers selected from SEQ ID NOs: 363-385 and 398-414 or selected from SEQ ID NOs: 483-505 and 414-427. In other embodiments compositions of the invention comprise at least one set of primers i) and ii) comprising primers SEQ ID NOs: 483-505 and 313-328 or comprising primers SEQ ID NOs: 483-505 and 398-413.

In some embodiments compositions of the invention comprise at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 313-397. In other embodiments compositions of the invention comprise at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 398-482. In some embodiments compositions of the invention comprise at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 313-342. In other embodiments compositions of the invention comprise at least one set of primers i) and ii) comprising at least 20 primers selected from SEQ ID NOs: 483-505 and at least 10 primers, at least 12 primers, at least 14 primers, at least 16 primers, at least 18 primers, or at least 20 primers selected from SEQ ID NOs: 398-427.

In some embodiments, the composition for multiplex amplification of an immune repertoire in a sample comprises: genomic DNA from a biological sample, a DNA polymerase, dNTPs, and at least one set of:
i) (a) a plurality of V gene primers directed to a majority of different V genes of at least one immune receptor coding sequence comprising at least a portion of framework region 3 (FR3) within the V gene;
(b) a plurality of V gene primers directed to a majority of different V genes of at least one immune receptor coding sequence comprising at least a portion of framework region 2 (FR2) within the V gene, or
(c) a plurality of V gene primers directed to a majority of different V genes of at least one immune receptor coding sequence comprising at least a portion of framework region 1 (FR1) within the V gene; and
ii) a plurality of J gene primers directed to at least a portion of a majority of different J genes of the at least one immune receptor coding sequence;
wherein each set of i) and ii) primers is directed to coding sequences of the same target immune receptor gene selected from a T cell receptor or an antibody receptor; and wherein each set of i) and ii) primers directed to the same target immune receptor is configured to amplify the target immune receptor repertoire.

In some embodiments, multiple different primers including at least one modified nucleotide can be used in a single amplification reaction. For example, multiplexed primers including modified nucleotides can be added to the amplification reaction mixture, where each primer (or set of primers) selectively hybridizes to, and promotes amplification of different rearranged target nucleic acid molecules within the nucleic acid population. In some embodiments, the target specific primers can include at least one uracil nucleotide.

In some embodiments, the amplification reactions are conducted in parallel within a single reaction phase (for example, within the same amplification reaction mixture within a single well or tube). In some instances, an amplification reaction can generate a mixture of products including both the intended amplicon product as well as unintended, unwanted, nonspecific amplification artifacts such as primer-dimers. Post amplification, the reactions are then treated with any suitable agent that will selectively cleave or otherwise selectively destroy the nucleotide linkages of the modified nucleotides within the excess unincorporated primers and the amplification artifacts without cleaving or destroying the specification amplification products. For example, the primers can include uracil-containing nucleobases that can be selectively cleaved using UNG/UDG (optionally with heat and/or alkali). In some embodiments, the primers can include uracil-containing nucleotides that can be selectively cleaved using UNG and Fpg. In some embodiments, the cleavage treatment includes exposure to oxidizing conditions for selective cleavage of dithiols, treatment with RNAseH for selective cleavage of modified nucleotides including RNA-specific moieties (e.g., ribose sugars, etc.), and the like. This cleavage treatment can effectively fragment the original amplification primers and non-specific amplification products into small nucleic acid fragments that include relatively few nucleotides each. Such fragments are typically incapable of promoting further amplification at elevated temperatures. Such fragments can also be removed relatively easily from the reaction pool through the various post-amplification cleanup procedures known in the art (e.g., spin columns, NaEtOH precipitation, etc).

In some embodiments, amplification products following cleavage or other selective destruction of the nucleotide linkages of the modified nucleotides are optionally treated to generate amplification products that possess a phosphate at the 5' termini. In some embodiments, the phosphorylation treatment includes enzymatic manipulation to produce 5' phosphorylated amplification products. In one embodiment, enzymes such as polymerases can be used to generate 5' phosphorylated amplification products. For example, T4 polymerase can be used to prepare 5' phosphorylated amplicon products. Klenow can be used in conjunction with one or more other enzymes to produce amplification products with a 5' phosphate. In some embodiments, other enzymes known in the art can be used to prepare amplification products with a 5' phosphate group. For example, incubation of uracil nucleotide containing amplification products with the enzyme UDG, Fpg and T4 polymerase can be used to generate amplification products with a phosphate at the 5' termini. It will be apparent to one of skill in the art that other techniques, other than those specifically described herein, can be applied to generate phosphorylated amplicons. It is understood that such variations and modifications that are applied to practice the methods, systems, kits, compositions and apparatuses disclosed herein, without resorting to undue experimentation are considered within the scope of the disclosure.

In some embodiments, primers that are incorporated in the intended (specific) amplification products, these primers are similarly cleaved or destroyed, resulting in the formation of "sticky ends" (e.g., 5' or 3' overhangs) within the specific amplification products. Such "sticky ends" can be addressed in several ways. For example, if the specific amplification products are to be cloned, the overhang regions can be designed to complement overhangs introduced into the cloning vector, thereby enabling sticky ended ligations that are more rapid and efficient than blunt ended ligations. Alternatively, the overhangs may need to be repaired (as with several next-generation sequencing methods). Such repair can be accomplished either through secondary amplification reactions using only forward and reverse amplification primers (e.g., correspond to A and P1 primers) comprised of only natural bases. In this manner, subsequent rounds of amplification rebuild the double-stranded templates, with nascent copies of the amplicon possessing the complete sequence of the original strands prior to primer destruction. Alternatively, the sticky ends can be removed using some forms of fill-in and ligation processing, wherein the forward and reverse primers are annealed to the templates. A polymerase can then be employed to extend the primers, and then a ligase, optionally a thermostable ligase, can be utilized to connect the resulting nucleic acid strands. This could obviously be also accomplished through various other reaction pathways, such as cyclical extend-ligation, etc. In some embodiments, the ligation step can be performed using one or more DNA ligases.

In some embodiments, the amplicon library prepared using target-specific primer pairs can be used in downstream enrichment applications such as emulsion PCR, bridge PCR or isothermal amplification. In some embodiments, the amplicon library can be used in an enrichment application and a sequencing application. For example, an amplicon library can be sequenced using any suitable DNA sequencing platform, including any suitable next generation DNA sequencing platform. In some embodiments, an amplicon library can be sequenced using an Ion Torrent PGM Sequencer or an Ion Torrent S5 Sequencer (Thermo Fisher Scientific). In some embodiments, a PGM sequencer or S5 sequencer can be coupled to server that applies parameters or software to determine the sequence of the amplified target nucleic acid molecules. In some embodiments, the amplicon library can be prepared, enriched and sequenced in less than 24 hours. In some embodiments, the amplicon library can be prepared, enriched and sequenced in approximately 9 hours.

In some embodiments, methods for generating an amplicon library can include: amplifying gDNA having undergone V(D)J rearrangement of immune receptor genes using V gene-specific and J gene-specific primers to generate amplicons; purifying the amplicons from the input DNA and primers; phosphorylating the amplicons; ligating adapters to the phosphorylated amplicons; purifying the ligated amplicons; nick-translating the amplified amplicons; and purifying the nick-translated amplicons to generate the amplicon library. In some embodiments, additional amplicon library manipulations can be conducted following the step of amplification of rearranged immune receptor gene targets to generate the amplicons. In some embodiments, any combination of additional reactions can be conducted in any order, and can include: purifying; phosphorylating; ligating adapters; nick-translating; amplification and/or sequencing. In some embodiments, any of these reactions can be omitted or can be repeated. It will be readily apparent to one of skill in the art that the method can repeat or omit any one or more of the above steps. It will also be apparent to one of skill in the art that the order and combination of steps may be modified to generate the required amplicon library, and is not therefore limited to the exemplary methods provided.

A phosphorylated amplicon can be joined to an adapter to conduct a nick translation reaction, subsequent downstream amplification (e.g., template preparation), or for attachment to particles (e.g., beads), or both. For example, an adapter that is joined to a phosphorylated amplicon can anneal to an oligonucleotide capture primer which is attached to a particle, and a primer extension reaction can be conducted to generate a complimentary copy of the amplicon attached to the particle or surface, thereby attaching an amplicon to a surface or particle. Adapters can have one or more amplification primer hybridization sites, sequencing primer hybridization sites, barcode sequences, and combinations thereof. In some embodiments, amplicons prepared by the methods disclosed herein can be joined to one or more Ion Torrent™ compatible adapters to construct an amplicon library. Amplicons generated by such methods can be joined to one or more adapters for library construction to be compatible with a next generation sequencing platform. For example, the amplicons produced by the teachings of the present disclosure can be attached to adapters provided in the Ion AmpliSeq™ Library Kit 2.0 or Ion AmpliSeq™ Library Kit Plus (Thermo Fisher Scientific).

In some embodiments, amplification of rearranged immune receptor gDNA can be conducted using a 5× Ion AmpliSeg™ HiFi Master Mix. In some embodiments, the 5× Ion AmpliSeg™ HiFi Master Mix can include glycerol, dNTPs, and a DNA polymerase such as Platinum™ Taq DNA polymerase High Fidelity. In some embodiments, the 5× Ion AmpliSeg™ HiFi Master Mix can further include at least one of the following: a preservative, magnesium chloride, magnesium sulfate, tris-sulfate and/or ammonium sulfate.

In some embodiments, the multiplex amplification reaction further includes at least one PCR additive to improve on-target amplification, amplification yield, and/or the percentage of productive sequencing reads. In some embodiments, the at least one PCR additive includes at least one of potassium chloride or additional dNTPs (e.g., dATP, dCTP, dGTP, dTTP). In some embodiments, the dNTPs as a PCR additive is an equimolar mixture of dNTPs. In some embodiments, the dNTP mix as a PCR additive is an equimolar mixture of dATP, dCTP, dGTP, and dTTP In some embodiments, about 0.2 mM to about 5.0 mM dNTPs is added to the multiplex amplification reaction. In some embodiments, amplification of rearranged immune receptor gDNA can be conducted using a 5× Ion AmpliSeq™ HiFi Master Mix and an additional about 0.2 mM to about 5.0 mM dNTPs in the reaction mixture. In some embodiments, amplification of rearranged immune receptor gDNA can be conducted using a 5× Ion AmpliSeq™ HiFi Master Mix and an additional about 0.5 mM to about 4 mM, about 0.5 mM to about 3 mM, about 0.5 mM to about 2.5 mM, about 0.5 mM to about 1.0 mM, about 0.75 mM to about 1.25 mM, about 1.0 mM to about 1.5 mM, about 1.0 to about 2.0 mM, about 2.0 mM to about 3.0 mM, about 1.25 to about 1.75 mM, about 1.3 to about 1.8 mM, about 1.4 mM to about 1.7 mM, or about 1.5 to about 2.0 mM dNTPs in the reaction mixture. In some embodiments, amplification of rearranged immune receptor gDNA can be conducted using a 5× Ion AmpliSeq™ HiFi Master Mix and an additional about 0.2 mM, about 0.4 mM, about 0.6 mM, about 0.8 mM, about 1.0 mM, about 1.2 mM, about 1.4 mM, about 1.6 mM, about 1.8 mM, about 2.0 mM, about 2.2 mM, about 2.4 mM, about 2.6 mM, about 2.8 mM, about 3.0 mM, about 3.5 mM, or about 4.0 mM dNTPs in the reaction mixture. In some embodiments, about 10 mM to about 200 mM potassium chloride is added to the multiplex amplification reaction. In some embodiments, amplification of rearranged immune receptor gDNA can be conducted using a 5× Ion AmpliSeq™ HiFi Master Mix and an additional about 10 mM to about 200 mM potassium chloride in the reaction mixture. In some embodiments, amplification of rearranged immune receptor gDNA can be conducted using a 5× Ion AmpliSeq™ HiFi Master Mix and an additional about 10 mM to about 60 mM, about 20 mM to about 70 mM, about 30 mM to about 80 mM, about 40 mM to about 90 mM, about 50 mM to about 100 mM, about 60 mM to about 120 mM, about 80 mM to about 140 mM, about 50 mM to about 150 mM, about 150 mM to about 200 mM or about 100 mM to about 200 mM potassium chloride in the reaction mixture. In some embodiments, amplification of rearranged immune receptor gDNA can be conducted using a 5× Ion AmpliSeq™ HiFi Master Mix and an additional about 10 mM, about 20 mM, about 30 mM, about 40 mM, about 50 mM, about 60 mM, about 70 mM, about 80 mM, about 90 mM, about 100 mM, about 120 mM, about 140 mM, about 150 mM, about 160 mM, about 180 mM, or about 200 mM potassium chloride in the reaction mixture.

In some embodiments, phosphorylation of the amplicons can be conducted using a FuPa reagent. In some embodiments, the FuPa reagent can include a DNA polymerase, a DNA ligase, at least one uracil cleaving or modifying enzyme, and/or a storage buffer. In some embodiments, the FuPa reagent can further include at least one of the following: a preservative and/or a detergent.

In some embodiments, phosphorylation of the amplicons can be conducted using a FuPa reagent. In some embodiments, the FuPa reagent can include a DNA polymerase, at least one uracil cleaving or modifying enzyme, an antibody and/or a storage buffer. In some embodiments, the FuPa reagent can further include at least one of the following: a preservative and/or a detergent. In some embodiments, the antibody is provided to inhibit the DNA polymerase and 3'-5' exonuclease activities at ambient temperature.

In some embodiments, the amplicon library produced by the teachings of the present disclosure are sufficient in yield to be used in a variety of downstream applications including the Ion Chef™ instrument and the Ion S5™ Sequencing Systems (Thermo Fisher Scientific).

It will be apparent to one of ordinary skill in the art that numerous other techniques, platforms or methods for clonal amplification such as wildfire PCR and bridge amplification can be used in conjunction with the amplified target sequences of the present disclosure. It is also envisaged that one of ordinary skill in art upon further refinement or optimization of the conditions provided herein can proceed directly to nucleic acid sequencing (for example using the Ion PGM™ or Ion S5™ or Ion Proton™ sequencers, Thermo Fisher Scientific) without performing a clonal amplification step.

In some embodiments, at least one of the amplified targets sequences to be clonally amplified can be attached to a support or particle. The support can be comprised of any suitable material and have any suitable shape, including, for example, planar, spheroid or particulate. In some embodiments, the support is a scaffolded polymer particle as described in U.S. Published App. No. 20100304982, hereby incorporated by reference in its entirety.

In some embodiments, a kit is provided for amplifying multiple rearranged immune receptor gene sequences from a population of nucleic acid molecules, such as gDNA molecules, in a single reaction. In some embodiments, the kit includes a plurality of target-specific primer pairs containing one or more cleavable groups, one or more DNA polymerases, a mixture of dNTPs and at least one cleaving reagent. In one embodiment, the cleavable group is 8-oxo-deoxyguanosine, deoxyuridine or bromodeoxyuridine. In some embodiments, the at least one cleaving reagent includes RNaseH, uracil DNA glycosylase, Fpg or alkali. In one embodiment, the cleaving reagent is uracil DNA glycosylase. In some embodiments, the kit is provided to perform multiplex PCR in a single reaction chamber or vessel. In some embodiments, the kit includes at least one DNA polymerase, which is a thermostable DNA polymerase. In some embodiments, the concentration of the one or more DNA polymerases is present in a 3-fold excess as compared to a single PCR reaction. In some embodiments, the final concentration of each target-specific primer pair is present at about 5 nM to about 2000 nM. In some embodiments, the final concentration of each target-specific primer pair is present at about 25 nM to about 50 nM or about 100 nM to about 800 nM. In some embodiments, the final concentration of each target-specific primer pair is present at about 50 nM to about 400 nM or about 50 nM to about 200 nM. In some embodiments, the final concentration of each target-specific primer pair is present at about 200 nM or about 400 nM. In some embodiments, the kit includes at least one PCR additive, for example a potassium salt or additional dNTPs. In some embodiments, the kit includes a potassium chloride solution at about 100 mM to about 1M as the at least one PCR additive. In some embodiments, the kit includes a dNTP mix at about 2 mM to about 50 mM as the at least one PCR additive. In some embodiments, the kit provides amplification of immune repertoire expression sequences from TCR beta, TCR alpha, TCR gamma, TCR delta, immunoglobulin heavy chain gamma, immunoglobulin heavy chain mu, immunoglobulin heavy chain alpha, immunoglobulin heavy chain delta, immunoglobulin heavy chain epsilon, immunoglobulin light chain lambda, or immunoglobulin light chain kappa from a population of nucleic acid molecules in a single reaction chamber. In particular embodiments, a provided kit is a test kit. In some embodiments, the kit further comprises one or more adapters, barcodes, and/or antibodies.

TABLE 2

| Name | Sequence | SEQ ID NO. |
|---|---|---|
| TRBV_F1 | AAAATACCTGGTCACACAGACGGGA | 1 |
| TRBV_F2 | AAGATACCGGGTTACCCAGTTTGGA | 2 |
| TRBV_F3 | ACTCAAACTCCAAGACATCTGATCAAAACG | 3 |
| TRBV_F4 | AGAATCCCAGACACAAGATCACAAA | 4 |
| TRBV_F5 | AGAGTCCAAGACACAAGATCACAGA | 5 |
| TRBV_F6 | AGTCCCCAAGACATCTGATCAGAGA | 6 |
| TRBV_F7 | ATCAATGGCCAGCGACCCTGG | 7 |
| TRBV_F8 | CCAAAGTCCCACACACCTGATCAAA | 8 |
| TRBV_F9 | CCCAGACACCAAAATACCTGG | 9 |
| TRBV_F10 | CTCAACATCCGAGTAGGGTTATCTGTA | 10 |
| TRBV_F11 | CTCAGTCCCCAAAGTACCTGT | 11 |
| TRBV_F12 | CTGGAATCACCCAGAGCCC | 12 |
| TRBV_F13 | CTGGAGTCTCCCACAACCC | 13 |
| TRBV_F14 | CTGGAGTCTCCCAGAACCC | 14 |
| TRBV_F15 | CTGGAGTCTCCCAGGACCC | 15 |
| TRBV_F16 | CTGGAGTCACTCAAACTCCAAGATATCT | 16 |
| TRBV_F17 | GAAAGCCAGTGACCCTGAGTTG | 17 |
| TRBV_F18 | CCCAGAGCTCGAGATATCTAGTCAA | 18 |
| TRBV_F19 | AAAAGCCAAGCAGGGATATCTGTC | 19 |
| TRBV_F20 | AAAATACCTGGTCACACAGATGGGA | 20 |
| TRBV_F21 | AAAATTCCACGTCCTGAAGACAGG | 21 |
| TRBV_F22 | AAAATTCCAGGTCCTGAAGACAGG | 22 |
| TRBV_F23 | AAAATTCCACATCCTGAAGACAGGAC | 23 |
| TRBV_F24 | AAAGCACCTGATCACAGCAACTG | 24 |
| TRBV_F25 | AACATCCGAGCAGGGTTATCTGTA | 25 |
| TRBV_F26 | AACATCCGAGCTGGGTTATCTGTA | 26 |
| TRBV_F27 | AACCCAAGATACCTCATCACAGTGAC | 27 |

TABLE 2-continued

| Name | Sequence | SEQ ID NO. |
|---|---|---|
| TRBV_F28 | AAGACACAGAATCATTGGGACAGG | 28 |
| TRBV_F29 | AAGCATGAGGTGACAGAAATGGGA | 29 |
| TRBV_F30 | AAGGCACAAGGTGACAGAGATG | 30 |
| TRBV_F31 | AATACCTGGTCACACAGATGGGAA | 31 |
| TRBV_F32 | AATTCTCAAGACACAGAATCATTGGGACA | 32 |
| TRBV_F33 | ACAAAGTCCCACACACCTGATCAAA | 33 |
| TRBV_F34 | ACACAAGGTCACCAACATGGG | 34 |
| TRBV_F35 | ACACCAAGACACCTGGTCATG | 35 |
| TRBV_F36 | ACCAACATCTCAGATCCTGGCA | 36 |
| TRBV_F37 | ACCAGACCCCAAGATACCTTGTTATA | 37 |
| TRBV_F38 | ACCCCAAGGAATAGGATCACAAAGA | 38 |
| TRBV_F39 | ACCCCCAGTAACAAGGTCACA | 39 |
| TRBV_F40 | ACCTAGACTTCTGGTCAAAGCAAGTG | 40 |
| TRBV_F41 | ACCTAGATTTCTGGTCAAAGCAAATGA | 41 |
| TRBV_F42 | ACTCCAGGATATTTGGTCAAAGGAAAAGGAA | 42 |
| TRBV_F43 | AGACACCAAAACACCTGGTCATG | 43 |
| TRBV_F44 | AGACTATTCATCAATGGCCAGCGA | 44 |
| TRBV_F45 | AGAGCCCAAGATACAAGATCACAGA | 45 |
| TRBV_F46 | AGCCACAGCGTAATAGAGAAGGG | 46 |
| TRBV_F47 | AGGACATTTGGTCAAAGGAAAAGGAC | 47 |
| TRBV_F48 | AGTCCCCAAGACATCTGATCAAAGA | 48 |
| TRBV_F49 | AGTCCCTGAGACACAAGGTAGCA | 49 |
| TRBV_F50 | AGTCTCCCAGATATAAGATTATAGAGAAAGGC | 50 |
| TRBV_F51 | AGTCTCCCAGGTACAAAGTCACA | 51 |
| TRBV_F52 | AGTGGTTCAGTCTCCCAGATATAAGATTATAG | 52 |
| TRBV_F53 | AGTAACAAGGTCACAGAGAAGGGA | 53 |
| TRBV_F54 | CAAAATTCCGGGTCCTGAAGACA | 54 |
| TRBV_F55 | CAAGACACCTGGTCAGGAGGAG | 55 |
| TRBV_F56 | CAGACTCCAAAACATCTTGTCAGAGG | 56 |
| TRBV_F57 | CAGCCATCAGGTCACACAGATG | 57 |
| TRBV_F58 | CCAAGGTACAAAGTCGCAAAGAGG | 58 |
| TRBV_F59 | CCCAAAATTCCGCATCCTGAAGATA | 59 |
| TRBV_F60 | CCCAGTCCCCCAGATATAAGATTACA | 60 |
| TRBV_F61 | CCCTAGGTACAAAGTCGCAAAGAGA | 61 |
| TRBV_F62 | CGCCATGAGGTGACAGAGATGG | 62 |
| TRBV_F63 | CGGCACGAGGTGACAGAGATG | 63 |
| TRBV_F64 | GTCACCCAGGCACAAAGTGACA | 64 |
| TRBV_F65 | CAAGATATCTGATCAAAACGAGAGGACAG | 65 |
| TRBV_F66 | CCAAGATATCTGATCAAAACGAGAGGAC | 66 |
| TRBV_F67 | CTCCAAGATATCTGATCAAAACGAGAGG | 67 |
| TRBV_F68 | GAGAGGACAGCAAGTGACACTG | 68 |
| TRBV_F69 | GAGTCACTCAAACTCCAAGATATCTGATCA | 69 |
| TRBV_F70 | GCTGGAGTCACTCAAACTCCAAG | 70 |
| TRBV_F71 | GGAGTCACTCAAACTCCAAGATATCTGAT | 71 |
| TRBV_F72 | GGCTGGAGTCACTCAAACTCC | 72 |
| TRBV_F73 | CATGGTCATCCAGAACCCAAGATAC | 73 |
| TRBV_F74 | CCATGGTCATCCAGAACCCAAG | 74 |
| TRBV_F75 | GATGCCATGGTCATCCAGAACC | 75 |
| TRBV_F76 | GGAAAGCCAGTGACCCTGAG | 76 |
| TRBV_F77 | GGTTACCCAGTTTGGAAAGCCA | 77 |
| TRBV_F78 | GTTTGGAAAGCCAGTGACCCT | 78 |
| TRBV_F79 | GTTACCCAGTTTGGAAAGCCAGT | 79 |
| TRBV_F80 | TGCCATGGTCATCCAGAACC | 80 |
| TRBV_F81 | TTACCCAGTTTGGAAAGCCAGTG | 81 |
| TRBV_F82 | TTTGGAAAGCCAGTGACCCTG | 82 |
| TRBV_F83 | AGAGCTGAGATATCTAGTCAAAGGAC | 83 |
| TRBV_F84 | AGCTCGAGATATCTAGTCAAAGGACG | 84 |
| TRBV_F85 | CGAGATATCTAGTCAAAGGACGGGA | 85 |
| TRBV_F86 | GAAAGTAACCCAGAGCTCGAGATATCTAG | 86 |
| TRBV_F87 | GATGTGAAAGTAACCCAGAGCTCG | 87 |
| TRBV_F88 | GTAACCCAGAGCTCGAGATATCTAGTC | 88 |
| TRBV_F89 | GTGAAAGTAACCCAGAGCTCGAG | 89 |
| TRBV_F90 | AAAAUACCTGGUCACACAGACGGGA | 90 |
| TRBV_F91 | AAGATACCGGGUTACCCAGTTUGGA | 91 |
| TRBV_F92 | ACTCAAACUCCAAGACATCTGAUCAAAACG | 92 |
| TRBV_F93 | AGAAUCCCAGACACAAGATCACAAA | 93 |
| TRBV_F94 | AGAGUCCAAGACACAAGATCACAGA | 94 |
| TRBV_F95 | AGTCCCCAAGACAUCTGATCAGAGA | 95 |
| TRBV_F96 | ATCAAUGGCCAGCGACCCUGG | 96 |
| TRBV_F97 | CCAAAGUCCCACACACCTGAUCAAA | 97 |
| TRBV_F98 | CCCAGACACCAAAAUACCUGG | 98 |
| TRBV_F99 | CTCAACATCCGAGUAGGGUTATCTGUA | 99 |
| TRBV_F100 | CTCAGUCCCCAAAGTACCUGT | 100 |
| TRBV_F101 | CUGGAAUCACCCAGAGCCC | 101 |
| TRBV_F102 | CUGGAGTCUCCCACAACCC | 102 |
| TRBV_F103 | CUGGAGTCUCCCAGAACCC | 103 |

TABLE 2-continued

| Name | Sequence | SEQ ID NO. |
|---|---|---|
| TRBV_F104 | CUGGAGUCUCCCAGGACCC | 104 |
| TRBV_F105 | CTGGAGTCACUCAAACTCCAAGATAUCT | 105 |
| TRBV_F106 | GAAAGCCAGUGACCCUGAGTUG | 106 |
| TRBV_F107 | CCCAGAGCUCGAGAUAUCUAGUCAA | 107 |
| TRBV_F108 | AAAAGCCAAGCAGGGAUAUCUGUC | 108 |
| TRBV_F109 | AAAAUACCUGGUCACACAGAUGGGA | 109 |
| TRBV_F110 | AAAAUCCACGUCCUGAAGACAGG | 110 |
| TRBV_F111 | AAAAUCCAGGUCCUGAAGACAGG | 111 |
| TRBV_F112 | AAAAUCCACAUCCUGAAGACAGGAC | 112 |
| TRBV_F113 | AAAGCACCUGAUCACAGCAACUG | 113 |
| TRBV_F114 | AACAUCCGAGCAGGGUAUCUGUA | 114 |
| TRBV_F115 | AACAUCCGAGCUGGGUUAUCUGUA | 115 |
| TRBV_F116 | AACCCAAGAUACCUCAUCACAGUGAC | 116 |
| TRBV_F117 | AAGACACAGAAUCAUGGGACAGG | 117 |
| TRBV_F118 | AAGCAUGAGGUGACAGAAAUGGGA | 118 |
| TRBV_F119 | AAGGCACAAGGUGACAGAGAUG | 119 |
| TRBV_F120 | AAUACCUGGUCACACAGAUGGGAA | 120 |
| TRBV_F121 | AAUUCUCAAGACACAGAAUCAUGGGACA | 121 |
| TRBV_F122 | ACAAAGUCCCACACACCUGAUCAAA | 122 |
| TRBV_F123 | ACACAAGGUCACCAACAUGGG | 123 |
| TRBV_F124 | ACACCAAGACACCUGGUCAUG | 124 |
| TRBV_F125 | ACCAACAUCUCAGAUCCUGGCA | 125 |
| TRBV_F126 | ACCAGACCCCAAGAUACCUUGUUAUA | 126 |
| TRBV_F127 | ACCCCAAGGAAUAGGAUCACAAAGA | 127 |
| TRBV_F128 | ACCCCCAGUAACAAGGUCACA | 128 |
| TRBV_F129 | ACCUAGACUUCUGGUCAAAGCAAGUG | 129 |
| TRBV_F130 | ACCUAGAUUUCUGGUCAAAGCAAUGA | 130 |
| TRBV_F131 | ACUCCAGGAUAUUUGGUCAAAGGAAAAGGAA | 131 |
| TRBV_F132 | AGACACCAAAACACCUGGUCAUG | 132 |
| TRBV_F133 | AGACUAUUCAUCAAUGGCCAGCGA | 133 |
| TRBV_F134 | AGAGCCCAAGAUACAAGAUCACAGA | 134 |
| TRBV_F135 | AGCCACAGCUAAUAGAGAAGGG | 135 |
| TRBV_F136 | AGGACAUUGGUCAAAGGAAAAGGAC | 136 |
| TRBV_F137 | AGUCCCCAAGACAUCUGAUCAAAGA | 137 |
| TRBV_F138 | AGUCCCUGAGACACAAGGUAGCA | 138 |
| TRBV_F139 | AGUCUCCAGAUAUAAGAUUAUAGAGAAAAGGC | 139 |
| TRBV_F140 | AGUCUCCCAGGUACAAAGUCACA | 140 |
| TRBV_F141 | AGUGGUUCAGUCUCCCAGAUAUAAGAUUAUAG | 141 |
| TRBV_F142 | AGUAACAAGGUCACAGAGAAGGGA | 142 |
| TRBV_F143 | CAAAAUCCGGGUCCUGAAGACA | 143 |
| TRBV_F144 | CAAGACACCUGGUCAGGAGGAG | 144 |
| TRBV_F145 | CAGACUCCAAAACAUCUUGUCAGAGG | 145 |
| TRBV_F146 | CAGCCAUCAGGUCACACAGAUG | 146 |
| TRBV_F147 | CCAAGGUACAAAGUCGCAAAGAGG | 147 |
| TRBV_F148 | CCCAAAAUUCCGCAUCCUGAAGAUA | 148 |
| TRBV_F149 | CCCAGUCCCCCAGAUAUAAGAUUACA | 149 |
| TRBV_F150 | CCCUAGGUACAAAGUCGCAAAGAGA | 150 |
| TRBV_F151 | CGCCAUGAGGUGACAGAGAUGG | 151 |
| TRBV_F152 | CGGCACGAGGUGACAGAGAUG | 152 |
| TRBV_F153 | GUCACCCAGGCACAAAGUGACA | 153 |
| TRBV_F154 | AGAGUCCAAGACACAAGAUCACAGA | 154 |
| TRBV_F155 | AGAAUCCCAGACACAAGAUCACAAA | 155 |
| TRBV_F156 | CUCCAAGAUAUCUGAUCAAAACGAGAGG | 156 |
| TRBV_F157 | GAGAGGACAGCAAGUGACACUG | 157 |
| TRBV_F158 | GAGUCACUCAAACUCCAAGAUAUCUGAUCA | 158 |
| TRBV_F159 | GCUGGAGUCACUCAAACUCCAAG | 159 |
| TRBV_F160 | GGAGUCACUCAAACUCCAAGAUAUCUGAT | 160 |
| TRBV_F161 | GGCUGGAGUCACUCAAACUCC | 161 |
| TRBV_F162 | CAUGGUCAUCCAGAACCCAAGAUAC | 162 |
| TRBV_F163 | CCAUGGUCAUCCAGAACCCAAG | 163 |
| TRBV_F164 | GAUGCCAUGGUCAUCCAGAACC | 164 |
| TRBV_F165 | GGAAAGCCAGUGACCCUGAG | 165 |
| TRBV_F166 | GGUUACCCAGUUGGAAAGCCA | 166 |
| TRBV_F167 | GUUGGAAAGCCAGUGACCCU | 167 |
| TRBV_F168 | GUACCCAGUUGGAAAGCCAGU | 168 |
| TRBV_F169 | TGCCAUGGUCAUCCAGAACC | 169 |
| TRBV_F170 | TTACCCAGUUGGAAAGCCAGUG | 170 |
| TRBV_F171 | TTTGAAAGCCAGUGACCCUG | 171 |
| TRBV_F172 | AGAGCUCGAGAUAUCUAGUCAAAGGAC | 172 |
| TRBV_F173 | AGCUCGAGAUAUCUAGUCAAAGGACG | 173 |
| TRBV_F174 | CGAGAUAUCUAGUCAAAGGACGGGA | 174 |
| TRBV_F175 | GAAAGUAACCCAGAGCUCGAGAUAUCUAG | 175 |
| TRBV_F176 | GAUGUGAAAGUAACCCAGAGCUCG | 176 |
| TRBV_F177 | GUAACCCAGAGCUCGAGAUAUCUAGUC | 177 |
| TRBV_F178 | GUGAAAGUAACCCAGAGCUCGAG | 178 |

TABLE 2-continued

| Name | Sequence | SEQ ID NO. |
|---|---|---|
| TRBV_F179 | CAAGAUAUCUGAUCAAAACGAGAGGACAG | 179 |
| TRBV_F180 | CCAAGAUAUCUGAUCAAAACGAGAGGAC | 180 |

<br>



TABLE 2-continued

| Name | Sequence | SEQ ID NO. |
|---|---|---|
| TRBV_F179 | CAAGAUAUCUGAUCAAAACGAGAGGACAG | 179 |
| TRBV_F180 | CCAAGAUAUCUGAUCAAAACGAGAGGAC | 180 |

TABLE 3

| Name | Sequence | SEQ ID NO. |
|---|---|---|
| TRBV_F185 | AATCTTCACATCAATTCCCTGGAG | 185 |
| TRBV_F186 | ACATCCGCTCACCAGGC | 186 |
| TRBV_F187 | ACCTACACACCCTGCAGC | 187 |
| TRBV_F188 | AGGCTGGAGTCAGCTGC | 188 |
| TRBV_F189 | AGGTGCAGCCTGCAGAA | 189 |
| TRBV_F190 | ATGAATGTGAGCACCTTGGAG | 190 |
| TRBV_F191 | ATGAATGTGAGTGCCTTGGAG | 191 |
| TRBV_F192 | CAAGCTGGAGTCAGCTGC | 192 |
| TRBV_F193 | CATGAGCTCCTTGGAGCTG | 193 |
| TRBV_F194 | CATTCTGAGTTCTAAGAAGCTCCTC | 194 |
| TRBV_F195 | CCTGACCCTGAAGTCTGCT | 195 |
| TRBV_F196 | CCTGAGCTCTCTGGAGCTG | 196 |
| TRBV_F197 | CTAGACATCCGCTCACCAGGC | 197 |
| TRBV_F198 | CTCAAGATCCAGCCTGCAAAG | 198 |
| TRBV_F199 | CTCAAGATCCAGCCTGCAGAG | 199 |
| TRBV_F200 | CTCACGTTGGCGTCTGCTGTA | 200 |
| TRBV_F201 | CTCACTCTGGAGTCAGCTACC | 201 |
| TRBV_F202 | CTCACTCTGGAGTCCGCTACC | 202 |
| TRBV_F203 | CTCACTCTGGAGTCTGCTGCC | 203 |
| TRBV_F204 | CTCACTGTGACATCGGCCCAA | 204 |
| TRBV_F205 | CTGAAGATCCAGCCCTCAGAA | 205 |
| TRBV_F206 | CTGAAGATCCAGCCTGCAGAG | 206 |
| TRBV_F207 | CTGAAGATCCGGTCCACAAAG | 207 |
| TRBV_F208 | CTGAATGTGAACGCCTTGTTG | 208 |
| TRBV_F209 | CTGAATGTGAACGCCTTGGAG | 209 |
| TRBV_F210 | CTGACAGTGACCAGTGCCCAT | 210 |
| TRBV_F211 | CTGACAGTGACCTGTGCCCAT | 211 |
| TRBV_F212 | CTGACCCTGAAGTCTGCCAGC | 212 |
| TRBV_F213 | CTGACTGTGAGCAACATGAGC | 213 |
| TRBV_F214 | CTGAGGATCCAGCAGGTAGTG | 214 |
| TRBV_F215 | CTGAGGATCCAGCCCATGGAA | 215 |

TABLE 3-continued

| Name | Sequence | SEQ ID NO. |
|---|---|---|
| TRBV_F216 | CTGAGGATCCAGCCCTCAGAA | 216 |
| TRBV_F217 | CTGGCAATCCTGTCCTCAGAA | 217 |
| TRBV_F218 | CTGGCAATCCTGTCCTCGGAA | 218 |
| TRBV_F219 | CTGTCCCTAGAGTCTGCCATC | 219 |
| TRBV_F220 | CTCAAGATCCAGCCAGCAGAG | 220 |
| TRBV_F221 | CTGAAGATCCATCCCGCAGAG | 221 |
| TRBV_F222 | CTGAAGATCCAGCGCACACAG | 222 |
| TRBV_F223 | CTGAAGATCCAGCGCACAGAG | 223 |
| TRBV_F224 | CTGAAGTTCCAGCGCACACAG | 224 |
| TRBV_F225 | CTGACGATTCAGCGCACAGAG | 225 |
| TRBV_F226 | CTGACGATCCAGCGCACA | 226 |
| TRBV_F227 | CTGACTGTGAGCAACAGGAGA | 227 |
| TRBV_F228 | CTGATTCTGGAGTCCGCCAGC | 228 |
| TRBV_F229 | GCCTTGAGATCCAGGCTACG | 229 |
| TRBV_F230 | GGCTGGAGTTGGCTGCT | 230 |
| TRBV_F231 | GGTTGGAGTCGGCTGCT | 231 |
| TRBV_F232 | TCACCTACACGCCCTGC | 232 |
| TRBV_F233 | TCAGGCTGCTGTCGGCT | 233 |
| TRBV_F234 | TCAGGCTGGAGTCGGCT | 234 |
| TRBV_F235 | TCAGGCTGGTGTCGGCT | 235 |
| TRBV_F236 | TCATCCTGAGTTCTAAGAAGCTCC | 236 |
| TRBV_F237 | TCCTGAGTTCTAAGAAGCTCCTC | 237 |
| TRBV_F238 | TCTCAAGATCCAACCTGCAAAG | 238 |
| TRBV_F239 | TGACCCTGGAGTCTGCC | 239 |
| TRBV_F240 | TGATCCTGGAGTCGCCC | 240 |
| TRBV_F241 | TGTGGTCGCACTGCAGC | 241 |
| TRBV_F242 | TTGGAGATCCAGTCCACGGAG | 242 |
| TRBV_F243 | TTGGAGATCCAGCGCACAGAG | 243 |
| TRBV_F244 | CATGAGCTCCTTGGAGCTGG | 244 |
| TRBV_F245 | AACATGAGCTCCTTGGAGCTG | 245 |
| TRBV_F246 | GAACATGAGCTCCTTGGAGCTG | 246 |
| TRBV_F247 | TGAACTGAACATGAGCTCCTTGG | 247 |
| TRBV_F248 | CTGAACTGAACATGAGCTCCTTGG | 248 |
| TRBV_F249 | AATCTTCACAUCAAUUCCCUGGAG | 249 |
| TRBV_F250 | ACAUCCGCUCACCAGGC | 250 |
| TRBV_F251 | ACCUACACACCCUGCAGC | 251 |
| TRBV_F252 | AGGCUGGAGUCAGCUGC | 252 |
| TRBV_F253 | AGGUGCAGCCUGCAGAA | 253 |

TABLE 3-continued

| Name | Sequence | SEQ ID NO. |
|---|---|---|
| TRBV_F254 | ATGAATGUGAGCACCTUGGAG | 254 |
| TRBV_F255 | ATGAATGUGAGTGCCTUGGAG | 255 |
| TRBV_F256 | CAAGCUGGAGTCAGCUGC | 256 |
| TRBV_F257 | CATGAGCUCCTTGGAGCUG | 257 |
| TRBV_F258 | CATTCTGAGTTCUAAGAAGCUCCUC | 258 |
| TRBV_F259 | CCTGACCCUGAAGTCUGCT | 259 |
| TRBV_F260 | CCTGAGCUCTCTGGAGCUG | 260 |
| TRBV_F261 | CTAGACAUCCGCUCACCAGGC | 261 |
| TRBV_F262 | CTCAAGAUCCAGCCUGCAAAG | 262 |
| TRBV_F263 | CTCAAGAUCCAGCCUGCAGAG | 263 |
| TRBV_F264 | CTCACGTUGGCGTCUGCTGUA | 264 |
| TRBV_F265 | CTCACTCUGGAGTCAGCUACC | 265 |
| TRBV_F266 | CTCACTCUGGAGTCCGCUACC | 266 |
| TRBV_F267 | CTCACTCUGGAGTCTGCUGCC | 267 |
| TRBV_F268 | CTCACUGTGACAUCGGCCCAA | 268 |
| TRBV_F269 | CTGAAGAUCCAGCCCUCAGAA | 269 |
| TRBV_F270 | CTGAAGAUCCAGCCUGCAGAG | 270 |
| TRBV_F271 | CTGAAGAUCCGGUCCACAAAG | 271 |
| TRBV_F272 | CTGAATGUGAACGCCUUGTUG | 272 |
| TRBV_F273 | CTGAATGUGAACGCCUGGAG | 273 |
| TRBV_F274 | CTGACAGUGACCAGUGCCCAT | 274 |
| TRBV_F275 | CTGACAGUGACCUGUGCCCAT | 275 |
| TRBV_F276 | CTGACCCUGAAGTCUGCCAGC | 276 |
| TRBV_F277 | CTGACTGUGAGCAACAUGAGC | 277 |
| TRBV_F278 | CTGAGGAUCCAGCAGGUAGUG | 278 |
| TRBV_F279 | CTGAGGAUCCAGCCCAUGGAA | 279 |
| TRBV_F280 | CTGAGGAUCCAGCCCUCAGAA | 280 |
| TRBV_F281 | CTGGCAAUCCTGTCCUCAGAA | 281 |
| TRBV_F282 | CTGGCAAUCCTGTCCUCGGAA | 282 |
| TRBV_F283 | CTGTCCCUAGAGTCTGCCAUC | 283 |
| TRBV_F284 | CUCAAGAUCCAGCCAGCAGAG | 284 |
| TRBV_F285 | CUGAAGATCCAUCCCGCAGAG | 285 |
| TRBV_F286 | CUGAAGAUCCAGCGCACACAG | 286 |
| TRBV_F287 | CUGAAGAUCCAGCGCACAGAG | 287 |
| TRBV_F288 | CUGAAGTCCAGCGCACACAG | 288 |
| TRBV_F289 | CUGACGAUCAGCGCACAGAG | 289 |
| TRBV_F290 | CUGACGAUCCAGCGCACA | 290 |
| TRBV_F291 | CUGACTGUGAGCAACAGGAGA | 291 |

TABLE 3-continued

| Name | Sequence | SEQ ID NO. |
|---|---|---|
| TRBV_F292 | CUGATTCTGGAGUCCGCCAGC | 292 |
| TRBV_F293 | GCCTTGAGAUCCAGGCUACG | 293 |
| TRBV_F294 | GGCTGGAGUTGGCUGCT | 294 |
| TRBV_F295 | GGTTGGAGUCGGCUGCT | 295 |
| TRBV_F296 | TCACCUACACGCCCUGC | 296 |
| TRBV_F297 | TCAGGCUGCTGUCGGCT | 297 |
| TRBV_F298 | TCAGGCUGGAGUCGGCT | 298 |
| TRBV_F299 | TCAGGCUGGTGUCGGCT | 299 |
| TRBV_F300 | TCATCCTGAGUTCUAAGAAGCUCC | 300 |
| TRBV_F301 | TCCTGAGTTCUAAGAAGCUCCUC | 301 |
| TRBV_F302 | TCTCAAGAUCCAACCUGCAAAG | 302 |
| TRBV_F303 | TGACCCUGGAGTCUGCC | 303 |
| TRBV_F304 | TGATCCUGGAGTCGCCC | 304 |
| TRBV_F305 | TGTGGUCGCACUGCAGC | 305 |
| TRBV_F306 | TTGGAGAUCCAGUCCACGGAG | 306 |
| TRBV_F307 | TUGGAGAUCCAGCGCACAGAG | 307 |
| TRBV_F308 | CATGAGCUCCTTGGAGCUGG | 308 |
| TRBV_F309 | AACATGAGCUCCTTGGAGCUG | 309 |
| TRBV_F310 | GAACATGAGCUCCTTGGAGCUG | 310 |
| TRBV_F311 | TGAACTGAACAUGAGCUCCUGG | 311 |
| TRBV_F312 | CTGAACTGAACAUGAGCUCCUGG | 312 |

TABLE 4

| Name | Sequence | SEQ ID NO. |
|---|---|---|
| TRBV_F313 | AACTATGTTTTGGTATCGTCA | 483 |
| TRBV_F314 | CACGATGTTCTGGTACCGTCAGCA | 484 |
| TRBV_F315 | CAGTGTGTCCTGGTACCAACAG | 485 |
| TRBV_F316 | AACCCTTTATTGGTACCGACA | 486 |
| TRBV_F317 | ATCCCTTTTTTGGTACCAACAG | 487 |
| TRBV_F318 | AACCCTTTATTGGTATCAACAG | 488 |
| TRBV_F319 | CGCTATGTATTGGTACAAGCA | 489 |
| TRBV_F320 | CTCCCGTTTTCTGGTACAGACAGAC | 490 |
| TRBV_F321 | CGCTATGTATTGGTATAAACAG | 491 |
| TRBV_F322 | TTATGTTTACTGGTATCGTAAGAAGC | 492 |
| TRBV_F323 | CAAAATGTACTGGTATCAACAA | 493 |
| TRBV_F324 | ATACATGTACTGGTATCGACAAGAC | 494 |
| TRBV_F325 | GGCCATGTACTGGTATAGACAAG | 495 |
| TRBV_F326 | GTATATGTCCTGGTATCGACAAGA | 496 |

TABLE 4-continued

| Name | Sequence | SEQ ID NO. |
|---|---|---|
| TRBV_F327 | TAACCTTTATTGGTATCGACGTGT | 497 |
| TRBV_F328 | GGCCATGTACTGGTACCGACA | 498 |
| TRBV_F329 | TCATGTTTACTGGTATCGGCAG | 499 |
| TRBV_F330 | TTATGTTTATTGGTATCAACAGAATCA | 500 |
| TRBV_F331 | CAACCTATACTGGTACCGACA | 501 |
| TRBV_F332 | TACCCTTTACTGGTACCGGCAG | 502 |
| TRBV_F333 | ATACTTCTATTGGTACAGACAAATCT | 503 |
| TRBV_F334 | CACGGTCTACTGGTACCAGCA | 504 |
| TRBV_F335 | CGTCATGTACTGGTACCAGCA | 505 |

TABLE 5

| Name | Sequence | SEQ ID NO. |
|---|---|---|
| TRBJ_R1 | AACCAGGAGTCCTCCGC | 313 |
| TRBJ_R2 | ACGGTCAGCCTAGAGCCTT | 314 |
| TRBJ_R3 | AGTCTGGTGCCTTGTCCAA | 315 |
| TRBJ_R4 | CACGGTCAGCCTGCTGC | 316 |
| TRBJ_R5 | CCCATCACCAAAATGCTGGG | 317 |
| TRBJ_R6 | CCTGGGCCAAAATACTGCG | 318 |
| TRBJ_R7 | CGGCCCGAAGTACTGCT | 319 |
| TRBJ_R8 | CGGCGCCGAAGTACTGA | 320 |
| TRBJ_R9 | CTGGCCCGAAGAACTGC | 321 |
| TRBJ_R10 | GAGCCAACTTCCCTCTCCAA | 322 |
| TRBJ_R11 | GCCTGGTCCCATTCCCAAA | 323 |
| TRBJ_R12 | GCTGGGTTCCACTGCCAAA | 324 |
| TRBJ_R13 | TCCCGTTCCCAAAGTGGAG | 325 |
| TRBJ_R14 | TGACCGTGAGCCTGGTG | 326 |
| TRBJ_R15 | TGGCCCGAAGTACTGGG | 327 |
| TRBJ_R16 | TTAACCTGGTCCCCGAACC | 328 |
| TRBJ_R17 | GACCGTGAGCCTGGTGC | 329 |
| TRBJ_R18 | CAGGAGCCGCGTGCCTG | 330 |
| TRBJ_R19 | AGCACTGTCAGCCGGGT | 331 |
| TRBJ_R20 | CCAGCACGGTCAGCCTG | 332 |
| TRBJ_R21 | CTAGCACGGTGAGCCGT | 333 |
| TRBJ_R22 | AGCACTGAGAGCCGGGTC | 334 |
| TRBJ_R23 | CAGTACGGTCAGCCTAGAGC | 335 |
| TRBJ_R24 | CCAGAACCAGGAGTCCTCCG | 336 |
| TRBJ_R25 | CTGTCACAGTGAGCCTGGTC | 337 |
| TRBJ_R26 | CCAAGACAGAGAGCTGGGTTC | 338 |

TABLE 5-continued

| Name | Sequence | SEQ ID NO. |
|---|---|---|
| TRBJ_R27 | CTACAACTGTGAGTCTGGTGCC | 339 |
| TRBJ_R28 | CTAGGATGGAGAGTCGAGTCCC | 340 |
| TRBJ_R29 | CTACAACGGTTAACCTGGTCCC | 341 |
| TRBJ_R30 | CTACAACAGTGAGCCAACTTCCC | 342 |
| TRBJ_R31 | GTGACCGTGAGCCTGGT | 343 |
| TRBJ_R32 | TGTGACCGTGAGCCTGG | 344 |
| TRBJ_R33 | GTGACCGTGAGCCTGGTG | 345 |
| TRBJ_R34 | TGTGACCGTGAGCCTGGT | 346 |
| TRBJ_R35 | CTGTGACCGTGAGCCTGG | 347 |
| TRBJ_R36 | CAGGAGTCCTCCGCCCA | 348 |
| TRBJ_R37 | ACCAGGAGTCCTCCGCC | 349 |
| TRBJ_R38 | ACTGAGAGCCGGGTCCC | 350 |
| TRBJ_R39 | CACTGAGAGCCGGGTCC | 351 |
| TRBJ_R40 | GCACTGAGAGCCGGGTC | 352 |
| TRBJ_R41 | GCACGGTCAGCCTGCTG | 353 |
| TRBJ_R42 | CAGCACGGTCAGCCTGC | 354 |
| TRBJ_R43 | TAGCACGGTGAGCCGTG | 355 |
| TRBJ_R44 | CCAGGAGCCGCGTGCCTG | 356 |
| TRBJ_R45 | AACCAGGAGTCCTCCGCC | 357 |
| TRBJ_R46 | GAACCAGGAGTCCTCCGC | 358 |
| TRBJ_R47 | TAGCACGGTGAGCCGTGT | 359 |
| TRBJ_R48 | ACCAGGAGCCGCGTGCCTG | 360 |
| TRBJ_R49 | AACGGTTAACCTGGTCCCC | 361 |
| TRBJ_R50 | AGAACCAGGAGTCCTCCGC | 362 |
| TRBJ_R51 | CAGAACCAGGAGTCCTCCG | 363 |
| TRBJ_R52 | TACGGTCAGCCTAGAGCCTT | 364 |
| TRBJ_R53 | GTACGGTCAGCCTAGAGCCT | 365 |
| TRBJ_R54 | GGATGGAGAGTCGAGTCCCA | 366 |
| TRBJ_R55 | CAACGGTTAACCTGGTCCCC | 367 |
| TRBJ_R56 | AGTACGGTCAGCCTAGAGCC | 368 |
| TRBJ_R57 | AGGATGGAGAGTCGAGTCCC | 369 |
| TRBJ_R58 | ACAACGGTTAACCTGGTCCC | 370 |
| TRBJ_R59 | TGTCACAGTGAGCCTGGTCC | 371 |
| TRBJ_R60 | CAACTGTGAGTCTGGTGCCTT | 372 |
| TRBJ_R61 | GTACGGTCAGCCTAGAGCCTT | 373 |
| TRBJ_R62 | GGATGGAGAGTCGAGTCCCAT | 374 |
| TRBJ_R63 | ACAACTGTGAGTCTGGTGCCT | 375 |
| TRBJ_R64 | AGTACGGTCAGCCTAGAGCCT | 376 |
| TRBJ_R65 | AGGATGGAGAGTCGAGTCCCA | 377 |

TABLE 5-continued

| Name | Sequence | SEQ ID NO. |
|---|---|---|
| TRBJ_R66 | TACAACTGTGAGTCTGGTGCC | 378 |
| TRBJ_R67 | CAAGACAGAGAGCTGGGTTCC | 379 |
| TRBJ_R68 | TAGGATGGAGAGTCGAGTCCC | 380 |
| TRBJ_R69 | TACAACGGTTAACCTGGTCCC | 381 |
| TRBJ_R61 | GTACGGTCAGCCTAGAGCCTT | 373 |
| TRBJ_R62 | GGATGGAGAGTCGAGTCCCAT | 374 |
| TRBJ_R63 | ACAACTGTGAGTCTGGTGCCT | 375 |
| TRBJ_R64 | AGTACGGTCAGCCTAGAGCCT | 376 |
| TRBJ_R65 | AGGATGGAGAGTCGAGTCCCA | 377 |
| TRBJ_R66 | TACAACTGTGAGTCTGGTGCC | 378 |
| TRBJ_R67 | CAAGACAGAGAGCTGGGTTCC | 379 |
| TRBJ_R68 | TAGGATGGAGAGTCGAGTCCC | 380 |
| TRBJ_R69 | TACAACGGTTAACCTGGTCCC | 381 |
| TRBJ_R70 | ACAACTGTGAGTCTGGTGCCTT | 382 |
| TRBJ_R71 | AAGACAGAGAGCTGGGTTCCAC | 383 |
| TRBJ_R72 | AGGATGGAGAGTCGAGTCCCAT | 384 |
| TRBJ_R73 | ACAACAGTGAGCCAACTTCCCT | 385 |
| TRBJ_R74 | TACAACTGTGAGTCTGGTGCCT | 386 |
| TRBJ_R75 | CAAGACAGAGAGCTGGGTTCCA | 387 |
| TRBJ_R76 | TAGGATGGAGAGTCGAGTCCCA | 388 |
| TRBJ_R77 | TACAACGGTTAACCTGGTCCCC | 389 |
| TRBJ_R78 | TACAACTGTGAGTCTGGTGCCTT | 390 |
| TRBJ_R79 | TAGGATGGAGAGTCGAGTCCCAT | 391 |
| TRBJ_R80 | TACAACAGTGAGCCAACTTCCCT | 392 |
| TRBJ_R81 | CTACAACTGTGAGTCTGGTGCCT | 393 |
| TRBJ_R82 | CTAGGATGGAGAGTCGAGTCCCA | 394 |
| TRBJ_R83 | CTACAACTGTGAGTCTGGTGCCTT | 395 |
| TRBJ_R84 | CTAGGATGGAGAGTCGAGTCCCAT | 396 |
| TRBJ_R70 | ACAACTGTGAGTCTGGTGCCTT | 382 |
| TRBJ_R71 | AAGACAGAGAGCTGGGTTCCAC | 383 |
| TRBJ_R72 | AGGATGGAGAGTCGAGTCCCAT | 384 |
| TRBJ_R73 | ACAACAGTGAGCCAACTTCCCT | 385 |
| TRBJ_R74 | TACAACTGTGAGTCTGGTGCCT | 386 |
| TRBJ_R75 | CAAGACAGAGAGCTGGGTTCCA | 387 |
| TRBJ_R76 | TAGGATGGAGAGTCGAGTCCCA | 388 |
| TRBJ_R77 | TACAACGGTTAACCTGGTCCCC | 389 |
| TRBJ_R78 | TACAACTGTGAGTCTGGTGCCTT | 390 |
| TRBJ_R79 | TAGGATGGAGAGTCGAGTCCCAT | 391 |
| TRBJ_R80 | TACAACAGTGAGCCAACTTCCCT | 392 |

TABLE 5-continued

| Name | Sequence | SEQ ID NO. |
|---|---|---|
| TRBJ_R81 | CTACAACTGTGAGTCTGGTGCCT | 393 |
| TRBJ_R82 | CTAGGATGGAGAGTCGAGTCCCA | 394 |
| TRBJ_R83 | CTACAACTGTGAGTCTGGTGCCTT | 395 |
| TRBJ_R84 | CTAGGATGGAGAGTCGAGTCCCAT | 396 |
| TRBJ_R85 | CTACAACAGTGAGCCAACTTCCCT | 397 |
| TRBJ_R86 | AACCAGGAGUCCUCCGC | 398 |
| TRBJ_R87 | ACGGTCAGCCUAGAGCCUT | 399 |
| TRBJ_R88 | AGTCTGGUGCCUTGUCCAA | 400 |
| TRBJ_R89 | CACGGUCAGCCUGCUGC | 401 |
| TRBJ_R90 | CCCAUCACCAAAATGCUGGG | 402 |
| TRBJ_R91 | CCUGGGCCAAAATACUGCG | 403 |
| TRBJ_R92 | CGGCCCGAAGUACUGCT | 404 |
| TRBJ_R93 | CGGCGCCGAAGUACUGA | 405 |
| TRBJ_R94 | CUGGCCCGAAGAACUGC | 406 |
| TRBJ_R95 | GAGCCAACUCCCUCUCCAA | 407 |
| TRBJ_R96 | GCCTGGUCCCATUCCCAAA | 408 |
| TRBJ_R97 | GCTGGGUTCCACUGCCAAA | 409 |
| TRBJ_R98 | TCCCGTUCCCAAAGUGGAG | 410 |
| TRBJ_R99 | TGACCGUGAGCCTGGUG | 411 |
| TRBJ_R100 | TGGCCCGAAGUACUGGG | 412 |
| TRBJ_R101 | TUAACCTGGUCCCCGAACC | 413 |
| TRBJ_R102 | GACCGUGAGCCTGGUGC | 414 |
| TRBJ_R103 | CAGGAGCCGCGUGCCUG | 415 |
| TRBJ_R104 | AGCACUGUCAGCCGGGT | 416 |
| TRBJ_R105 | CCAGCACGGUCAGCCUG | 417 |
| TRBJ_R106 | CUAGCACGGUGAGCCGT | 418 |
| TRBJ_R107 | AGCACUGAGAGCCGGGUC | 419 |
| TRBJ_R108 | CAGTACGGUCAGCCUAGAGC | 420 |
| TRBJ_R109 | CCAGAACCAGGAGUCCUCCG | 421 |
| TRBJ_R110 | CTGTCACAGUGAGCCTGGUC | 422 |
| TRBJ_R111 | CCAAGACAGAGAGCUGGGTUC | 423 |
| TRBJ_R112 | CTACAACUGUGAGTCTGGUGCC | 424 |
| TRBJ_R113 | CTAGGAUGGAGAGTCGAGUCCC | 425 |
| TRBJ_R114 | CTACAACGGUTAACCTGGUCCC | 426 |
| TRBJ_R115 | CTACAACAGUGAGCCAACUCCC | 427 |
| TRBJ_R116 | GTGACCGUGAGCCUGGT | 428 |
| TRBJ_R117 | TGTGACCGUGAGCCUGG | 429 |
| TRBJ_R118 | GTGACCGUGAGCCTGGUG | 430 |
| TRBJ_R119 | TGTGACCGUGAGCCUGGT | 431 |

TABLE 5-continued

| Name | Sequence | SEQ ID NO. |
|---|---|---|
| TRBJ_R120 | CTGTGACCGUGAGCCUGG | 432 |
| TRBJ_R121 | CAGGAGUCCUCCGCCCA | 433 |
| TRBJ_R122 | ACCAGGAGUCCUCCGCC | 434 |
| TRBJ_R123 | ACUGAGAGCCGGGUCCC | 435 |
| TRBJ_R124 | CACUGAGAGCCGGGUCC | 436 |
| TRBJ_R125 | GCACUGAGAGCCGGGUC | 437 |
| TRBJ_R126 | GCACGGUCAGCCUGCUG | 438 |
| TRBJ_R127 | CAGCACGGUCAGCCUGC | 439 |
| TRBJ_R128 | TAGCACGGUGAGCCGUG | 440 |
| TRBJ_R129 | CCAGGAGCCGCGUGCCUG | 441 |
| TRBJ_R130 | AACCAGGAGUCCUCCGCC | 442 |
| TRBJ_R131 | GAACCAGGAGUCCUCCGC | 443 |
| TRBJ_R132 | TAGCACGGUGAGCCGUGT | 444 |
| TRBJ_R133 | ACCAGGAGCCGCGUGCCUG | 445 |
| TRBJ_R134 | AACGGUAACCTGGUCCCC | 446 |
| TRBJ_R135 | AGAACCAGGAGUCCUCCGC | 447 |
| TRBJ_R136 | CAGAACCAGGAGUCCUCCG | 448 |
| TRBJ_R137 | TACGGTCAGCCUAGAGCCUT | 449 |
| TRBJ_R138 | GTACGGUCAGCCUAGAGCCT | 450 |
| TRBJ_R139 | GGATGGAGAGUCGAGUCCCA | 451 |
| TRBJ_R140 | CAACGGUUAACCTGGUCCCC | 452 |
| TRBJ_R141 | AGTACGGUCAGCCUAGAGCC | 453 |
| TRBJ_R142 | AGGATGGAGAGUCGAGUCCC | 454 |
| TRBJ_R143 | ACAACGGUUAACCTGGUCCC | 455 |
| TRBJ_R144 | TGTCACAGUGAGCCTGGUCC | 456 |
| TRBJ_R145 | CAACTGTGAGUCTGGTGCCUT | 457 |
| TRBJ_R146 | GTACGGUCAGCCTAGAGCCUT | 458 |
| TRBJ_R147 | GGATGGAGAGUCGAGUCCCAT | 459 |
| TRBJ_R148 | ACAACTGTGAGTCTGGUGCCT | 460 |
| TRBJ_R149 | AGTACGGUCAGCCUAGAGCCT | 461 |
| TRBJ_R150 | AGGATGGAGAGUCGAGUCCCA | 462 |
| TRBJ_R151 | TACAACTGUGAGTCTGGUGCC | 463 |
| TRBJ_R152 | CAAGACAGAGAGCUGGGTUCC | 464 |
| TRBJ_R153 | TAGGAUGGAGAGTCGAGUCCC | 465 |
| TRBJ_R154 | TACAACGGUUAACCTGGUCCC | 466 |
| TRBJ_R155 | ACAACTGTGAGUCTGGTGCCUT | 467 |
| TRBJ_R156 | AAGACAGAGAGCUGGGTUCCAC | 468 |
| TRBJ_R157 | AGGATGGAGAGUCGAGUCCCAT | 469 |
| TRBJ_R158 | ACAACAGUGAGCCAACTUCCCT | 470 |
| TRBJ_R159 | TACAACTGUGAGTCTGGUGCCT | 471 |
| TRBJ_R160 | CAAGACAGAGAGCUGGGTUCCA | 472 |
| TRBJ_R161 | TAGGAUGGAGAGTCGAGUCCCA | 473 |
| TRBJ_R162 | TACAACGGUUAACCTGGUCCCC | 474 |
| TRBJ_R163 | TACAACTGTGAGUCTGGTGCCUT | 475 |
| TRBJ_R164 | TAGGAUGGAGAGTCGAGUCCCAT | 476 |
| TRBJ_R165 | TACAACAGUGAGCCAACTUCCCT | 477 |
| TRBJ_R166 | CTACAACTGUGAGTCTGGUGCCT | 478 |
| TRBJ_R167 | CTAGGAUGGAGAGTCGAGUCCCA | 479 |
| TRBJ_R168 | CTACAACTGTGAGUCTGGTGCCUT | 480 |
| TRBJ_R169 | CTAGGAUGGAGAGTCGAGUCCCAT | 481 |
| TRBJ_R170 | CTACAACAGUGAGCCAACTUCCCT | 482 |

The following description of various exemplary embodiments is exemplary and explanatory only and is not to be construed as limiting or restrictive in any way. Other embodiments, features, objects, and advantages of the present teachings will be apparent from the description and accompanying drawings, and from the claims.

Although the present description described in detail certain exemplary embodiments, other embodiments are also possible and within the scope of the present invention. Variations and modifications will be apparent to those skilled in the art from consideration of the specification and figures and practice of the teachings described in the specification and figures, and the claims.

EXAMPLES

Provided immune repertoire compositions include, without limitation, reagents designed for library preparation and sequencing of rearranged genomic TCR beta gene sequences. Generally, gDNA was extracted from samples (e.g., blood samples, sorted cell samples, tumor samples (e.g., fresh, frozen, FFPE of various types)); libraries were generated, templates prepared, e.g., using Ion Chef™ System, then prepared templates were sequenced using next generation sequencing technology, e.g., an Ion S5™ System and sequence analysis was performed using Ion Reporter™ software. Kits suitable for extracting and/or isolating genomic DNA from biological samples are commercially available from, for example, Thermo Fisher Scientific and BioChain Institute Inc.

Example 1

Leukocyte genomic DNA was isolated and used in multiplex polymerase chain reactions to assess the TCR beta (TRB) immune repertoire. In a single multiplex PCR, sets of forward and reverse primers selected from Tables 3 and 5 were used as primer pairs in amplifying sequences from the V gene FR3 region to the J gene of TRB gDNA. In an exemplary V gene FR3-J amplification reaction, the multiplex primer set included 59 different TRB V gene (TRBV) forward primers SEQ ID NOs: 249-307 and 16 different TRB J gene (TRBJ) reverse primers SEQ ID NOs: 398-413.

To a single well of a 96-well PCR plate was added 2 microliters prepared gDNA (100 ng), 2 microliters of 2 µM TRBV (FR3) forward primer pool (containing 59 primers), 2 microliters of 2 µM TRBJ reverse primer pool (containing 16 primers), 4 microliters of 5× Ion AmpliSeq™ HiFi Mix (an amplification reaction mixture that can include glycerol, dNTPs, and Platinum® Taq High Fidelity DNA Polymerase (Invitrogen, Catalog No. 11304)), 2 microliters of 30 mM dNTP Mix (dGTP, dCTP, dATP, and dTTP at 7.5 mM each) and 8 microliters DNase/RNase free water to bring the final reaction volume to 20 microliters. The multiplex amplification reaction was performed with each primer present at 200 nM in the reaction.

The PCR plate was sealed, reaction mixtures mixed, and loaded into a thermal cycler (e.g., Veriti™ 96-well thermal cycler (Applied Biosystems)) and run on the following temperature profile to generate the amplicon library. An initial holding stage was performed at 95° C. for 7 minutes, followed by about 25 cycles of a denaturing stage at 95° C. for 30 seconds, an annealing stage at 60° C. for 45 seconds, and an extending stage for 72° C. for 45 seconds. After cycling, a final extension 72° C. for 10 minutes was performed and the amplicon library was held at 10° C. until proceeding. Typically, about 25 cycles are used to generate the amplicon library. For some applications, up to 30 cycles can be used.

The amplicon sample was briefly centrifuged to collect contents before proceeding. To the pre-amplified amplicon library (~20 microliters), 2 microliters of FuPa reagent was added. The reaction mixture was sealed, mixed thoroughly to ensure uniformity and incubated at 50° C. for 10 minutes, 55° C. for 10 minutes, 60° C. for 20 minutes, then held at 10° C. for up to 1 hour. The sample was briefly centrifuged to collect contents before proceeding.

After incubation, the reaction mixture proceeded directly to a ligation step. Here, the reaction mixture now containing the phosphorylated amplicon library was combined with 2 microliters of Ion Xpress™ Barcode Adapters, 5 µM each (Thermo Fisher), 4 microliters of Switch Solution (sold as a component of the Ion AmpliSeq™ Library Kit Plus, Thermo Fisher) and 2 microliters of DNA ligase, added last (sold as a component of the Ion AmpliSeq™ Library Kit Plus, Thermo Fisher), then incubated at the following: 22° C. for 30 minutes, 68° C. for 5 minutes, 72° C. for 5 minutes, then held at 10° C. for up to 24 hours. The sample was briefly centrifuged to collect contents before proceeding.

After the incubation step, 45 microliters (1.5× sample volume) of room temperature AMPure® XP beads (Beckman Coulter, Calif.) was added to ligated DNA and the mixture was pipetted thoroughly to mix the bead suspension with the DNA. The mixture was incubated at room temperature for 5 minutes, placed on a magnetic rack such as a DynaMag™-96 side magnet (Invitrogen, Part No. 12331D) for two minutes. After the solution had cleared, the supernatant was discarded. Without removing the plate from the magnetic rack, 150 microliters of freshly prepared 70% ethanol was introduced into the sample, and incubated while gently rotating the tube on the magnetic rack. After the solution cleared, the supernatant was discarded without disturbing the pellet. A second ethanol wash was performed, the supernatant discarded, and any remaining ethanol was removed by pulse-spinning the tube and carefully removing residual ethanol while not disturbing the pellet. The pellet was air-dried for about 5 minutes at room temperature. The ligated DNA was eluted from the beads in 50 microliters of low TE buffer.

The eluted libraries were quantitated by qPCR using the Ion Library TaqMan® Quantitation Kit (Ion Torrent, Cat. No. 4468802), according to manufacturer instructions. After quantification, the libraries were diluted to a concentration of about 25 picomolar.

An aliquot of the final library was used in template preparation and chip loading using the Ion Chef™ instrument according to the manufacturer's instructions. Sequencing was performed using Ion 540™ chips on the Ion S5™ System according to manufacturer instructions, and TRB sequence analysis was performed with the Ion Reporter™ software. Sequences generated from use of J gene primers were subjected to a J gene sequence inference process involving adding the inferred J gene sequence to the sequence read to create an extended sequence read, aligning the extended sequence read to a reference sequence, and identifying productive reads, as described herein. In addition, all of the generated sequence data was further subjected to the error identification and removal programs provided herein. Productive reads, rescued productive reads, and unproductive reads were reported.

For the exemplary TRB FR3-J assay using leukocyte gDNA as described above, sequence read lengths of about 60-85 nucleotides were obtained. Using the error identification and removal program provided herein yielded about 83M total reads, of which about 60% productive reads. From sample preparation to immune repertoire sequence read reporting, the turnaround time for this workflow was less than 48 hours.

Example 2

The TRB repertoire in TILs from a colon tumor sample was characterized. The primer sets used in the multiplex amplification reactions were 59 different TRBV FR3 forward primers SEQ ID NOs: 249-307 and 16 different TRBJ reverse primers SEQ ID NOs: 398-413. DNA was extracted from a FFPE colon tumor biopsy sample.

To a single well of a 96-well PCR plate was added 5 microliters prepared FFPE DNA (100 ng), 2 microliters of 2 µM TRBV FR3 forward primer pool (containing 59 primers), 2 microliters of 2 µM TRBJ reverse primer pool (containing 16 primers), 4 microliters of 5× Ion AmpliSeq™ HiFi Mix (an amplification reaction mixture that can include glycerol, dNTPs, and Platinum® Taq High Fidelity DNA Polymerase (Invitrogen, Catalog No. 11304)), 2 microliters of 30 mM dNTP Mix (dGTP, dCTP, dATP, and dTTP at 7.5 mM each) and 5 microliters DNase/RNase free water to bring the final reaction volume to 20 microliters. The multiplex amplification reaction was performed with each primer present at 200 nM in the reaction.

The amplification cycling, amplicon preparation, chip loading, and sequencing was performed as described in Example 1, with the exception that sequencing was performed using the Ion530™ chip on the Ion S5™ System according manufacturer instructions (Thermo Fisher Scientific). The generated sequence data was subjected to the error identification and removal programs provided herein.

The FFPE DNA assay yielded >9 M reads, of which about 55% were productive and about 25% were off-target. The mean read length was 68 nucleotides, and the mean CDR3 length was 36 nucleotides in length, and the Clone Normalized Shannon Entropy was 0.869114. Clone Normalized Shannon Entropy described how "even" clone representation is in the sample; the closer to 1.0, the more evenly sized the clonal populations are.

Example 3

The TRB repertoire in leukocyte gDNA was characterized using multiplex PCR followed by next generation sequencing. In the multiplex PCR, sets of forward and reverse primers selected from Tables 3 and 5 were used as primer pairs in amplifying sequences from the V gene FR3 region to the J gene of rearranged TCR beta gDNA. In this exemplary V gene FR3-J amplification reaction, the multiplex primer set included 59 different TRBV FR3 forward primers SEQ ID NOs: 249-307 and 14 different TRBJ reverse primers SEQ ID NOs: 414-427.

To a single well of a 96-well PCR plate was added 2 microliters prepared leukocyte gDNA (100 ng), 4 microliters of 1 µM Primer Mix (59 TRBV FR3 forward primers and 14 TRBJ reverse primers, 1 µM each), 4 microliters of 5× Ion AmpliSeq™ HiFi Mix (Invitrogen, Catalog No. 11304), 2 microliters of dNTP Mix (dGTP, dCTP, dATP, and dTTP; 7.5 mM each) and 8 microliters DNase/RNase free water to bring the final reaction volume to 20 microliters. The multiplex amplification reaction was performed with each primer present at 200 nM in the reaction.

The multiplex amplification cycling (25 cycles), amplicon preparation, chip loading, and sequencing was performed as described in Example 1, with the exception that sequencing was performed using the Ion530™ chip on the Ion S5™ System according manufacturer instructions (Thermo Fisher Scientific). The generated sequence data was subjected to the error identification and removal programs provided herein.

The leukocyte gDNA assay yielded >2.9M sequence reads, of which about 73% were productive, about 7% were off-target, and about 20% were unproductive. The mean sequence read length was 85 nucleotides and the mean CDR3 length was 37 nucleotides in length. The number of clones identified was 17,576 and the Clone Normalized Shannon Entropy was 0.843073.

What is claimed is:

1. A method for amplification of rearranged genomic DNA sequences of an immune receptor repertoire in a sample, comprising:

performing a single multiplex amplification reaction to amplify target immune receptor DNA template molecules having rearranged VDJ or VJ gene segments, using at least one set of:
i) (a) a plurality of V gene primers directed to a majority of different V genes of at least one immune receptor coding sequence comprising at least a portion of framework region 3 (FR3) within the V gene,
(b) a plurality of V gene primers directed to a majority of different V genes of at least one immune receptor coding sequence comprising at least a portion of framework region 2 (FR2) within the V gene, or
(c) a plurality of V gene primers directed to a majority of different V genes of at least one immune receptor coding sequence comprising at least a portion of framework region 1 (FR1) within the V gene; and
ii) a plurality of J gene primers directed to at least a portion of a majority of different J genes of the at least one immune receptor coding sequence,
wherein each set of i) and ii) primers is directed to coding sequences of the same target immune receptor gene selected from a T cell receptor gene or an antibody receptor gene and wherein performing the amplification using the at least one set of i) and ii) primers results in amplicon molecules representing the target immune receptor repertoire in the sample, and wherein each of the plurality of V gene primers and the plurality of J gene primers includes two or more modified nucleotides having a cleavable group within the primer sequence, at least one of which is included near or at the 3' termini of the primer and at least one of which is included at, or about the center nucleotide position of the primer sequence;
thereby generating immune receptor amplicon molecules comprising the target immune receptor repertoire.

2. The method of claim 1, wherein each of the plurality of V gene primers and/or the plurality of J gene primers has any one or more of the following criteria:
(1) length is about 15 to about 40 bases in length;
(2) Tm of from above 60° C. to about 70° C.;
(3) has low cross-reactivity with non-target sequences present in the sample;
(4) at least the first four nucleotides (going from 3' to 5' direction) are non-complementary to any sequence within any other primer present in the same reaction; and
(5) are non-complementary to any consecutive stretch of at least 5 nucleotides within any other produced target amplicon.

3. The method of claim 1, wherein the at least one set of i) and ii) is i)(a) and ii), wherein the plurality of V gene primers anneal to at least a portion of the FR3 region of the template molecules, and wherein the plurality of J gene primers comprises at least ten primers that anneal to at least a portion of the J gene portion of the template molecules.

4. The method of claim 3, wherein the generated immune receptor amplicons are about 70 to about 100 nucleotides in length.

5. The method of claim 3, wherein the at least one set of i) and ii) is selected from the primers of Table 3 and Table 5.

6. The method of claim 3, wherein the plurality of V gene primers is about 45 to about 80 different V gene primers.

7. The method of claim 1, wherein the target DNA is genomic DNA extracted from a biological sample.

8. The method of claim 7, wherein the biological sample is selected from the group consisting of peripheral blood mononuclear cells (PBMCs), T cell, B cell, circulating tumor cells, and tumor infiltrating lymphocytes (TILs).

9. A method for preparing an immune receptor repertoire library, comprising:
i) generating the target immune receptor amplicon molecules according to claim 1 and treating the amplicon molecules by digesting a modified nucleotide within the amplicon molecules' primer sequences;
ii) ligating at least one adapter to at least one of the treated amplicon molecules, thereby producing a library of adapter-ligated target immune receptor amplicon molecules comprising the target immune receptor repertoire.

10. The method of claim 9, wherein the ligating comprises ligating a different adapter to each end of the at least one of the treated amplicon molecules.

11. The method of claim 10, wherein each of the two different adapters includes a different barcode sequence.

12. The method of claim 9, wherein the method further includes clonally amplifying a portion of the at least one adapter-ligated target immune receptor amplicon molecule.

13. A method for providing sequence of the immune repertoire in a sample, comprising:
i) performing sequencing of the target immune receptor repertoire library of claim 9; and
ii) determining the sequence of the immune receptor amplicon molecules, wherein determining the sequence includes obtaining initial sequence reads, adding inferred J gene sequence to the sequence read to create an extended sequence read, aligning the extended sequence read to a reference sequence, identifying productive reads, identifying and correcting one or more indel errors in the V gene sequence to generate rescued productive reads; and
iii) reporting the sequences of the target immune receptor molecules, thereby providing sequence of the immune repertoire in the sample.

14. The method of claim 13, further comprising sequence read clustering and immune receptor clonotype reporting.

15. The method of claim 13, wherein the combination of productive reads and rescued productive reads is at least 40% of the sequencing reads for the immune receptor amplicons.

* * * * *